United States Patent
El Qacemi et al.

(10) Patent No.: US 9,233,920 B2
(45) Date of Patent: Jan. 12, 2016

(54) PROCESS FOR THE PREPARATION OF DIHYDROPYRROLE DERIVATIVES

(75) Inventors: Myriem El Qacemi, Stein (CH); Helmars Smits, Stein (CH); Jerome Yves Cassayre, Stein (CH); Nicholas Phillip Mulholland, Bracknell (GB); Peter Renold, Stein (CH); Edouard Godineau, Stein (CH); Thomas Pitterna, Stein (CH)

(73) Assignees: Syngenta Participations AG, Basel (CH); Syngenta Limited, Guildford (GB)

( * ) Notice: Subject to any disclaimer, the term of this patent is extended or adjusted under 35 U.S.C. 154(b) by 501 days.

(21) Appl. No.: 13/703,630

(22) PCT Filed: Jun. 14, 2011

(86) PCT No.: PCT/EP2011/059823
§ 371 (c)(1),
(2), (4) Date: Mar. 4, 2013

(87) PCT Pub. No.: WO2011/154555
PCT Pub. Date: Dec. 15, 2011

(65) Prior Publication Data
US 2013/0237583 A1    Sep. 12, 2013

(30) Foreign Application Priority Data

Jun. 11, 2010   (WO) ................. PCT/EP2010/058207
Dec. 22, 2010   (EP) ..................................... 10196633

(51) Int. Cl.
| | | |
|---|---|---|
| C07D 207/46 | (2006.01) | |
| C07D 207/20 | (2006.01) | |
| C07D 401/04 | (2006.01) | |
| C07D 413/12 | (2006.01) | |
| C07D 413/14 | (2006.01) | |
| C07D 417/14 | (2006.01) | |
| A01N 43/36  | (2006.01) | |

(52) U.S. Cl.
CPC .............. *C07D 207/46* (2013.01); *A01N 43/36* (2013.01); *C07D 207/20* (2013.01); *C07D 401/04* (2013.01); *C07D 413/12* (2013.01); *C07D 413/14* (2013.01); *C07D 417/14* (2013.01)

(58) Field of Classification Search
None
See application file for complete search history.

(56) References Cited

U.S. PATENT DOCUMENTS 8,268,754 B2 *   9/2012   Mita et al. ................ 504/283

FOREIGN PATENT DOCUMENTS

| WO | WO2009072621 | * | 6/2009 |
| WO | WO2011128299 | * | 10/2011 |

OTHER PUBLICATIONS

Matoba, et al., Angew. Chem. Int. Ed., 49:5762 (Jul. 7, 2010).*

* cited by examiner

*Primary Examiner* — Michael Barker
(74) *Attorney, Agent, or Firm* — James Cueva

(57) ABSTRACT

The present invention provides stereoselective processes for the preparation of compounds of formula (I) wherein P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted; $R^1$ is chlorodifluoromethyl or trifluoromethyl; $R^2$ is optionally substituted aryl or optionally substituted heteroaryl; n is 0 or 1; including the process comprising (a-i) reacting a compound of formula II wherein P, $R^1$ and $R^2$ are as defined for the compound of formula I; with nitromethane in the presence a chiral catalyst to give a compound of formula III Wherein P, $R^1$ and $R^2$ are as defined for the compound of formula I; and (a-ii) reductively cyclizing the compound of formula III to give the compound of formula I. The invention also provides intermediates useful for processes for the synthesis of compounds of formula (I).

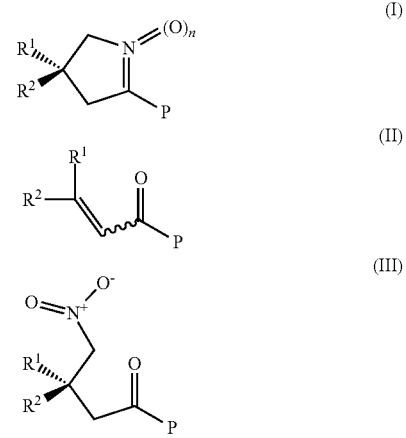

16 Claims, No Drawings

PROCESS FOR THE PREPARATION OF DIHYDROPYRROLE DERIVATIVES

This application is a 371 of International Application No. PCT/EP2011/059823 filed Jun. 14, 2011, which claims priority to PCT/EP2010/058207 filed Jun. 11, 2010 and EP 10196633.1 filed Dec. 22, 2010, the contents of which are incorporated herein by reference.

The present invention relates to the synthesis of substituted dihydro-pyrrole derivatives and in particular to the stereoselective synthesis of substituted dihydro-pyrrole derivatives. The present invention relates more particularly to the stereoselective synthesis of substituted dihydro-pyrrole derivatives that have pesticidal activity.

Certain dihydro-pyrrole derivatives with insecticidal properties are disclosed in, for example, JP 2007/091708, JP 2008/133273, JP 2010/254629, WO09097992, WO09072621 and WO2010/020522. Such dihydro-pyrrole derivatives include at least one chiral centre at one of the ring members of the dihydro-pyrrole moiety. The present invention provides a process for selectively synthesizing enantiomers of such compounds as well as intermediates that can be used in the synthesis of such compounds.

Accordingly, in a first aspect the invention provides a process for the preparation of the compound of formula I

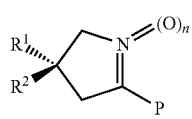

(I)

wherein
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
$R^1$ is chlorodifluoromethyl or trifluoromethyl;
$R^2$ is optionally substituted aryl or optionally substituted heteroaryl;
n is 0 or 1;
comprising
(a-i) reacting a compound of formula II

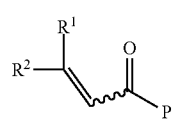

(II)

wherein P, $R^1$ and $R^2$ are as defined for the compound of formula I;
with nitromethane in the presence a chiral catalyst to give a compound of formula III

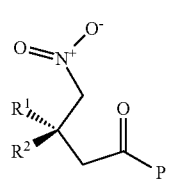

(III)

wherein P, $R^1$ and $R^2$ are as defined for the compound of formula I; and (a-ii) reductively cyclising the compound of formula III to give the compound of formula I;
or
(b-i) reacting a compound of formula II

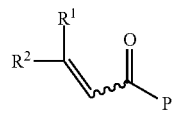

(II)

wherein P, $R^1$ and $R^2$ are as defined for the compound of formula I;
with a source of cyanide in the presence of a chiral catalyst to give a compound of formula IV

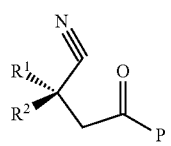

(IV)

wherein P, $R^1$ and $R^2$ are as defined for the compound of formula I; and
(b-ii) reductively cyclising the compound of formula IV to give the compound of formula I, wherein n is 0;
or
(c-i) reacting a compound of formula II

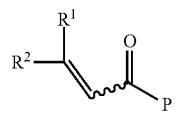

(II)

wherein P, $R^1$ and $R^2$ are as defined for the compound of formula I;
with a compound of formula XXII

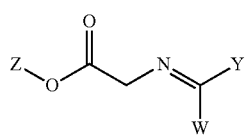

(XXII)

wherein W is hydrogen or optionally substituted aryl, Y is optionally substituted aryl, and Z is optionally substituted alkyl or optionally substituted arylalkylene;
in the presence a chiral catalyst to give a compound of formula XXIII

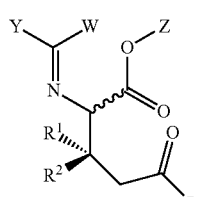

(XXIII)

wherein P, $R^1$ and $R^2$ are as defined for the compound of formula I, and Y, W and Z are as defined for the compound of formula XXII;

(c-ii) treating the compound of formula XXIII with a suitable acid or a suitable base to release Y—C(=O)—W and give the compound of formula XXIV

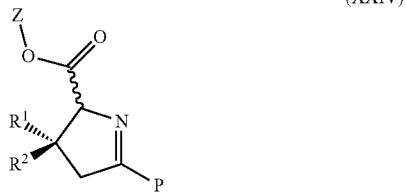

wherein P, $R^1$ and $R^2$ are as defined for the compound of formula I and Z is as defined for the compound of formula XXII; and
(c-iii) decarboxylating the compound XXIV to give the compound of formula I, wherein n is 0;
or
(d-i) reacting a compound of formula XXV

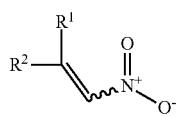

wherein $R^1$ and $R^2$ are as defined for the compound of formula I;
with a compound of formula XXVI

wherein P is as defined for the compound of formula I;
in the presence a chiral catalyst to give a compound of formula III

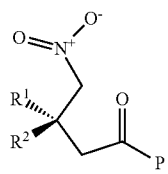

wherein P, $R^1$ and $R^2$ are as defined for the compound of formula I; and
(d-ii) reductively cyclising the compound of formula III to give the compound of formula I.

In one embodiment the invention provides a process for the preparation of the compound of formula I comprising performing steps (a-i) and (a-ii). In another embodiment the invention provides a process for the preparation of the compound of formula I wherein n is 0 comprising performing steps (b-i) and (b-ii). In another embodiment the invention provides a process for the preparation of the compound of formula I wherein n is 0, comprising performing steps (c-i), (c-ii) and (c-iii). In another embodiment the invention provides a process for the preparation of the compound of formula I comprising performing steps (d-i) and (d-ii). Processes (a) and (b) are preferred.

Generally, molecules with the opposite stereochemistry of compounds of formula (I) at the chiral centre indicated are less biologically active.

In a further aspect the invention provides a process for the preparation of a mixture comprising the compounds of formula I and IA

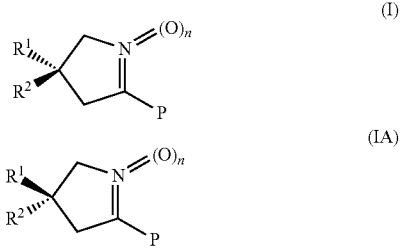

wherein
$R^1$ is chlorodifluoromethyl or trifluoromethyl;
$R^2$ is optionally substituted aryl or optionally substituted heteroaryl;
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
n is 0 or 1;
wherein the mixture is enriched for the compound of formula I;
comprising performing steps (a-i) and (a-ii) or steps (b-i) and (b-ii), or steps (c-i), (c-ii) and (c-iii), or steps (d-i) and (d-ii) above.

The preferred definitions of $R^1$, $R^2$, P and n as defined for the compound of formula I also apply to the compound of formula IA.

In a further aspect the invention provides a compound of formula I

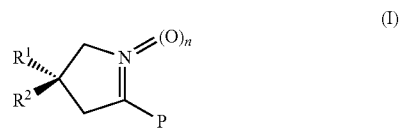

wherein
$R^1$ is chlorodifluoromethyl or trifluoromethyl;
$R^2$ is optionally substituted aryl or optionally substituted heteroaryl;
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
n is 0 or 1.

In a further aspect the invention provides a mixture comprising a compound of formula I and a compound of formula IA

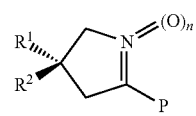

(I)

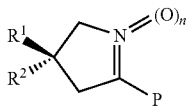

(IA)

wherein
R¹ is chlorodifluoromethyl or trifluoromethyl;
R² is optionally substituted aryl or optionally substituted heteroaryl;
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
n is 0 or 1;
wherein the mixture is enriched for the compound of formula I.

In a further aspect the invention provides a compound of formula III

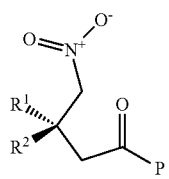

(III)

wherein $R^1$, $R^2$ and P are as defined for the compound of formula I.
The preferred definitions of $R^1$, $R^2$ and P as defined for the compound of formula I also apply to the compound of formula III.

In a further aspect the invention provides a mixture comprising a compound of formula III and a compound of formula IIIA

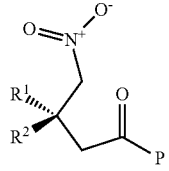

(III)

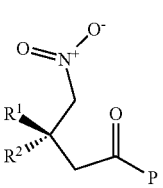

(IIIA)

wherein P, $R^1$ and $R^2$ are as defined for the compound of formula I;
wherein the mixture is enriched for the compound of formula III.

The preferred definitions of $R^1$, $R^2$ and P as defined for the compound of formula I also apply to the compound of formula III and IIIA.

In a further aspect the invention provides a compound of formula IV

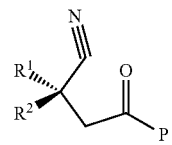

(IV)

wherein P, $R^1$ and $R^2$ are as defined for the compound of formula I.
The preferred definitions of $R^1$, $R^2$ and P as defined for the compound of formula I also apply to the compound of formula IV.

In a further aspect the invention provides a mixture comprising a compound of formula IV and a compound of formula IVA (IV)

(IVA)

wherein $R^1$, $R^2$ and P are as defined for the compound of formula I;
wherein the mixture is enriched for the compound of formula IV.
The preferred definitions of $R^1$, $R^2$ and P as defined for the compound of formula I also apply to the compound of formula IV and IVA.

In a further aspect the invention provides a compound of formula XXIII

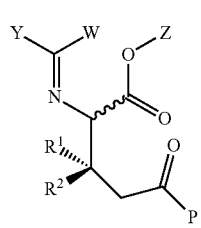

(XXIII)

wherein P, $R^1$ and $R^2$ are as defined for the compound of formula I, wherein Y is hydrogen or optionally substituted aryl, W is optionally substituted aryl, and Z is optionally substituted alkyl or optionally substituted arylalkylene. The preferred definitions of $R^1$, $R^2$ and P as defined for the compound of formula I also apply to the compound of formula XXIII. Y and W are preferably independently hydrogen or phenyl, more preferably at least one of Y and W is phenyl, even more preferably both Y and W are phenyl. Z is preferably $C_1$-$C_8$ alkyl or phenyl-$C_1$-$C_6$alkylene, more preferably $C_1$-$C_8$ alkyl or benzyl.

In a further aspect the invention provides a mixture comprising a compound of formula XXIII and a compound of formula XXIIIA

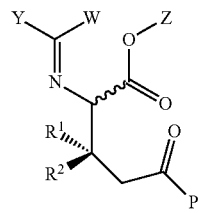

(XXIII)

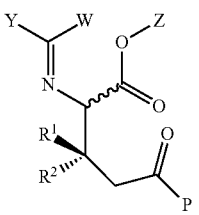

(XXIIIA)

wherein $R^1$, $R^2$ and P are as defined for the compound of formula I, wherein Y is hydrogen or optionally substituted aryl, W is optionally substituted aryl, and Z is optionally substituted alkyl or optionally substituted arylalkylene, wherein the mixture is enriched for the compound of formula XXIII. The preferred definitions of $R^1$, $R^2$, and P as defined for the compound of formula I also apply to the compounds of formula I. Y and W are preferably independently hydrogen or phenyl, more preferably at least one of Y and W is phenyl, even more preferably both Y and W are phenyl. Z is preferably $C_1$-$C_8$ alkyl or phenyl-$C_1$-$C_6$alkylene, more preferably $C_1$-$C_8$ alkyl or benzyl.

In a further aspect the invention provides a compound of formula XXIV

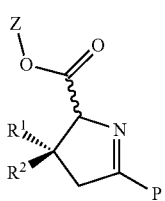

(XXIV)

wherein P, $R^1$ and $R^2$ are as defined for the compound of formula I, and Z is optionally substituted alkyl or optionally substituted arylalkylene. The preferred definitions of $R^1$, $R^2$ and P as defined for the compound of formula I also apply to the compound of formula XXIII. Z is preferably $C_1$-$C_8$ alkyl or phenyl-$C_1$-$C_6$alkylene, more preferably $C_1$-$C_8$ alkyl or benzyl.

In a further aspect the invention provides a mixture comprising a compound of formula XXIV and a compound of formula XXIVA

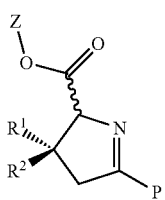

(XXIV)

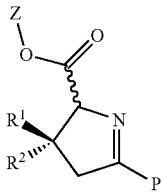

(XXIVA)

wherein $R^1$, $R^2$ and P are as defined for the compound of formula I, and Z is optionally substituted alkyl or optionally substituted arylalkylene, wherein the mixture is enriched for the compound of formula XXIV. The preferred definitions of $R^1$, $R^2$, and P as defined for the compound of formula I also apply to the compounds of formula I. Z is preferably $C_1$-$C_8$ alkyl or phenyl-$C_1$-$C_6$alkylene, more preferably $C_1$-$C_8$ alkyl or benzyl.

In enantiomerically enriched mixtures of the invention, the molar proportion of the enriched compound in the mixture compared to the total amount of both enantiomers is for example greater than 50%, e.g. at least 55, 60, 65, 70, 75, 80, 85, 90, 95, 96, 97, 98, or at least 99%.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are, unless indicated to the contrary, preferably $C_1$-$C_6$, more preferably $C_1$-$C_4$, most preferably $C_1$-$C_3$ alkyl groups.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are, unless indicated to the contrary, preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are, unless indicated to the contrary, preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are, unless indicated to the contrary, preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl-, haloalkylsulfonyl-, haloalkylcarbonyl- or haloalkoxycarbonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups can be in mono- or bi-cyclic form and are, for example, cyclopropyl, cyclobutyl, cyclohexyl and bicyclo[2.2.1]heptan-2-yl. The cycloalkyl groups are, unless indicated to the contrary, preferably $C_3$-$C_8$, more preferably $C_3$-$C_6$ cycloalkyl groups.

Aryl groups are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is, unless indicated to the contrary, preferably substituted by one to four substituents, most preferably by one to three substituents.

Heteroaryl groups are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is, unless indicated to the contrary, preferably substituted by one to four substituents, most preferably by one to three substituents.

Heterocyclyl groups are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Where a heterocyclyl moiety is said to be substituted, the heterocyclyl moiety is, unless indicated to the contrary, preferably substituted by one to four substituents, most preferably by one to three substituents.

Bearing in mind the stereocentre which is the subject of the invention, the invention otherwise includes all isomers of compounds of formula I, salts and N-oxides thereof, including enantiomers, diastereomers and tautomers. Tautomers of the compounds of formula I include the enamine form, for example. These are covered by the invention.

Preferred substituent values in compounds of formula I are as follows, which may be combined in any order. These preferred substituent values also apply to other compounds of the invention in which the same substituents are present.

$R^1$ is preferably trifluoromethyl.

$R^2$ is aryl or aryl substituted by one to five $R^3$, or heteroaryl or heteroaryl substituted by one to five $R^3$. Preferably, $R^2$ is phenyl or phenyl substituted by one to three $R^3$.

Each $R^3$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkylamino, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^4$, or heterocyclyl or heterocyclyl substituted by one to five $R^4$. Preferably, each $R^3$ is independently halogen, cyano, nitro, $C_1$-$C_8$alkyl, $C_1$-$C_8$haloalkyl, $C_1$-$C_8$alkoxy or $C_1$-$C_8$haloalkoxy, more preferably bromo, chloro, fluoro, cyano, methyl, trifluoromethyl, methoxy or trifluoromethoxy, preferably bromo, chloro or trifluoromethyl, most preferably bromo or chloro.

Preferably P is P1 or P2

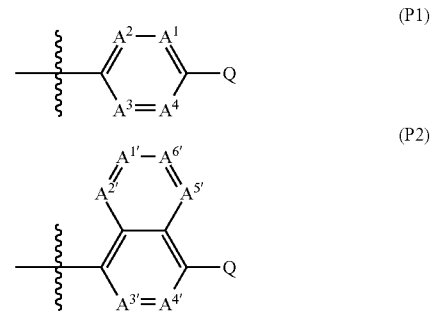

More preferably P is P3

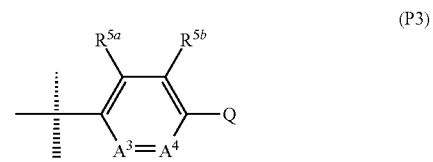

$A^1$, $A^2$, $A^3$, and $A^4$ are independently of each other C—H, C—$R^5$ or nitrogen, provided that no more than two of $A^1$, $A^2$, $A^3$, and $A^4$ are nitrogen. Preferably $A^1$ is C—$R^5$. Preferably $A^2$ is C—H. Preferably, $A^3$ and $A^4$ are C—H, or one of $A^3$ and $A^4$ is C—H and the other is nitrogen. More preferably, $A^3$ and $A^4$ are C—H.

$A^{1'}$, $A^{2'}$, $A^{3'}$, $A^{4'}$, $A^{5'}$ and $A^{6'}$ are independently of each other C—H, C—$R^5$ or nitrogen provided that no more than two of $A^{1'}$, $A^{2'}$, $A^{3'}$, $A^{4'}$, $A^{5'}$ and $A^{6'}$ are nitrogen. Preferably $A^{1'}$, $A^{2'}$, $A^{3'}$, $A^{4'}$, $A^{5'}$ and $A^{6'}$ are C—H.

The ring formed by $A^1$, $A^2$, $A^3$ and $A^4$, or $A^{1'}$, $A^{2'}$, $A^{3'}$, $A^{4'}$, $A^{5'}$ and $A^{6'}$ may, for example, be phenyl, pyridyl, pyrimidine, pyrazine, pyridazine, naphthyl or quinoline.

Each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl or $C_1$-$C_8$haloalkylsulfonyl. Preferably, each $R^5$ is independently halogen, $C_1$-$C_8$alkyl, $C_1$-$C_8$haloalkyl or $C_2$-$C_8$alkenyl. More preferably, each $R^5$ is independently bromo, chloro, fluoro, methyl, trifluoromethyl or vinyl, most preferably each $R^5$ is methyl.

$R^{5a}$ is hydrogen and $R^{5b}$ is methyl or $R^{5a}$ and $R^{5b}$ together form a —CH=CH—CH=CH— bridge.

Q is hydrogen, halogen, nitro, $NH_2$, cyano, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_3$-$C_8$haloalkynyl, $C_3$-$C_{10}$cycloalkyl, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, arylsulfonyl or arylsulfonyl substituted by one to five groups independently selected from $C_1$-$C_4$alkyl and nitro, —N($R^6$)$R^{7b}$, —C(=$W^5$)N($R^6$)$R^7$, —C($R^{15}$)($R^{16}$)N($R^{17}$)$R^{18}$, C(=$W^5$)O$R^{7a}$, —C(=$W^5$)$R^{13}$, —O$R^{14}$, aryl or aryl substituted by one to five $Z^1$, heterocyclyl or heterocyclyl substituted by one to five $Z^1$. Preferably, Q is cyano, halogen, nitro, $NH_2$, arylsulfonyl or arylsulfonyl substituted by one to five groups independently selected from $C_1$-$C_4$alkyl and nitro, heterocyclyl or heterocyclyl substituted by one to five $Z^1$, —$OR^{14}$, —C(═O)N($R^6$)$R^7$, —C(═O)$OR^{7a}$, —C(═O)$R^{13}$, or —C($R^{15}$)($R^{16}$)N($R^{17}$)$R^{18}$. More preferably, Q is cyano, halogen, nitro, $NH_2$, phenylsulfonyl or phenylsulfonyl substituted by one to five groups independently selected from $C_1$-$C_4$alkyl and nitro, —$OR^{14}$, —C(═O)N($R^6$)$R^7$, —C(═O)$OR^{7a}$, —C(═O)$R^{13}$, —C($R^{15}$)($R^{16}$)N($R^{17}$)$R^{18}$, or a heterocycle selected from H1 to H9

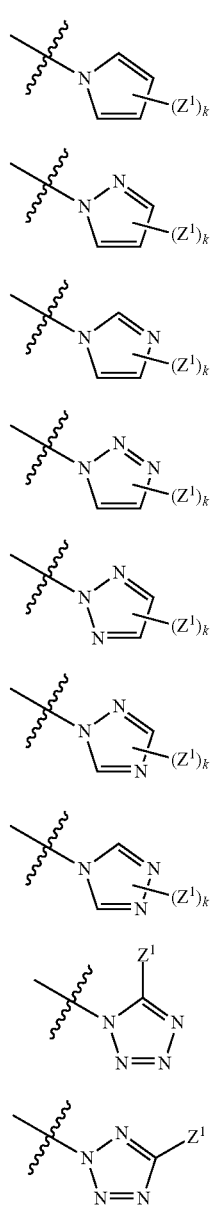

Even more preferably, Q is cyano, halogen, nitro, $NH_2$, $C_1$-$C_8$alkoxy, phenylsulfonyl or phenylsulfonyl substituted by one to five groups independently selected from $C_1$-$C_4$ alkyl and nitro, —C(═O)N($R^6$)$R^7$, —C(═O)$OR^{7a}$, —C(═O)$R^{13}$, —C($R^{15}$)($R^{16}$)N($R^{17}$)$R^{18}$, or a heterocycle selected from H1 to H9.

k is 0, 1, or 2, preferably 0.

$R^6$ is hydrogen, $C_1$-$C_8$alkyl, $C_1$-$C_8$alkoxy, $C_2$-$C_8$alkenyl, $C_2$-$C_8$alkynyl, $C_3$-$C_{10}$cycloalkyl, $C_3$-$C_{10}$cycloalkyl-$C_1$-$C_4$alkylene, $C_1$-$C_8$alkylcarbonyl or $C_1$-$C_8$alkoxycarbonyl. Preferably, $R^6$ is hydrogen, $C_1$-$C_8$alkyl, $C_1$-$C_8$alkoxy, $C_1$-$C_8$alkylcarbonyl, or $C_1$-$C_8$alkoxycarbonyl. More preferably, $R^6$ is hydrogen, methyl, ethyl, methylcarbonyl or methoxycarbonyl, more preferably hydrogen, methyl or ethyl, most preferably hydrogen.

$R^7$ is hydrogen, alkyl or alkyl substituted by one to five $R^8$, alkenyl or alkenyl substituted by one to five $R^8$, alkynyl or alkynyl substituted by one to five $R^8$, $C_3$-$C_{10}$cycloalkyl or $C_3$-$C_{10}$cycloalkyl substituted by one to five $R^9$, $C_3$-$C_{10}$cycloalkyl-$C_1$-$C_4$alkylene or $C_3$-$C_{10}$cycloalkyl-$C_1$-$C_4$alkylene wherein the cycloalkyl moiety is substituted by one to five $R^9$, $C_1$-$C_8$alkyl-N($R^6$)—C(═O)—$C_1$-$C_4$alkylene, $C_1$-$C_8$haloalkyl-N($R^6$)—C(═O)—$C_1$-$C_4$alkylene, $C_3$-$C_8$cycloalkyl-aminocarbonyl-$C_1$-$C_4$alkylene, $C_1$-$C_6$alkyl-O—N═CH—, $C_1$-$C_6$haloalkyl-O—N═CH—, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein each heterocyclyl moiety contains one or more ring members independently selected from O, N, C═O, C═N—$OR^{12}$, N—$R^{12}$, S, SO, $SO_2$, S═N—$R^{12}$ and SO═N—$R^{12}$, aryl or aryl substituted by one to five $R^{10}$, heterocyclyl or heterocyclyl substituted by one to five $R^{10}$ and wherein each heterocyclyl moiety contains one or more ring members independently selected from O, N, C═O, C═N—$OR^{12}$, N—$R^{12}$, S, SO, $SO_2$, S═N—$R^{12}$ and SO═N—$R^{12}$. Preferably, $R^7$ is hydrogen, $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein each heterocyclyl moiety contains one or more ring members independently selected from O, N, C═O, C═N—$OR^{12}$, N—$R^{12}$, S, SO, $SO_2$, S═N—$R^{12}$ and SO═N—$R^{12}$, aryl or aryl substituted by one to five $R^{10}$, heterocyclyl or heterocyclyl substituted by one to five $R^{10}$ and wherein each heterocyclyl moiety contains one or more ring members independently selected from O, N, C═O, C═N—$OR^{12}$, N—$R^{12}$, S, SO, $SO_2$, S═N—$R^{12}$ and SO═N—$R^{12}$, $C_1$-$C_8$alkyl-N($R^6$)—C(═O)—$C_1$-$C_4$ alkylene, $C_1$-$C_8$haloalkyl-N($R^6$)—C(═O)—$C_1$-$C_4$alkylene, $C_3$-$C_8$cycloalkylaminocarbonyl-$C_1$-$C_4$alkylene, $C_1$-$C_6$alkyl-O—N═CH—, or $C_1$-$C_6$haloalkyl-O—N═CH—. More preferably, $R^7$ is hydrogen, $C_1$-$C_8$alkyl, $C_1$-$C_8$haloalkyl, phenyl-$C_1$-$C_6$alkylene or phenyl-$C_1$-$C_6$alkylene wherein the phenyl moiety is substituted by one to five $R^{10}$, pyridyl-$C_1$-$C_6$alkylene or pyridyl-$C_1$-$C_6$alkylene wherein the pyridyl moiety is substituted by one to four $R^{10}$, thiazolyl-$C_1$-$C_6$alkylene or thiazolyl-$C_1$-$C_6$alkylene wherein the thiazolyl moiety is substituted by one or two $R^{10}$, phenyl or phenyl substituted by one to five $R^{10}$, pyridyl or pyridyl substituted by one to four $R^{10}$, thiazolyl or thiazolyl substituted by one or two $R^{10}$, $C_3$-$C_6$cycloalkyl or $C_3$-$C_6$cycloalkyl wherein one ring atom is replaced by O or S, $C_1$-$C_4$alkyl-O—N═CH—, $C_1$-$C_4$haloalkyl-O—N═CH—, $C_1$-$C_4$alkyl-N($R^6$)—C(═O)—$CH_2$—, $C_1$-$C_4$haloalkyl-N($R^6$)—C(═O)—$CH_2$—, or a group of formula (A)

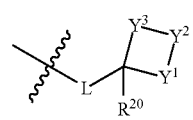

(A)

L is a single bond or $C_1$-$C_6$alkylene;

$Y^1$, $Y^2$ and $Y^3$ are independently of another O, $CR^{21}R^{22}$, C=O, C=N—$OR^{12}$, N—$R^{12}$, S, SO, $SO_2$, S=N—$R^{12}$ or SO=N—$R^{12}$, provided that at least one of $Y^1$, $Y^2$ or $Y^3$ is not $CR^{21}R^{22}$, C=O or C=N—$OR^{12}$. In the group of formula (A), preferably two of $Y^1$, $Y^2$ and $Y^3$ are $CR^{21}R^{22}$, and the other is O, N—$R^{12}$, S, SO, $SO_2$, S=N—$R^{12}$ or SO=N—$R^{12}$, more preferably two of $Y^1$, $Y^2$ and $Y^3$ are $CH_2$ and the other is S, SO or $SO_2$. When L is a bond $Y^1$ and $Y^3$ are preferably $CH_2$ and $Y^2$ is S, SO, $SO_2$, S=N—$R^{12}$ or SO=N—$R^{12}$. When L is alkylene, $Y^1$ is preferably S, SO, $SO_2$, S=N—$R^{12}$ or SO=N—$R^{12}$ and $Y^2$ and $Y^3$ are $CH_2$.

$R^{7a}$ is hydrogen, alkyl or alkyl substituted by one to five $R^8$, alkenyl or alkenyl substituted by one to five $R^8$, alkynyl or alkynyl substituted by one to five $R^8$, cycloalkyl or cycloalkyl substituted by one to five $R^9$, aryl-alkylene or aryl-alkylene wherein the aryl moiety is substituted by one to five $R^{10}$, heteroaryl-alkylene or heteroaryl-alkylene wherein the heteroaryl moiety is substituted by one to five $R^{10}$, aryl or aryl substituted by one to five $R^{10}$, or heteroaryl or heteroaryl substituted by one to five $R^{10}$. Preferably, $R^{7a}$ is hydrogen, $C_1$-$C_{15}$alkyl or $C_1$-$C_{15}$alkyl substituted by one to five $R^8$, $C_2$-$C_{15}$alkenyl or $C_2$-$C_{15}$alkenyl substituted by one to five $R^8$, $C_2$-$C_{15}$alkynyl or $C_2$-$C_{15}$alkynyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heteroaryl-$C_1$-$C_6$alkylene or heteroaryl-$C_1$-$C_6$alkylene wherein the heteroaryl moiety is substituted by one to five $R^{10}$, or heteroaryl or heteroaryl substituted by one to five $R^{10}$. More preferably $R^{7a}$ is hydrogen, $C_1$-$C_{15}$alkyl, $C_1$-$C_{15}$haloalkyl $C_2$-$C_{15}$alkenyl, $C_2$-$C_{15}$haloalkenyl, $C_2$-$C_{15}$alkynyl, $C_2$-$C_{15}$haloalkynyl, phenyl-$C_1$-$C_4$alkylene or phenyl-$C_1$-$C_4$alkylene wherein the phenyl moiety is substituted by one to five halogen, pyridyl-$C_1$-$C_4$alkyl or pyridyl-$C_1$-$C_4$alkyl wherein the pyridyl moiety is substituted by one to four halogen, pyridyl or pyridyl substituted by one to four $R^{10}$, most preferably $R^{7a}$ is $C_1$-$C_{15}$alkyl, $C_1$-$C_{15}$haloalkyl, $C_2$-$C_{15}$alkenyl, $C_2$-$C_{15}$haloalkenyl, pyridyl or benzyl.

$R^{7b}$ is hydrogen, alkyl, haloalkyl, alkenyl, haloalkenyl, alkynyl, haloalkynyl cycloalkyl, halocycloalkyl, alkylcarbonyl, haloalkylcarbonyl, alkoxycarbonyl, haloalkoxycarbonyl, or benzyl, more preferably $R^{7b}$ is hydrogen, $C_1$-$C_{15}$alkyl, $C_3$-$C_{15}$haloalkyl, $C_2$-$C_{15}$alkenyl, $C_2$-$C_{15}$haloalkenyl, $C_2$-$C_{15}$alkynyl, $C_2$-$C_{15}$haloalkynyl, $C_3$-$C_{10}$cycloalkyl, $C_1$-$C_{15}$alkylcarbonyl or $C_1$-$C_{15}$alkoxycarbonyl; most preferably $R^{7b}$ is $C_1$-$C_{15}$alkyl, $C_1$-$C_{15}$haloalkyl, $C_2$-$C_{15}$ alkenyl or $C_2$-$C_{15}$haloalkenyl.

Each $R^8$ is independently halogen, cyano, nitro, hydroxy, $NH_2$, mercapto, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylamino, $C_2$-$C_8$dialkylamino, $C_3$-$C_8$cycloalkylamino, $C_1$-$C_8$alkylcarbonyl, $C_1$-$C_8$alkoxycarbonyl, $C_1$-$C_8$alkylaminocarbonyl, $C_1$-$C_8$dialkylaminocarbonyl, $C_1$-$C_8$haloalkylcarbonyl, $C_1$-$C_8$haloalkoxycarbonyl, $C_1$-$C_8$haloalkylaminocarbonyl, $C_1$-$C_8$halodialkylaminocarbonyl. Preferably, each $R^8$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl. More preferably, each $R^8$ is independently halogen, cyano, nitro, hydroxy, $C_1$-$C_8$alkoxy, $C_1$-$C_8$haloalkoxy, mercapto, $C_1$-$C_8$alkylthio, $C_1$-$C_8$haloalkylthio, more preferably bromo, chloro, fluoro, methoxy, or methylthio, most preferably chloro, fluoro, or methoxy.

Each $R^9$ is independently halogen or $C_1$-$C_8$alkyl. Preferably, each $R^9$ is independently chloro, fluoro or methyl, most preferably each $R^9$ methyl.

Each $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{11}$, or heterocyclyl or heterocyclyl substituted by one to five $R^{11}$. Preferably each $R^{10}$ is independently halogen, cyano, nitro, $C_1$-$C_8$alkyl, $C_1$-$C_8$haloalkyl, $C_1$-$C_8$alkoxy, $C_1$-$C_8$haloalkoxy, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Each $R^4$ and $R^{11}$ is independently halogen, cyano, nitro, $C_1$-$C_8$alkyl, $C_1$-$C_8$haloalkyl, $C_1$-$C_8$alkoxy, $C_1$-$C_8$haloalkoxy or $C_1$-$C_8$alkoxycarbonyl; more preferably each $R^4$ and $R^{11}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably each $R^4$ and $R^{11}$ is independently chloro, fluoro or methyl.

Each $R^{12}$ is independently hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkylene, $C_3$-$C_8$cycloalkyl-$C_1$-$C_8$alkylene where one carbon atom in the cycloalkyl group is replaced by O, S, S(O) or $SO_2$, or $C_3$-$C_8$cycloalkyl-$C_1$-$C_8$haloalkylene, $C_1$-$C_8$hydroxyalkyl, $C_1$-$C_8$alkoxy-$C_1$-$C_8$alkylene, $C_2$-$C_8$alkenyl, $C_2$-$C_8$haloalkenyl, $C_2$-$C_8$alkynyl, $C_2$-$C_8$haloalkynyl, aryl or aryl substituted by one to three $R^{11}$, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$, or $C_1$-$C_4$alkyl-($C_1$-$C_4$alkyl-O—N=)C—$CH_2$—. Preferably, each $R^{12}$ is independently hydrogen, cyano, $C_1$-$C_8$alkyl, $C_1$-$C_8$haloalkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$. More preferably, each $R^{12}$ is independently hydrogen, cyano, $C_1$-$C_8$alkyl, $C_1$-$C_8$haloalkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, phenyl-$C_1$-$C_4$alkylene or phenyl-$C_1$-$C_4$alkylene where the phenyl moiety is substituted by one to three $R^{11}$, or pyridyl-$C_1$-$C_4$alkylene or pyridyl-$C_1$-$C_4$alkylene where the pyridyl moiety is substituted by one to three $R^{11}$.

$R^{13}$ is halogen or imidazole, preferably chloro, fluoro or bromo.

Each $R^{14}$ is independently hydrogen, $C_1$-$C_8$alkyl, $C_2$-$C_8$alkenyl, $C_2$-$C_8$alkynyl, $C_3$-$C_{10}$cycloalkyl, $C_1$-$C_6$alkyl- $C_3$-$C_8$cycloalkyl, $C_3$-$C_8$cycloalkyl-$C_1$-$C_6$alkylene, $C_1$-$C_{10}$alkylcarbonyl, $C_1$-$C_8$alkoxycarbonyl, $C_1$-$C_8$alkylsulfonyl, $C_1$-$C_8$haloalkylsulfonyl, or arylsulfonyl or arylsulfonyl substituted by one to five groups independently selected from $C_1$-$C_4$alkyl and nitro; more preferably each $R^{14}$ is independently hydrogen, $C_1$-$C_8$alkyl, phenylsulfonyl or phenylsulfonyl substituted by one to five groups independently selected from $C_1$-$C_4$alkyl and nitro.

$R^{15}$ and $R^{16}$ are each independently hydrogen, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, cyano, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, or $R^{15}$ and $R^{16}$ together with the carbon atom to which they are attached may form a 3 to 6-membered carbocyclic ring. Preferably, $R^{15}$ and $R^{16}$ are each independently hydrogen, $C_1$-$C_{12}$alkyl, $C_1$-$C_{12}$haloalkyl, $C_3$-$C_8$cycloalkyl, $C_3$-$C_8$halocycloalkyl, $C_2$-$C_{12}$alkenyl or $C_2$-$C_{12}$haloalkenyl, $C_2$-$C_{12}$alkynyl, $C_2$-$C_{12}$haloalkynyl cyano, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, or $R^{15}$ and $R^{16}$ together with the carbon atom to which they are attached may form a 3 to 6-membered carbocyclic ring. Preferably, $R^{15}$ and $R^{16}$ are each independently hydrogen, halogen, cyano, $C_1$-$C_4$alkyl or $C_1$-$C_4$haloalkyl.

$R^{17}$ is hydrogen, $NH_2$, hydroxyl, $C_1$-$C_{12}$ alkoxy or $C_1$-$C_{12}$alkoxy substituted by one to five $R^8$, $C_1$-$C_{12}$alkylcarbonylamino or $C_1$-$C_{12}$alkylcarbonylamino wherein the alkyl is substituted by one to five $R^8$, $C_1$-$C_{12}$alkylamino or $C_1$-$C_{12}$alkylamino wherein the alkyl is substituted by one to five $R^8$, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, cyano, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, $C_1$-$C_{12}$alkylcarbonyl or $C_1$-$C_{12}$alkylcarbonyl substituted by one to five $R^8$, $C_1$-$C_{12}$alkoxycarbonyl or $C_1$-$C_{12}$alkoxycarbonyl substituted by one to five $R^8$ or is selected from $CH_2$—$R^{25}$, $C(=O)R^{19}$ and $C(=S)R^{19}$. Preferably, $R^{17}$ is hydrogen, $NH_2$, hydroxyl, $C_1$-$C_{12}$alkoxy, $C_1$-$C_{12}$haloalkoxy, $C_1$-$C_{12}$alkylcarbonylamino, $C_1$-$C_{12}$haloalkylcarbonylamino, $C_1$-$C_{12}$alkylamino, $C_1$-$C_{12}$haloalkylamino, $C_1$-$C_{12}$alkyl, $C_1$-$C_{12}$haloalkyl, $C_3$-$C_8$cycloalkyl, $C_3$-$C_8$halocycloalkyl, cyano, $C_1$-$C_{12}$alkenyl, $C_1$-$C_{12}$haloalkenyl, $C_2$-$C_{12}$alkynyl, $C_2$-$C_{12}$haloalkynyl, $C_1$-$C_{12}$alkylcarbonyl, $C_1$-$C_{12}$haloalkylcarbonyl, $C_1$-$C_8$alkoxycarbonyl, or $C_1$-$C_8$haloalkoxycarbonyl. More preferably, $R^{17}$ is hydrogen, $C_1$-$C_8$alkyl, $C_1$-$C_8$alkoxy, $C_1$-$C_8$alkylcarbonyl, or $C_1$-$C_8$alkoxycarbonyl.

$R^{18}$ is hydrogen, cyano, carbonyl, thiocarbonyl, $C_1$-$C_{12}$alkylcarbonyl or $C_1$-$C_{12}$ alkylcarbonyl substituted by one to five $R^8$, $C_1$-$C_{12}$alkylthiocarbonyl or $C_1$-$C_{12}$alkylthiocarbonyl substituted by one to five $R^8$, $C_1$-$C_{12}$alkylaminocarbonyl or $C_1$-$C_{12}$alkylaminocarbonyl wherein the alkyl is substituted by one to five $R^8$, $C_1$-$C_{12}$alkylaminothiocarbonyl or $C_1$-$C_{12}$alkylaminothiocarbonyl wherein the alkyl is substituted by one to five $R^8$, $C_2$-$C_{24}$ (total carbon number) dialkylaminocarbonyl or $C_2$-$C_{24}$ (total carbon number) dialkylaminocarbonyl wherein one or both alkyl is substituted by one to five $R^8$, $C_2$-$C_{24}$ (total carbon number) dialkylaminothiocarbonyl or $C_2$-$C_{24}$ (total carbon number) dialkylaminothiocarbonyl wherein one or both alkyl is substituted by one to five $R^8$, $C_1$-$C_{12}$alkoxyaminocarbonyl or $C_1$-$C_{12}$alkoxyaminocarbonyl wherein the alkoxy is substituted by one to five $R^8$, $C_1$-$C_{12}$alkoxyaminothiocarbonyl or $C_1$-$C_{12}$alkoxyaminothiocarbonyl wherein the alkoxy is substituted by one to five $R^8$, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, $C_1$-$C_{12}$thioalkoxycarbonyl or $C_1$-$C_{12}$thioalkoxycarbonyl substituted by one to five $R^8$, $C_1$-$C_{12}$thioalkoxythiocarbonyl or $C_1$-$C_{12}$thioalkoxythiocarbonyl substituted by one to five $R^8$, $C_1$-$C_{12}$alkylsulfonyl or $C_1$-$C_{12}$alkylsulfonyl substituted by one to five $R^8$, $C_3$-$C_{12}$cycloalkylcarbonyl or $C_3$-$C_{12}$cycloalkylcarbonyl substituted by one to five $R^9$, $C_2$-$C_{12}$alkenylcarbonyl or $C_2$-$C_{12}$alkenylcarbonyl substituted by one to five $R^8$, $C_2$-$C_{12}$alkynylcarbonyl or $C_2$-$C_{12}$alkynylcarbonyl substituted by one to five $R^8$, $C_3$-$C_{12}$cycloalkyl-$C_1$-$C_{12}$alkylcarbonyl or $C_3$-$C_{12}$cycloalkyl-$C_1$-$C_{12}$alkylcarbonyl substituted by one to five $R^9$, $C_1$-$C_{12}$alkylsulfenyl-$C_1$-$C_{12}$alkylcarbonyl or $C_1$-$C_{12}$alkylsulfenyl-$C_1$-$C_{12}$alkylcarbonyl substituted by one to five $R^8$, $C_1$-$C_{12}$alkylsulfinyl-$C_1$-$C_{12}$alkylcarbonyl or $C_1$-$C_{12}$alkylsulfinyl-$C_1$-$C_{12}$alkylcarbonyl substituted by one to five $R^8$, $C_1$-$C_{12}$ alkylsulfonyl-$C_1$-$C_{12}$alkylcarbonyl or $C_1$-$C_{12}$alkylsulfonyl-$C_1$-$C_{12}$alkylcarbonyl substituted by one to five $R^8$, $C_1$-$C_{12}$alkylcarbonyl-$C_1$-$C_{12}$alkylcarbonyl or $C_1$-$C_{12}$alkylcarbonyl-$C_1$-$C_{12}$alkylcarbonyl substituted by one to five $R^8$, $C_3$-$C_{12}$cycloalkylaminocarbonyl or $C_3$-$C_{12}$cycloalkylaminocarbonyl wherein the cycloalkyl is substituted by one to five $R^9$, $C_2$-$C_{12}$alkenylaminocarbonyl or $C_2$-$C_{12}$alkenylaminocarbonyl wherein the alkenyl is substituted by one to five $R^8$, $C_2$-$C_{12}$alkynylaminocarbonyl or $C_2$-$C_{12}$alkynylaminocarbonyl wherein the alkynyl is substituted by one to five $R^8$, or is selected from $C(=O)R^{19}$ and $C(=S)R^{19}$. Preferably $R^{18}$ is hydrogen, cyano, carbonyl, thiocarbonyl, $C_1$-$C_{12}$alkylcarbonyl, $C_1$-$C_{12}$haloalkylcarbonyl, $C_1$-$C_{12}$alkylthiocarbonyl, $C_1$-$C_{12}$haloalkylthiocarbonyl, $C_1$-$C_{12}$alkylaminocarbonyl, $C_1$-$C_{12}$alkylaminothiocarbonyl, $C_2$-$C_{24}$ (total carbon number) dialkylaminocarbonyl, $C_2$-$C_{24}$ (total carbon number) dialkylaminothiocarbonyl, $C_1$-$C_{12}$alkoxyaminocarbonyl, $C_1$-$C_{12}$alkoxyaminothiocarbonyl, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, $C_1$-$C_{12}$thioalkoxycarbonyl, $C_1$-$C_{12}$thioalkoxythiocarbonyl, $C_1$-$C_{12}$alkylsulfonyl, $C_1$-$C_{12}$haloalkylsulfonyl, $C_3$-$C_{12}$cycloalkylcarbonyl, $C_3$-$C_{12}$halocycloalkylcarbonyl, $C_2$-$C_{12}$alkenylcarbonyl, $C_2$-$C_{12}$haloalkenylcarbonyl, $C_2$-$C_{12}$ alkynylcarbonyl, $C_2$-$C_{12}$haloalkynylcarbonyl, $C_3$-$C_{12}$cycloalkyl-$C_1$-$C_{12}$alkylcarbonyl, $C_3$-$C_{12}$halocycloalkyl-$C_1$-$C_{12}$alkylcarbonyl, $C_2$-$C_{12}$alkylsulfenyl-$C_1$-$C_{12}$alkylcarbonyl, $C_2$-$C_{12}$haloalkylsulfenyl-$C_1$-$C_{12}$alkylcarbonyl, $C_1$-$C_{12}$alkylsulfinyl-$C_1$-$C_{12}$alkyl carbonyl, $C_1$-$C_{12}$haloalkylsulfinyl-$C_1$-$C_{12}$alkylcarbonyl, $C_1$-$C_{12}$alkylsulfonyl-$C_1$-$C_{12}$alkylcarbonyl, $C_1$-$C_{12}$haloalkylsulfonyl-$C_1$-$C_{12}$alkylcarbonyl, $C_1$-$C_{12}$alkylcarbonyl-$C_1$-$C_{12}$alkylcarbonyl, $C_1$-$C_{12}$haloalkylcarbonyl-$C_1$-$C_{12}$alkylcarbonyl, $C_3$-$C_{12}$cycloalkylaminocarbonyl, $C_2$-$C_{12}$alkenylaminocarbonyl, $C_2$-$C_{12}$alkynylaminocarbonyl. More preferably, $R^{18}$ is $C_1$-$C_4$alkylcarbonyl or $C_1$-$C_4$alkylcarbonyl substituted by one to five $R^8$, $C_3$-$C_6$cycloalkylcarbonyl or $C_3$-$C_6$cycloalkylcarbonyl wherein the cycloalkyl is substituted by one to five $R^9$; even more Preferably, $R^{18}$ is $C_1$-$C_4$alkylcarbonyl, $C_1$-$C_4$haloalkylcarbonyl, $C_3$-$C_6$cycloalkylcarbonyl or $C_3$-$C_6$halocycloalkylcarbonyl.

$R^{17}$ and $R^{18}$ together with the nitrogen atom to which they are bound may form a 3- to 6-membered heterocyclic ring which may be substituted by one to five $R^{11}$, or may be substituted with a keto, thioketo or nitroimino group.

$R^{19}$ is aryl or aryl substituted by one to five $R^{11}$, heterocyclyl or heterocyclyl substituted by one to five $R^{11}$. The aryl is preferably phenyl and the heterocyclyl is preferably pyridyl.

$R^{20}$ is hydrogen or $C_1$-$C_8$alkyl.

Each $R^{21}$ and $R^{22}$ is independently hydrogen, halogen, $C_1$-$C_8$alkyl or $C_1$-$C_8$haloalkyl.

Each $Z^1$ is independently halogen, $C_1$-$C_{12}$alkyl or $C_1$-$C_{12}$alkyl substituted by one to five $R^8$, nitro, $C_1$-$C_{12}$alkoxy or $C_1$-$C_{12}$alkoxy substituted by one to five $R^8$, cyano, $C_1$-$C_{12}$alkylsulfinyl, $C_1$-$C_{12}$ alkylsulfonyl, $C_1$-$C_{12}$haloalkylsulfinyl, $C_1$-$C_{12}$haloalkylsulfonyl, hydroxyl or thiol. Preferably each $Z^1$ is independently halogen, cyano, $C_1$-$C_4$alkyl, $C_1$-$C_4$haloalkyl, $C_1$-$C_4$alkoxy, or $C_1$-$C_4$haloalkoxy, more preferably each $Z^1$ is independently hydrogen, halogen, methyl, halomethyl, methoxy or halomethoxy.

Each $W^5$ is independently O or S. Preferably, each $W^5$ is O.

Y and W are preferably independently hydrogen or phenyl, more preferably at least one of Y and W is phenyl, even more preferably both Y and W are phenyl.

Z is preferably $C_1$-$C_8$ alkyl or phenyl-$C_1$-$C_6$alkylene, more preferably $C_1$-$C_8$ alkyl or benzyl.

In one preferred group of compounds
$R^2$ is aryl or aryl substituted by one to five $R^3$, or heteroaryl or heteroaryl substituted by one to five $R^3$;
each $R^3$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkylamino, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^4$, or heterocyclyl or heterocyclyl substituted by one to five $R^4$;
P is P1 or P2

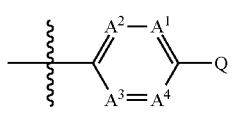

(P1)

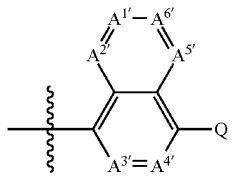

(P2)

$A^1, A^2, A^3, A^4$ are independently of each other C—H, C—$R^5$ or nitrogen, provided that no more than two of $A^1, A^2, A^3, A^4$ are nitrogen;
$A^{1'}, A^{2'}, A^{3'}, A^{4'}, A^{5'}$ and $A^{6'}$ are independently of each other C—H, C—$R^5$ or nitrogen, provided that no more than two of $A^{1'}, A^{2'}, A^{3'}, A^{4'}, A^{5'}$ and $A^{6'}$ are nitrogen;
each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl or $C_1$-$C_8$haloalkylsulfonyl;
Q is hydrogen, halogen, nitro, $NH_2$, cyano, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_3$-$C_8$haloalkynyl, $C_3$-$C_{10}$cycloalkyl, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, arylsulfonyl or arylsulfonyl substituted by one to five groups independently selected from $C_1$-$C_4$ alkyl and nitro, —N($R^6$)$R^{7b}$, —C(=$W^5$)N($R^6$)$R^7$, —C($R^{15}$)($R^{16}$)N($R^{17}$)$R^{18}$, —C(=$W^5$)O$R^{7a}$, —C(=$W^5$)$R^{13}$, —O$R^{14}$, aryl or aryl substituted by one to five $Z^1$, heterocyclyl or heterocyclyl substituted by one to five $Z^1$;
$R^6$ is hydrogen, $C_1$-$C_8$alkyl, $C_1$-$C_8$alkoxy, $C_2$-$C_8$alkenyl, $C_2$-$C_8$alkynyl, $C_3$-$C_{10}$cycloalkyl, $C_3$-$C_{10}$cycloalkyl-$C_1$-$C_4$alkylene, $C_1$-$C_8$alkylcarbonyl or $C_1$-$C_8$alkoxycarbonyl;
$R^7$ is hydrogen, alkyl or alkyl substituted by one to five $R^8$, alkenyl or alkenyl substituted by one to five $R^8$, alkynyl or alkynyl substituted by one to five $R^8$, $C_3$-$C_{10}$cycloalkyl or $C_3$-$C_{10}$cycloalkyl substituted by one to five $R^9$, $C_3$-$C_{10}$cycloalkyl-$C_1$-$C_4$alkylene or $C_3$-$C_{10}$cycloalkyl-$C_1$-$C_4$alkylene wherein the cycloalkyl moiety is substituted by one to five $R^9$, $C_1$-$C_8$alkyl-N($R^6$)—C(=O)—$C_1$-$C_4$alkylene, $C_1$-$C_8$haloalkyl-N($R^6$)—C(=O)—$C_1$-$C_4$alkylene, $C_3$-$C_8$cycloalkyl-aminocarbonyl-$C_1$-$C_4$alkylene, $C_1$-$C_6$ alkyl-O—N=CH—, $C_1$-$C_6$haloalkyl-O—N=CH—, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein the heterocyclyl moiety contains one or more ring members independently selected from O, N, C=O, C=N—O$R^{12}$, N—$R^{12}$, S, SO, $SO_2$, S=N—$R^{12}$ and SO=N—$R^{12}$; aryl or aryl substituted by one to five $R^{10}$, heterocyclyl or heterocyclyl substituted by one to five $R^{10}$ and wherein the heterocyclyl moiety contains one or more ring members independently selected from O, N, C=O, C=N—O$R^{12}$, N—$R^{12}$, S, SO, $SO_2$, S=N—$R^{12}$ and SO=N—$R^{12}$;
$R^{7a}$ is hydrogen, alkyl or alkyl substituted by one to five $R^8$, alkenyl or alkenyl substituted by one to five $R^8$, alkynyl or alkynyl substituted by one to five $R^8$, cycloalkyl or cycloalkyl substituted by one to five $R^9$, aryl-alkylene or aryl-alkylene wherein the aryl moiety is substituted by one to five $R^{10}$, heteroaryl-alkylene or heteroaryl-alkylene wherein the heteroaryl moiety is substituted by one to five $R^{10}$, aryl or aryl substituted by one to five $R^{10}$, or heteroaryl or heteroaryl substituted by one to five $R^{10}$;
$R^{7b}$ is hydrogen, alkyl, haloalkyl, alkenyl, haloalkenyl, alkynyl, haloalkynyl cycloalkyl, halocycloalkyl, alkylcarbonyl, haloalkylcarbonyl, alkoxycarbonyl, haloalkoxycarbonyl, or benzyl;
each $R^8$ is independently halogen, cyano, nitro, hydroxy, $NH_2$, mercapto, $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$ alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylamino, $C_2$-$C_8$dialkylamino, $C_3$-$C_8$cycloalkylamino, $C_1$-$C_8$alkylcarbonyl, $C_1$-$C_8$alkoxycarbonyl, $C_1$-$C_8$alkylamino carbonyl, $C_1$-$C_8$dialkylaminocarbonyl, $C_1$-$C_8$haloalkylcarbonyl, $C_1$-$C_8$haloalkoxycarbonyl, $C_1$-$C_8$haloalkylaminocarbonyl, $C_1$-$C_8$halodialkylaminocarbonyl;
each $R^9$ is independently halogen or $C_1$-$C_8$alkyl;
each $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{11}$, or heterocyclyl or heterocyclyl substituted by one to five $R^{11}$;

each $R^4$ and $R^{11}$ is independently halogen, cyano, nitro, $C_1$-$C_8$alkyl, $C_1$-$C_8$haloalkyl, $C_1$-$C_8$alkoxy, $C_1$-$C_8$haloalkoxy or $C_1$-$C_8$alkoxycarbonyl;

each $R^{12}$ is independently hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkylene, $C_3$-$C_8$cycloalkyl-$C_1$-$C_8$alkylene where one carbon atom in the cycloalkyl group is replaced by O, S, S(O) or $SO_2$, or $C_3$-$C_8$cycloalkyl-$C_1$-$C_8$haloalkylene, $C_1$-$C_8$hydroxyalkyl, $C_1$-$C_8$alkoxy$C_1$-$C_8$alkylene, $C_2$-$C_8$alkenyl, $C_2$-$C_8$haloalkenyl, $C_2$-$C_8$alkynyl, $C_2$-$C_8$haloalkynyl, aryl or aryl substituted by one to three $R^{11}$, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$, or $C_1$-$C_4$alkyl-($C_1$-$C_4$alkyl-O—N=)C—$CH_2$—;

$R^{13}$ is halogen or imidazole;

each $R^N$ is independently hydrogen, $C_1$-$C_8$alkyl, $C_2$-$C_8$alkenyl, $C_2$-$C_8$alkynyl, $C_3$-$C_{10}$cycloalkyl, $C_1$-$C_6$alkyl-$C_3$-$C_8$cycloalkyl, $C_3$-$C_8$cycloalkyl-$C_1$-$C_6$alkylene, $C_1$-$C_{10}$alkylcarbonyl, $C_1$-$C_8$alkoxycarbonyl, $C_1$-$C_8$alkylsulfonyl, $C_1$-$C_8$haloalkylsulfonyl, or arylsulfonyl or arylsulfonyl substituted by one to five groups independently selected from $C_1$-$C_4$alkyl and nitro;

each $R^{15}$ and $R^{16}$ is independently hydrogen, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, cyano, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, or $R^{15}$ and $R^{16}$ together with the carbon atom to which they are attached may form a 3 to 6-membered carbocyclic ring;

$R^{17}$ is hydrogen, $NH_2$, hydroxyl, $C_1$-$C_{12}$alkoxy or $C_1$-$C_{12}$alkoxy substituted by one to five $R^8$, $C_1$-$C_{12}$alkylcarbonylamino or $C_1$-$C_{12}$alkylcarbonylamino wherein the alkyl is substituted by one to five $R^8$, $C_1$-$C_{12}$alkylamino or $C_1$-$C_{12}$alkylamino wherein the alkyl is substituted by one to five $R^8$, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, cyano, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, $C_1$-$C_{12}$alkylcarbonyl or $C_1$-$C_{12}$alkylcarbonyl substituted by one to five $R^8$, $C_1$-$C_{12}$alkoxycarbonyl or $C_1$-$C_{12}$alkoxycarbonyl substituted by one to five $R^8$, or is selected from $CH_2$—$R^{19}$, C(=O)$R^{19}$ and C(=S)$R^{19}$;

$R^{18}$ is hydrogen, cyano, carbonyl, thiocarbonyl, $C_1$-$C_{12}$alkylcarbonyl or $C_1$-$C_{12}$alkylcarbonyl substituted by one to five $R^8$, $C_1$-$C_{12}$alkylthiocarbonyl or $C_1$-$C_{12}$alkylthiocarbonyl substituted by one to five $R^8$, $C_1$-$C_{12}$alkylaminocarbonyl or $C_1$-$C_{12}$alkylaminocarbonyl wherein the alkyl is substituted by one to five $R^8$, $C_1$-$C_{12}$alkylaminothiocarbonyl or $C_1$-$C_{12}$alkylaminothiocarbonyl wherein the alkyl is substituted by one to five $R^8$, $C_2$-$C_{24}$ (total carbon number) dialkylaminocarbonyl or $C_2$-$C_{24}$ (total carbon number) dialkylaminocarbonyl wherein one or both alkyl is substituted by one to five $R^8$, $C_2$-$C_{24}$ (total carbon number) dialkylaminothiocarbonyl or $C_2$-$C_{24}$ (total carbon number) dialkylaminothiocarbonyl wherein one or both alkyl is substituted by one to five $R^8$, $C_1$-$C_{12}$alkoxyaminocarbonyl or $C_1$-$C_{12}$alkoxyaminocarbonyl wherein the alkoxy is substituted by one to five $R^8$, $C_1$-$C_{12}$alkoxyaminothiocarbonyl or $C_1$-$C_{12}$alkoxyaminothiocarbonyl wherein the alkoxy is substituted by one to five $R^8$, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, $C_1$-$C_{12}$thioalkoxycarbonyl or $C_1$-$C_{12}$thioalkoxycarbonyl substituted by one to five $R^8$, $C_1$-$C_{12}$thioalkoxythiocarbonyl or $C_1$-$C_{12}$thioalkoxythiocarbonyl substituted by one to five $R^8$, $C_1$-$C_{12}$alkylsulfonyl or $C_1$-$C_{12}$alkylsulfonyl substituted by one to five $R^8$, $C_3$-$C_{12}$cycloalkylcarbonyl or $C_3$-$C_{12}$cycloalkylcarbonyl substituted by one to five $R^9$, $C_2$-$C_{12}$alkenylcarbonyl or $C_2$-$C_{12}$alkenylcarbonyl substituted by one to five $R^8$, $C_2$-$C_{12}$alkynylcarbonyl or $C_2$-$C_{12}$alkynylcarbonyl substituted by one to five $R^8$, $C_3$-$C_{12}$cycloalkyl-$C_1$-$C_{12}$alkylcarbonyl or $C_3$-$C_{12}$cycloalkyl-$C_1$-$C_{12}$alkylcarbonyl substituted by one to five $R^9$, $C_1$-$C_{12}$alkylsulfenyl-$C_1$-$C_{12}$alkylcarbonyl or $C_1$-$C_{12}$alkylsulfenyl-$C_1$-$C_{12}$alkylcarbonyl substituted by one to five $R^8$, $C_1$-$C_{12}$alkylsulfinyl-$C_1$-$C_{12}$alkylcarbonyl or $C_1$-$C_{12}$ alkylsulfinyl-$C_1$-$C_{12}$alkylcarbonyl substituted by one to five $R^8$, $C_1$-$C_{12}$ alkylsulfonyl-$C_1$-$C_{12}$alkylcarbonyl or $C_1$-$C_{12}$alkylsulfonyl-$C_1$-$C_{12}$alkylcarbonyl substituted by one to five $R^8$, $C_1$-$C_{12}$alkylcarbonyl-$C_1$-$C_{12}$alkylcarbonyl or $C_1$-$C_{12}$alkylcarbonyl-$C_1$-$C_{12}$alkylcarbonyl substituted by one to five $R^8$, $C_3$-$C_{12}$ cycloalkylaminocarbonyl or $C_3$-$C_{12}$cycloalkylaminocarbonyl wherein the cycloalkyl is substituted by one to five $R^9$, $C_2$-$C_{12}$alkenylaminocarbonyl or $C_2$-$C_{12}$alkenylaminocarbonyl wherein the alkenyl is substituted by one to five $R^8$, $C_2$-$C_{12}$alkynylaminocarbonyl or $C_2$-$C_{12}$alkynylaminocarbonyl wherein the alkynyl is substituted by one to five $R^8$, or is selected from C(=O)$R^{19}$ and C(=S)$R^{19}$; or $R^{17}$ and $R^{18}$ together with the nitrogen atom to which they are bound, form a 3- to 6-membered heterocyclic ring which may be substituted by one to five $R^{11}$, or may be substituted with a keto, thioketo or nitroimino group;

$R^{19}$ is aryl or aryl substituted by one to five $R^{11}$, heterocyclyl or heterocyclyl substituted by one to five $R^{11}$;

each $Z^1$ is independently halogen, $C_1$-$C_{12}$alkyl or $C_1$-$C_{12}$alkyl substituted by one to five $R^8$ nitro, $C_1$-$C_{12}$alkoxy or $C_1$-$C_{12}$alkoxy substituted by one to five $R^8$, cyano, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, hydroyl or thiol In another preferred group of compounds $R^2$ is phenyl or phenyl substituted by one to five $R^3$;

Q is cyano, halogen, nitro, $NH_2$, arylsulfonyl or arylsulfonyl substituted by one to five groups independently selected from $C_1$-$C_4$alkyl and nitro, heterocyclyl or heterocyclyl substituted by one to five $Z^1$, —$OR^{14}$, —C(=O)N($R^6$)$R^7$, —C(=O)$OR^{7a}$, —C(=O)$R^{13}$, or —C($R^{15}$)($R^{16}$)N($R^{17}$)$R^{18}$.

In another preferred group of compounds
P is P3

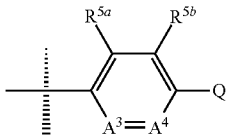
(P3)

$A^3$ and $A^4$ are C—H, or one of $A^3$ and $A^4$ is C—H and the other is nitrogen;

$R^{5a}$ is hydrogen;

$R^{5b}$ is methyl;

or $R^{5a}$ and $R^{5b}$ together form a —CH=CH—CH=CH— bridge;

Q is cyano, halogen, nitro, $NH_2$, phenylsulfonyl or phenylsulfonyl substituted by one to five groups independently selected from $C_1$-$C_4$ alkyl and nitro, —$OR^{14}$, —C(=O)N($R^6$)$R^7$, —C(=O)$OR^{7a}$, —C(=)$R^{13}$, —C($R^{15}$)($R^{16}$)N($R^{17}$)$R^{18}$ or a heterocycle selected from H1 to H9

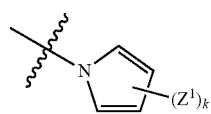 H1

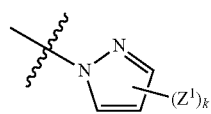 H2

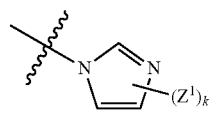 H3

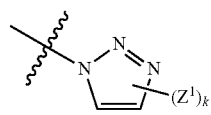 H4

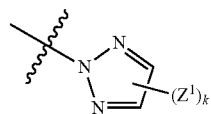 H5

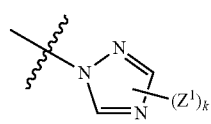 H6

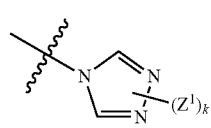 H7

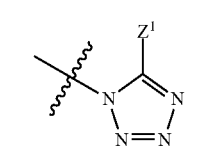 H8

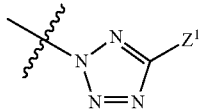 H9 k is 0, 1 or 2;

$R^6$ is hydrogen, $C_1$-$C_8$alkyl, $C_1$-$C_8$alkoxy, $C_1$-$C_8$alkylcarbonyl, or $C_1$-$C_8$alkoxycarbonyl;

$R^7$ is hydrogen, $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, aryl or aryl substituted by one to five $R^{10}$, heterocyclyl or heterocyclyl substituted by one to five $R^{10}$, wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, $C_1$-$C_8$alkyl-N($R^6$)—C(=O)—$C_1$-$C_4$alkylene, $C_1$-$C_8$haloalkyl-N($R^6$)—C(=O)—$C_1$-$C_4$alkylene, $C_3$-$C_8$cycloalkyl-aminocarbonyl-$C_1$-$C_4$alkylene, $C_1$-$C_6$alkyl-O—N=CH—, $C_1$-$C_6$haloalkyl-O—N=CH—;

$R^{7a}$ is $C_1$-$C_{15}$alkyl, $C_1$-$C_{15}$haloalkyl, $C_2$-$C_{15}$ alkenyl, $C_2$-$C_{15}$ haloalkenyl, pyridyl or benzyl.

In another group of preferred compounds

Q is cyano, halogen, nitro, $NH_2$, $C_1$-$C_8$alkoxy, phenylsulfonyl or phenylsulfonyl substituted by one to five groups independently selected from $C_1$-$C_4$ alkyl and nitro, —C(=O)N($R^6$)$R^7$, —C(=O)$OR^{7a}$, —C(=O)$R^{13}$, —C($R^{15}$)($R^{16}$)N($R^{17}$)$R^{18}$, or a heterocycle selected from H1 to H9;

$R^6$ is hydrogen, $C_1$-$C_8$alkyl, $C_1$-$C_8$alkoxy, $C_1$-$C_8$alkylcarbonyl, or $C_1$-$C_8$alkoxycarbonyl;

$R^7$ is hydrogen, $C_1$-$C_8$alkyl, $C_1$-$C_8$haloalkyl, phenyl-$C_1$-$C_6$alkylene or phenyl-$C_1$-$C_6$alkylene wherein the phenyl moiety is substituted by one to five $R^{10}$, pyridyl-$C_1$-$C_6$alkylene or pyridyl-$C_1$-$C_6$alkylene wherein the pyridyl moiety is substituted by one to four $R^{10}$, thiazolyl-$C_1$-$C_6$alkylene or thiazolyl-$C_1$-$C_6$alkylene wherein the thiazolyl moiety substituted by one or two $R^{10}$, phenyl or phenyl substituted by one to five $R^{10}$, pyridyl or pyridyl substituted by one to four $R^{10}$, thiazolyl or thiazolyl substituted by one or two $R^{10}$, $C_3$-$C_6$cycloalkyl or $C_3$-$C_6$cycloalkyl wherein one ring atom is replaced by O or S, $C_1$-$C_4$alkyl-O—N=CH—, $C_1$-$C_4$haloalkyl-O—N=CH—, $C_1$-$C_4$alkyl-N($R^6$)—C(=O)—$CH_2$—, $C_1$-$C_4$haloalkyl-N($R^6$)—C(=O)—$CH_2$—, or a group of formula (A)

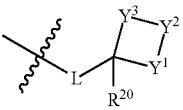
(A)

L is a single bond or $C_1$-$C_6$alkylene;

$Y^1$, $Y^2$ and $Y^3$ are independently of another $CR^{21}R^{22}$, C=O, C=N—$OR^{12}$, N—$R^{12}$, S, SO, $SO_2$, S=N—$R^{12}$ or SO=N—$R^{12}$, provided that at least one of $Y^1$, $Y^2$ or $Y^3$ is not $CR^{21}R^{22}$, C=O or C=N—$OR^{12}$;

each $R^8$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl-;

each $R^{12}$ is independently hydrogen, cyano, $C_1$-$C_8$alkyl, $C_1$-$C_8$haloalkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$;

$R^{15}$ and $R^{16}$ are independently selected from hydrogen, halogen, cyano, $C_1$-$C_4$alkyl, $C_1$-$C_4$haloalkyl;

$R^{17}$ is hydrogen, $C_1$-$C_8$alkyl, $C_1$-$C_8$alkoxy, $C_1$-$C_8$alkylcarbonyl, or $C_1$-$C_8$alkoxycarbonyl;

$R^{18}$ is $C_1$-$C_4$alkylcarbonyl or $C_1$-$C_4$alkylcarbonyl substituted by one to five $R^8$, $C_3$-$C_6$ cycloalkylcarbonyl or $C_3$-$C_6$cycloalkylcarbonyl wherein the cycloalkyl is substituted by one to five $R^9$;

$R^{20}$ is hydrogen or $C_1$-$C_8$alkyl;

each $R^{21}$ and $R^{22}$ is independently hydrogen, halogen, $C_1$-$C_8$alkyl or $C_1$-$C_8$haloalkyl;

each $Z^1$ is independently halogen, cyano, $C_1$-$C_4$alkyl, $C_1$-$C_4$haloalkyl, $C_1$-$C_4$alkoxy, $C_1$-$C_4$haloalkoxy.

In one group of compounds Q is —C(=O)N($R^6$)$R^7$, —C($R^{15}$)($R^{16}$)N($R^{17}$)$R^{18}$ or a heterocycle selected from H1 to H9. These compounds are described in WO2010/020522 (and GB 0910768.1 to which WO2010/020522 claims priority), PCT/EP2010/058207, WO2009/097992 and EP2172448 as being biologically active, namely as insecticides, acaricides and or nematicides. Accordingly in another group of compounds Q is —C(=O)N($R^6$)$R^7$. In another group of compounds Q is —C(=O)N($R^6$)$R^7$ and $R^7$ is a group of formula A. In another group of compounds Q is —C($R^{15}$)($R^{16}$)N($R^{17}$)$R^{18}$. In another group of compounds Q is a heterocycle selected from H1 to H9. In another group of compounds Q is halogen, $C_1$-$C_8$alkoxy, $C_1$-$C_8$alkylsulfonyloxy, $C_1$-$C_8$haloalkylsulfonyloxy, —C(=O)O$R^{7a}$ or —C(=O)$R^{13}$. Compounds in the latter group can be useful as intermediates to make compounds that are biologically active. In one less preferred group of compounds $R^7$ is not a group of formula A.

The compounds of formula I include intermediates that are useful for preparing biologically active compounds. Such intermediates include compounds of formula V

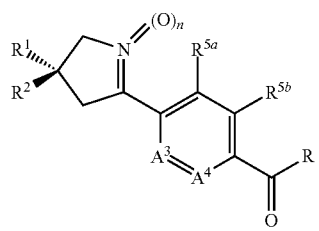

V wherein $R^1$, $R^2$, $A^3$, $A^4$, $R^{5a}$, $R^{5b}$ and n are as defined for the compound of formula I, and R is halogen, OH or $C_1$-$C_{15}$alkoxy. The preferred definitions of $R^1$, $R^2$, $A^3$, $A^4$, $R^{5a}$, $R^{5b}$ and n are as defined for the compound of formula I also apply to the compound of formula V.

Such intermediates also include compounds of formula VI

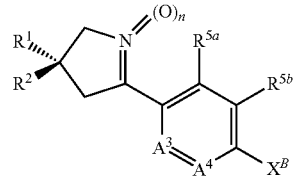

VI wherein $R^1$, $R^2$, $A^3$, $A^4$, $R^{5a}$, $R^{5b}$ and n are as defined for the compound of formula I and $X^B$ is a leaving group such as a halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. $X^B$ is —$N_2^+$Cl$^-$, —$N_2^+$BF$_4^-$, —$N_2^+$Br$^-$, —$N_2^+$PF$_6^-$), phosphonate esters (e.g. —OP(O)(OR)$_2$, wherein R is methyl or ethyl), preferably bromo, iodo, chloro, trifluoromethylsulfoxy, p-toluenesulfoxy, diazonium chloride. The preferred definitions of $R^1$, $R^2$, $A^3$, $A^4$, $R^{5a}$, $R^{5b}$ and n are as defined for the compound of formula I also apply to the compound of formula VI.

Examples of chiral catalysts include chiral cinchona alkaloid derivatives, chiral thiourea derivatives, chiral urea derivatives, chiral aza-crown ether derivatives, chiral metal complexes, chiral amidine and guanidine derivatives, chiral pyrrolidine and imidazolidine derivatives, chiral scandium III complexes, chiral naphthyl phase transfer catalysts, chiral galodinium or strontium catalysts, chiral crown ether derivatives and chiral ligands for alkaline earth metals.

Chiral cinchona alkaloid derivatives are preferred and include alkaloid derivatives of the quaternary ammonium salts, tertiary amine derivatives, urea derivatives, thiourea derivatives and squaramide derivatives.

The term "chiral cinchona alkaloid derivatives" may overlap with the terms "chiral thiourea derivative" and "chiral urea derivative". Accordingly, the term "Chiral cinchona alkaloid derivatives" may in some embodiments exclude chiral thiourea derivatives and chiral urea derivatives. However, unless explicitly indicated the term "Chiral cinchona alkaloid derivatives" will include the relevant chiral thiourea derivatives and chiral urea derivatives.

In one embodiment the chiral catalysts are thiourea derivatives and chiral urea derivatives, in particular those that contain in the molecule a basic nitrogen atom in addition to the two nitrogen atoms of the urea or thiourea moiety, e.g. a primary, secondary or tertiary amine. Examples include chiral cinchona alkaloid thiourea derivatives, chiral cinchona alkaloid urea derivatives, thiourea derivatives of cyclohexanediamine and urea derivatives of cyclohexanediamine. Chiral cinchona alkaloid thiourea derivatives and thiourea derivatives of cyclohexanediamine are preferred.

For the nitromethane addition (process (a)), the preferred chiral catalysts are cinchona alkaloid derivatives, chiral thiourea derivatives and chiral metal complexes. These catalysts include those from groups 1, 2, 3, 4, 5, 7 and 11 below. Particularly preferred catalysts for process (a) are chiral cinchona alkaloid derivatives, particularly cinchona alkaloid derivatives of quaternary ammonium salts, cinchona alkaloid urea derivatives, cinchona alkaloid thiourea derivatives, and cinchona alkaloid squaramide derivatives. Even more preferred are cinchona alkaloid urea derivatives, cinchona alkaloid thiourea derivatives, most preferred being cinchona alkaloid thiourea derivatives.

For the cyanide addition (process (b)), the preferred catalysts are cinchona alkaloid derivatives, chiral ruthenium catalysts as well as gadolinium and strontium catalysts. These catalysts include those from groups 1, 2, 3, 4, 7 and 13. Most preferred catalysts are derivatives of cinchona alkaloid quaternary ammonium salts.

For process (c), the preferred catalysts are chiral cinchona alkaloid derivatives, particularly quaternary ammonium salt derivatives, chiral guanidines and guanidine salts, chiral phase transfer agents as well as alkaline earth metal containing catalysts. These catalysts include those from groups 1, 8, 12 and 15. Catalysts from groups 1 and 15 are preferred, with cinchona alkaloid quaternary ammonium salts most preferred.

For process (d), the preferred are chiral cinchona alkaloid derivatives, particularly cinchona alkaloid urea derivatives, cinchona alkaloid thiourea derivatives, cichona alkaloid squaramide derivatives, thioureas of cyclohexanediamines or of diamines and pyrrolidine derivatives. These catalysts include those from groups 3, 4, 5 and 9.

Examples of cinchona alkaloid quaternary ammonium salt derivatives include compounds of formula VII (group 1)

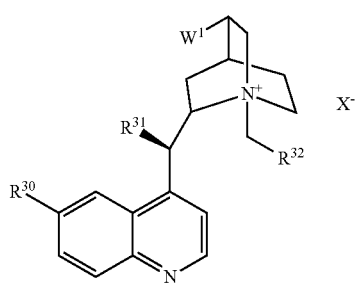

(VII)

wherein
$W^1$ is ethyl or vinyl; $R^{30}$ is hydrogen or $C_1$-$C_4$alkoxy; $R^{31}$ is hydroxyl, $C_1$-$C_4$alkoxy, $C_2$-$C_4$alkenyloxy or optionally substituted benzyloxy; $R^{32}$ is optionally substituted aryl or optionally substituted heteroaryl; X is an anion.

Preferably $W^1$ is vinyl.
Preferably $R^{30}$ is methoxy.
Preferably $R^{31}$ is hydroxyl, $C_1$-$C_4$alkoxy, $C_2$-$C_4$alkenyloxy or benzyloxy, more preferably hydroxyl or benzyloxy, most preferably hydroxyl. In process (c) preferably $R^{31}$ is $C_2$-$C_4$alkenyloxy or benzyloxy and $R^{30}$ is hydrogen or $C_1$-$C_4$alkoxy.

Preferably X is a halogen, more preferably chloride or bromide. Preferably $R^{32}$ is phenyl or phenyl substituted by one to five $R^{33}$, naphthyl or naphthyl substituted by one to five $R^{33}$, anthracenyl or anthracenyl substituted by one to five $R^{33}$, or heteroaryl or heteroaryl substituted by one to four $R^{33}$; more preferably $R^{32}$ is phenyl or phenyl substituted by one to five $R^{33}$, naphthyl or naphthyl substituted by one to five $R^{33}$, anthracenyl or anthracenyl substituted by one to five $R^{33}$, pyrimidinyl or pyrimidinyl substituted by one to three $R^{33}$, or pyridyl or pyridyl substituted by one to four $R^{33}$; more preferably phenyl or phenyl substituted by one to five $R^{33}$, naphthyl or naphthyl substituted by one to five $R^{33}$, anthracenyl or anthracenyl substituted by one to five $R^{33}$, or pyridyl or pyridyl substituted by one to four $R^{33}$; more preferably $R^{32}$ is phenyl or phenyl substituted by one to five $R^{33}$, anthracenyl or anthracenyl substituted by one to five $R^{33}$, or pyridyl or pyridyl substituted by one to four $R^{33}$; even more preferably $R^{32}$ is phenyl or phenyl substituted by one to five substituents independently selected from halogen, methyl and methoxy, anthracenyl or anthracenyl substituted by one to five substituents independently selected from halogen, methyl and methoxy, pyridyl or pyridyl substituted by one to four halogen atoms, or group B

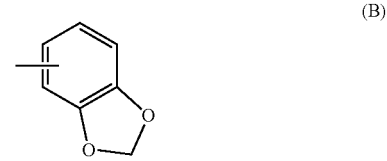

(B)

or group B substituted by one to four substituents independently selected from halogen, methyl and methoxy, even more preferably phenyl substituted by one to five substituents independently selected from halogen methyl and methoxy, anthracenyl or anthracenyl substituted by one to five substituents independently selected from halogen, methyl and methoxy or pyridyl or pyridyl substituted by one to four halogen atoms, even more preferably phenyl substituted by one to five substituents independently selected from halogen methyl and methoxy or anthracenyl. Each $R^{33}$ is independently halogen, cyano, nitro, $C_1$-$C_8$alkyl, $C_1$-$C_8$haloalkyl, $C_1$-$C_8$alkoxy, $C_1$-$C_8$haloalkoxy, $C_3$-$C_8$cycloalkyl, phenyl or phenyl substituted by one to five halogen, and wherein two $R^{33}$ substituents on adjacent carbon atoms may together form a partially saturated 5-7 membered ring containing one or two heteroatoms independently selected from O, N($R^{34}$) and S; and each $R^{34}$ is independently hydrogen or $C_1$-$C_4$ alkyl. Preferably each $R^{33}$ is independently halogen, cyano, nitro, $C_1$-$C_4$alkyl, $C_1$-$C_4$haloalkyl, $C_1$-$C_4$alkoxy, or $C_1$-$C_4$haloalkoxy, and wherein any two $R^{33}$ substituents on adjacent carbon atoms may together form a partially saturated 5 membered ring containing one or two O atoms, more preferably each $R^{33}$ is independently halogen, methyl, halomethyl, methoxy or halomethoxy, and wherein any two $R^{33}$ substituents on adjacent carbon atoms may together form a partially saturated 5 membered ring containing one or two O atoms, more preferably each $R^{33}$ is independently halogen, methyl or methoxy, most preferably each $R^{33}$ is independently fluorine, methyl or methoxy.

Examples include

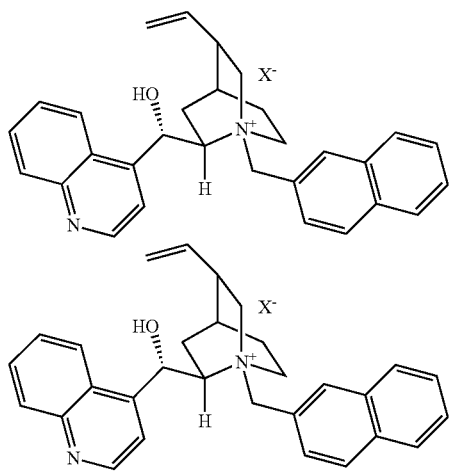

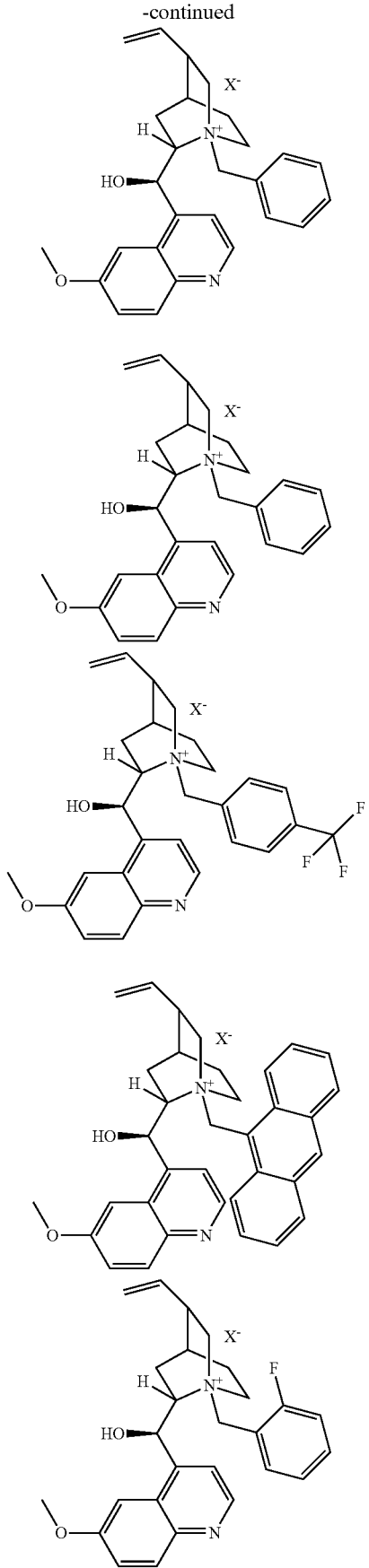
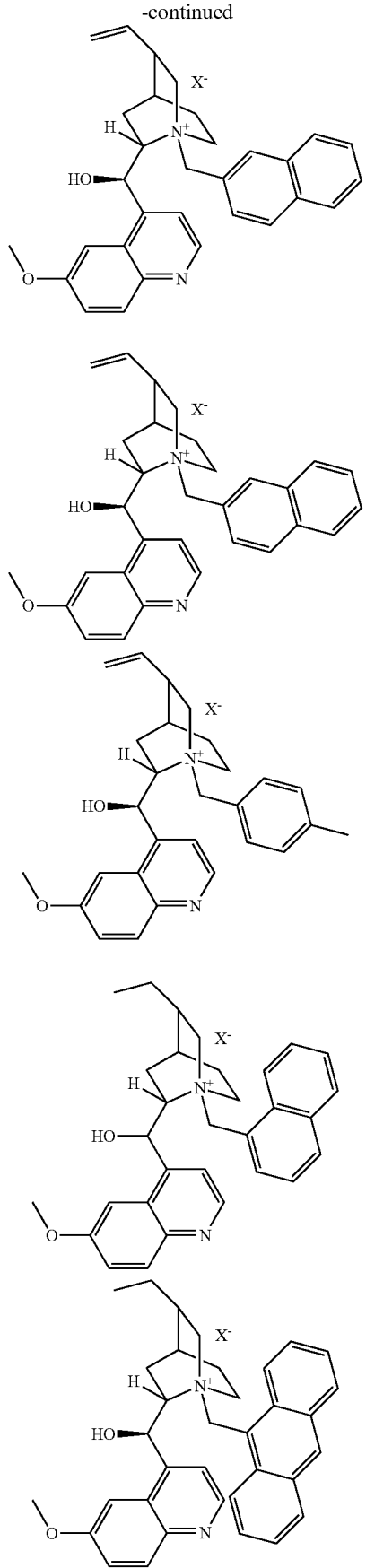

-continued
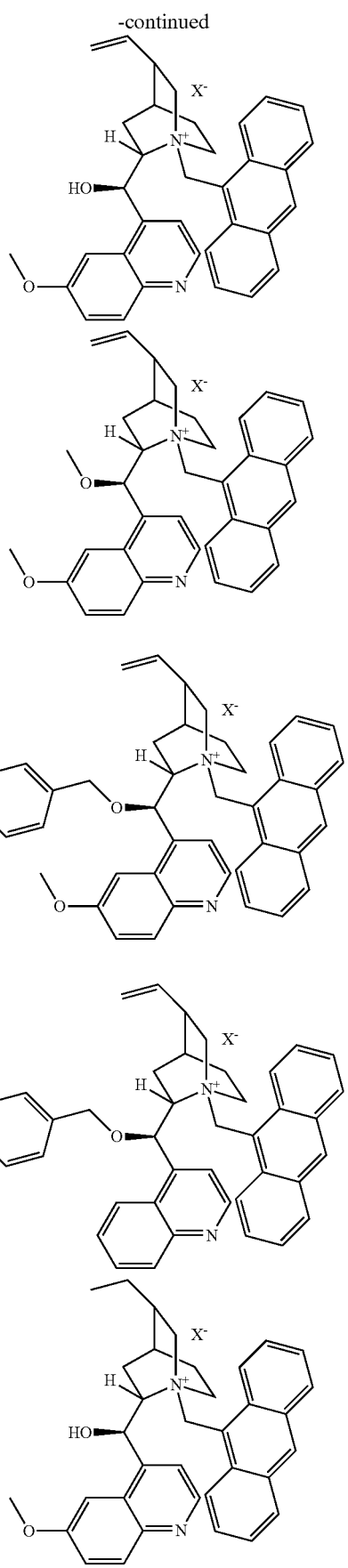
-continued
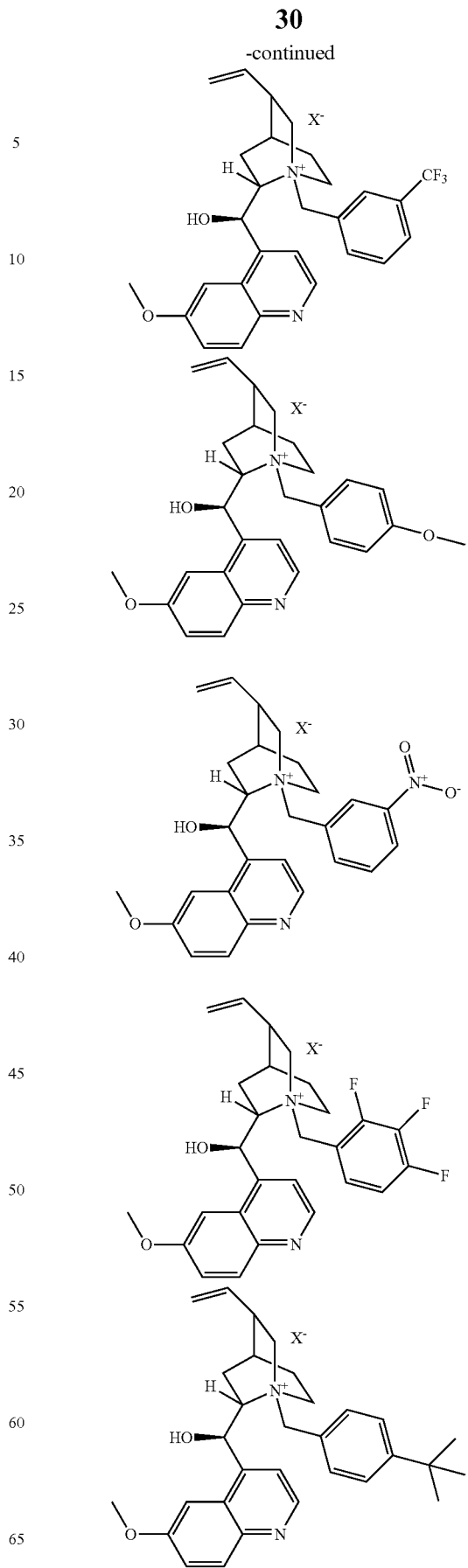

31
-continued
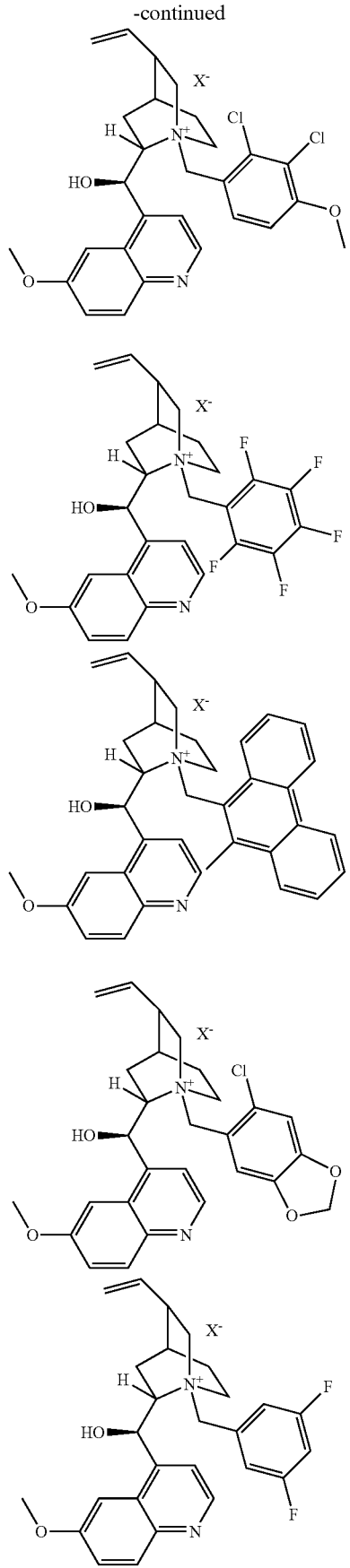
32
-continued
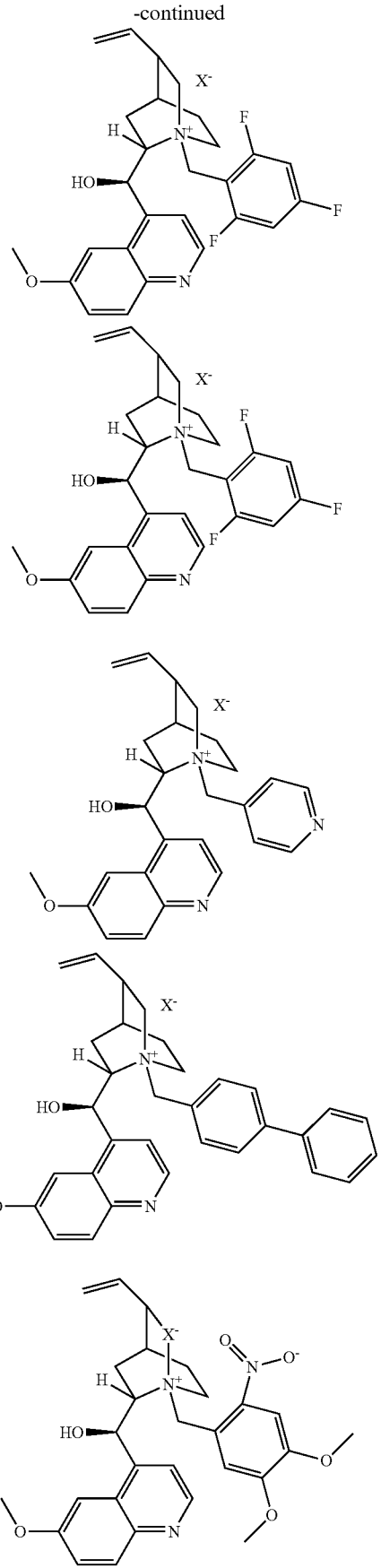

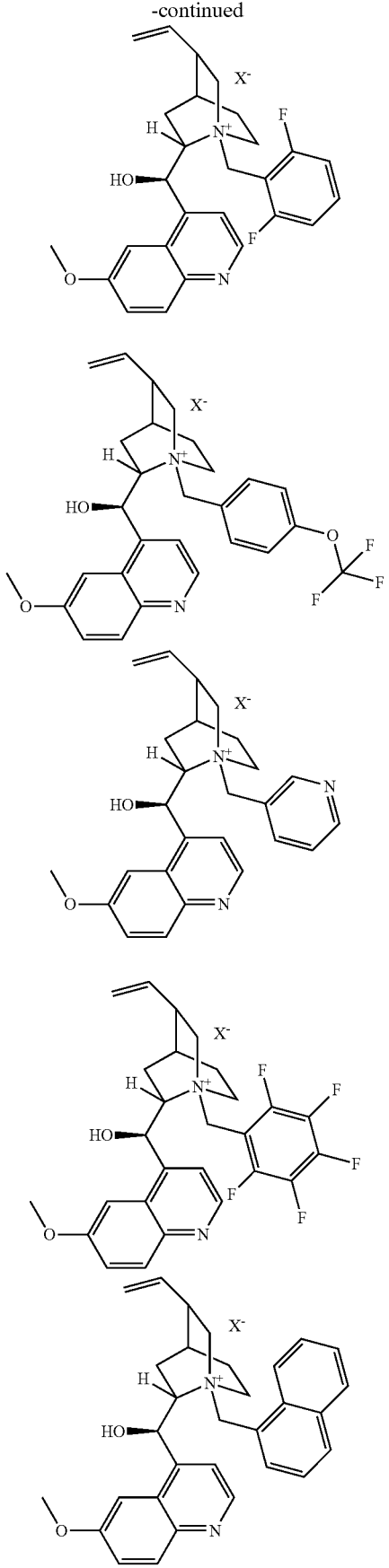
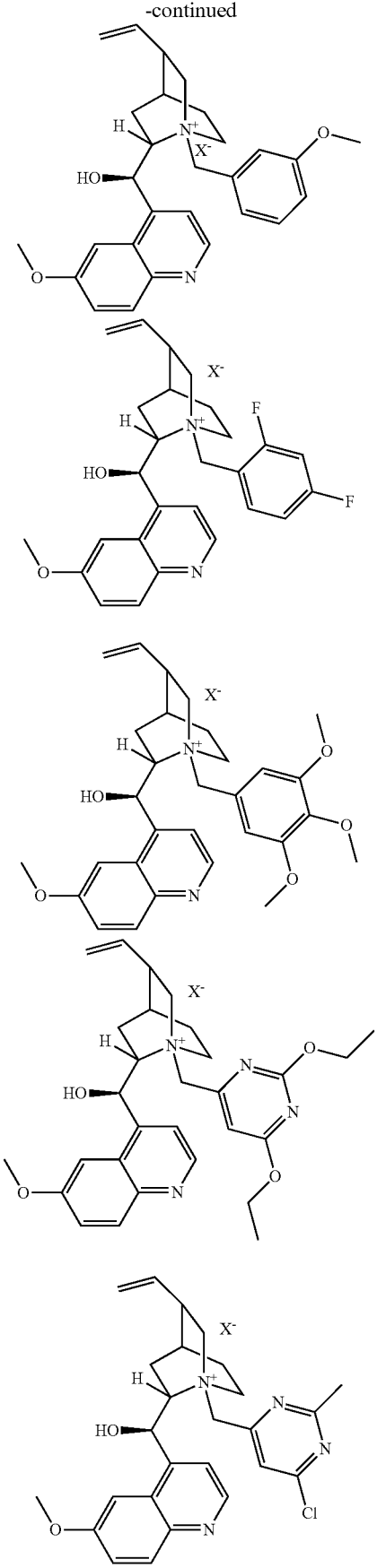

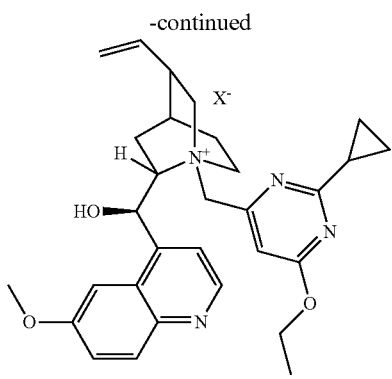

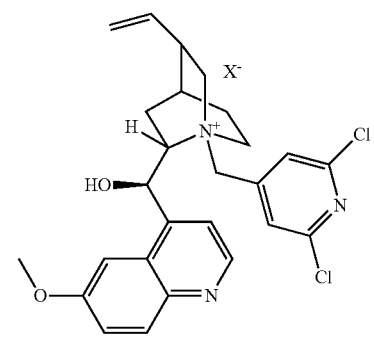

wherein X is an anion, preferably halogen, more preferably chloride or bromide.

Examples of cinchona alkaloid quaternary ammonium salt derivatives are described for example in Arai et al., *Tet. Lett.* 1999, 4215; S. Colonna, H. Hiemstra, H. Wynberg, *J. Chem. Soc. Chem. Commun.* 1978, 238; E. J. Corey, F. Y. Zhang, *Org. Lett.* 2000, 2, 4257; D. Y. Kim, S. C. Huh, *Tetrahedron* 2001, 57, 8933; M. Hua, H. Cui, L. Wang, J. Nie, J. Ma, *Angew. Chem.* 2010, 122, 2832; *Angew. Chem. Int. Ed.* 2010; and T. Ooi, K. Maruoka, *Acc. Chem. Res.* 2004, 37, 526

Examples of cinchona alkaloid tertiary amine derivatives include compounds of formula VIII (group 2)

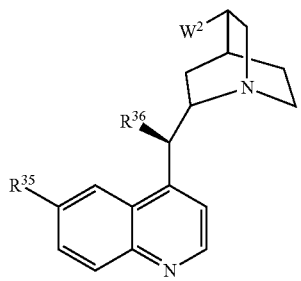

(VIII)

$W^2$ is ethyl or vinyl; $R^{35}$ is hydrogen or $C_1$-$C_4$alkoxy; $R^{36}$ is hydroxyl, $C_1$-$C_4$alkoxy, $C_2$-$C_4$alkenyloxy or optionally substituted benzyloxy.

Preferably $W^2$ is vinyl.

Preferably $R^{35}$ is methoxy.

Preferably $R^{36}$ is hydroxyl, $C_1$-$C_4$alkoxy, $C_2$-$C_4$alkenyloxy or benzyloxy, most preferably hydroxyl.

Examples include:

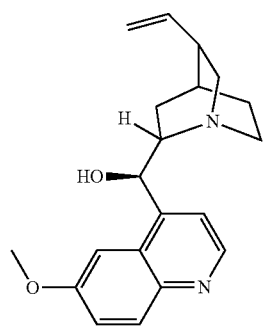 [SMILES: C=CC1CN2CCC1CC2[C@H](O)c1ccnc2ccc(OC)cc12]

as described in A. Latvala, S. Stanchev, A. Linden, M. Hesse, *Tet. Asym.* 1993, 2, 173.

Examples of cinchona alkaloid urea and thiourea derivatives include compounds of formula IX (group 3)

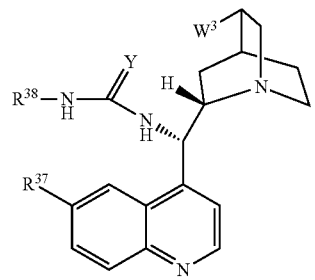

(IX)

Y is S or O, $W^3$ is ethyl or vinyl; $R^{37}$ is hydrogen or $C_1$-$C_4$alkoxy; $R^{38}$ is optionally substituted aryl or optionally substituted $C_3$-$C_{10}$cycloalkyl.

Preferably Y is S.

Preferably $W^3$ is vinyl or ethyl.

Preferably $R^{37}$ is methoxy.

Preferably $R^{38}$ is phenyl optionally substituted by one to five $R^{39}$ or $C_5$-$C_6$cycloalkyl optionally substituted by $R^{40}$, more preferably phenyl optionally substituted by one to five $R^{39}$.

$R^{39}$ is halogen, cyano, $C_1$-$C_4$alkyl, $C_1$-$C_4$haloalkyl, $C_1$-$C_4$alkoxy, $C_1$-$C_4$haloalkoxy, preferably $C_1$-$C_4$ haloalkyl, more preferably $C_1$-$C_4$haloalkyl.

$R^{40}$ is $NH_2$, halogen, cyano, $C_1$-$C_4$alkyl, $C_1$-$C_4$haloalkyl, $C_1$-$C_4$alkoxy, $C_1$-$C_4$haloalkoxy, preferably $NH_2$.

Examples include

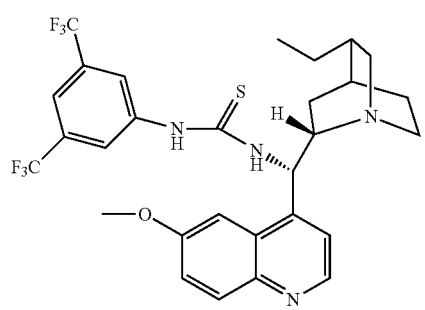

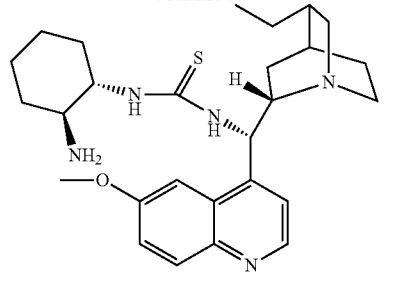

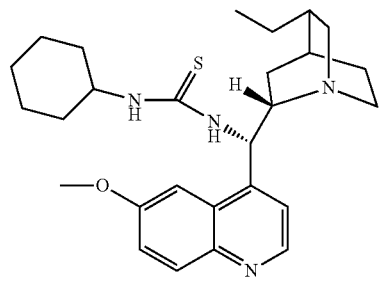

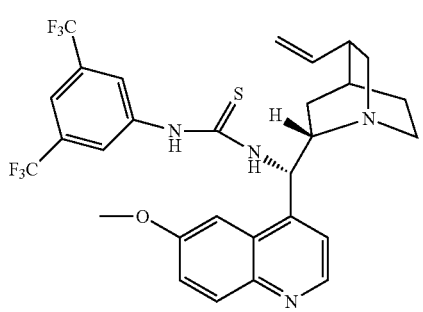

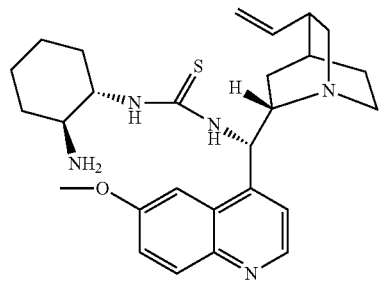

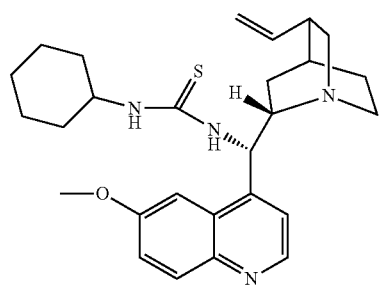

as described in B. Vakulya, S. Varga, A. Csámpai, T. Soós, *Org. Lett.* 2005, 7, 1967; B. Vakulya, S. Varga, T. Soós, *J. Org. Chem.* 2008, 73, 3475; P. Li, Y. Wang, X. Liang, J. Ye, *Chem. Commun.* 2008, 3302; and C. Oliva, A. Silva, F. Paz, J. Calvaleiro, *Synlett,* 2010, 7, 1123-1127.

Examples of squaramide catalysts include compound of formula X (group 4)

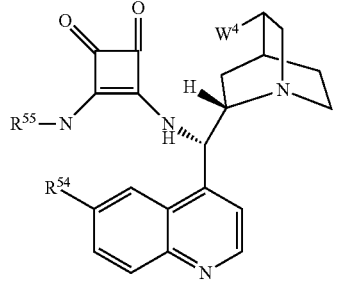

(X)

wherein $W^4$ is ethyl or vinyl; $R^{54}$ is hydrogen or $C_1$-$C_4$alkoxy; $R^{55}$ is optionally substituted aryl.

Preferably $W^4$ is vinyl

Preferably $R^{54}$ is methoxy.

Preferably $R^{55}$ is phenyl optionally substituted by one to five $R^{56}$ or $C_5$-$C_6$cycloalkyl optionally substituted by $R^{40}$.

$R^{56}$ is halogen, cyano, $C_1$-$C_4$alkyl, $C_1$-$C_4$haloalkyl, $C_1$-$C_4$alkoxy, $C_1$-$C_4$haloalkoxy, preferably $C_1$-$C_4$haloalkyl.

Examples include those wherein in the compound of formula X, $R^{54}$ is H or OMe and $R^{55}$ is 4-$CF_3$—$C_6H_4$ or 3,5-$(CF_3)_2$—$C_6H_3$ as described in Yang, W.; Du, D. Org. Lett., 2010, 12 (23), 5450-5453.

Examples of thiourea derivatives of cyclohexanediamine or diamines (group 5) include the following

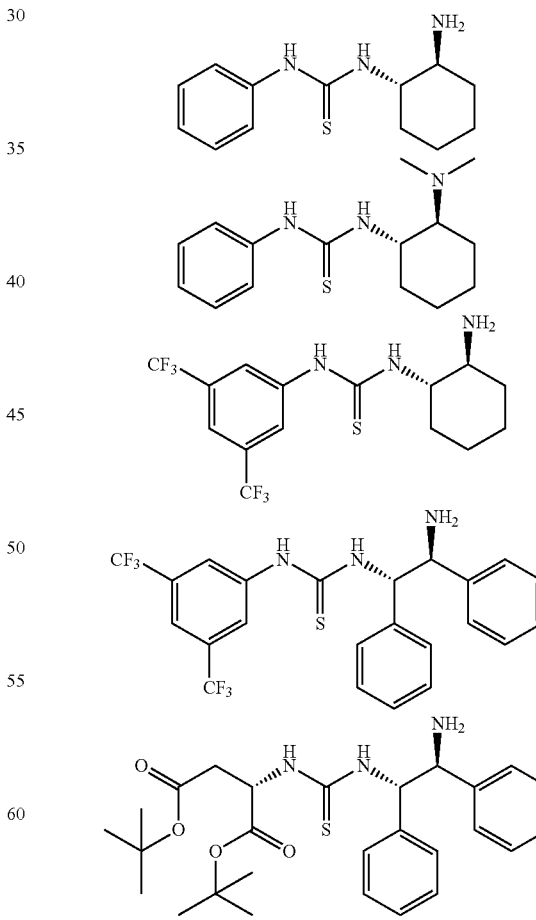

Examples of thiourea derivatives of cyclohexanediamine are described in K. Mei, M. Jin, S. Zhang, P. Li, W. Liu, X. Chen, F. Xue, W. Duan, W. Wang, *Org. Lett.* 2009, 11, 2864, and B. Vakulya, S. Varga, T. Soós, *J. Org. Chem.* 2008, 73, 3475. Examples of thiourea derivatives of diamines are described in He, Tianxiong; Qian, Jing-Ying; Song, Hong-Liang; Wu, Xin-Yan Synlett 2009, 19, 3195-319 and Kokotos, C. G.; Kokotos, G., Advanced Synthesis & Catalysis 2009, 351(9), 1355-1362.

Examples of aza-crown ethers (group 6) include compound of formula XI

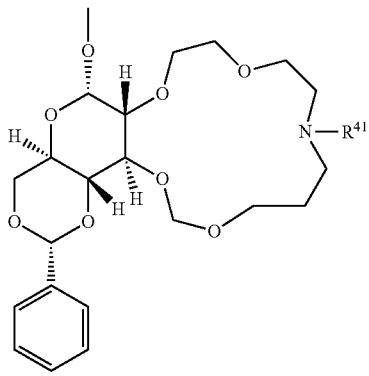

(XI)

$R^{41}$ is hydrogen, $C_1$-$C_{10}$alkyl, $C_1$-$C_{10}$hydroxyalkyl $C_1$-$C_8$alkoxy-$C_1$-$C_8$alkyl, $C_1$-$C_8$alkoxycarbonyl, $C_1$-$C_8$alkyl optionally substituted aryl, aryl-$C_1$-$C_4$alkyl wherein the aryl is optionally substituted, (aryl)$_2$P(O)$C_1$-$C_4$ alkyl wherein each aryl is optionally substituted. Preferably $R^{41}$ is hydrogen, $C_1$-$C_{10}$alkyl, $C_1$-$C_{10}$hydroxyalkyl, $C_1$-$C_8$alkoxy-$C_1$-$C_8$alkyl, $C_1$-$C_8$alkoxycarbonyl-$C_1$-$C_8$alkyl, phenyl, phenyl-$C_1$-$C_4$alkyl, (phenyl)$_2$P(O)$C_1$-$C_4$ alkyl.

Examples of aza crown ethers include those wherein $R^{41}$ is $C_6H_5$, $CH_2C_6H_5$, $CH_3$—$(CH_2)_3$, $CH_3$—$(CH_2)_9$, $CH_2CH_2OH$, $C_6H_{11}$, $CH_2CO_2CH_3$, hydrogen, $CH_2CH_2OCH_3$, $(CH_2)_4P(O)Ph_2$.

Examples of aza-crown ethers are described in P. Bakó, A. Szöllő sy, P. Bombicz, L. Tő ke, *Synlett* 1997, 291 and T. Bakó, P. Bakó, A. Szöllő sy, M. Czugler, G. Keglevich, L. Tő ke, *Tet. Asym.* 2002, 203.

Examples of chiral metal complexes (group 7) include the following

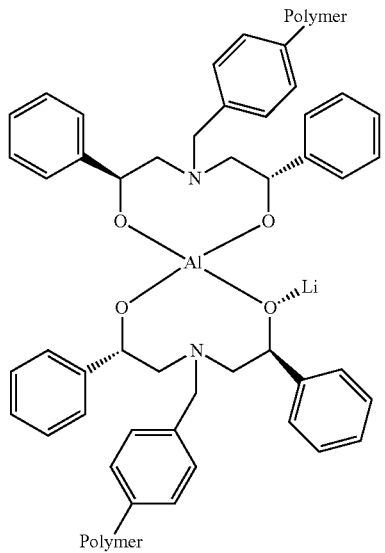

as described in G. Sundararajan, N. Prabagaran, *Org. Lett.* 2001, 3, 389;

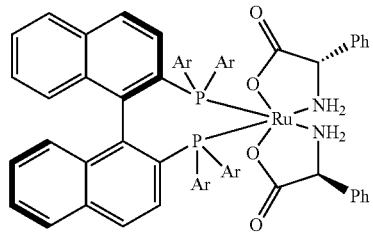

Ar = Ph, p-Tol as described in Kurono, N.; Nii, N.; Sakaguchi, Y.; Uemura, M.; Ohkuma, T. Angew. Chem. Int. Ed. 2011, 50, DOI: 10.1002/anie.201100939

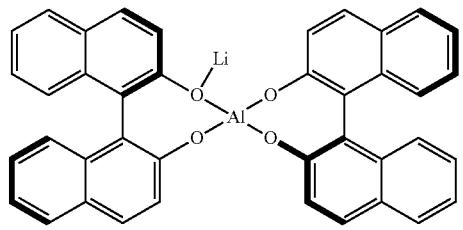

as described in. Keller, N. Veldman, A. L. Spek, B. L. Feringa, *Tetrahedron: Asymmetry* 1997, 8, 3403; LaK$_3$-tris((R)-binaphthoxide)) as described in K. Funabashi, Y. Saida, M. Kanai, T. Arai, H. Sasai, M. Shibasaki, *Tetrahedron Lett.* 1998, 39, 7557; and

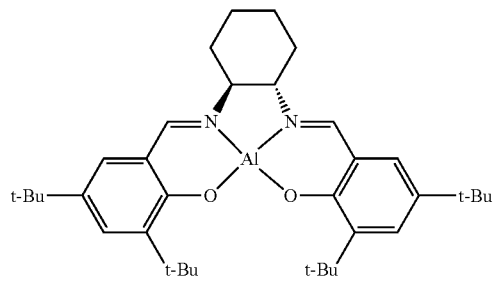

(S,S)-(salen)Al variations thereof include [(S,S)-(salen)Al]$_2$O, (S,S)-(salen)AlMe, (S,S)-(salen)AlCl and are described in M. S. Taylor, D. N. Zalatan, A. M. Lerchner, E. N. Jacobsen, *J. Am. Chem. Soc.* 2005, 127, 1313;

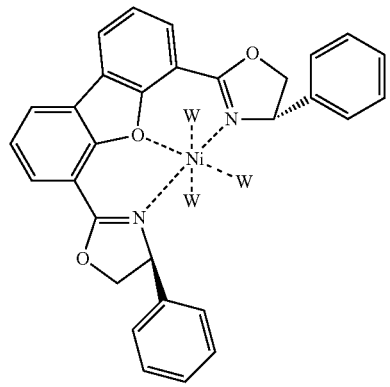

in combination with an achiral amine, e.g. 2,2,6,6-tetramethylpiperidine, as described in K. Itoh, S. Kanemasa, *J. Am. Chem. Soc.* 2002, 124, 13394.

Examples of chiral amidines and guanidines (group 8) include compounds of formula XII

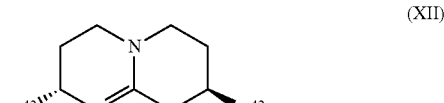

(XII)

wherein each $R^{42}$ is $C(H)Ph_2$, or $CH_2OR^{43}$, wherein $R^{43}$ is t-BuPh$_2$Si, H or benzyl, e.g. as described in A. P. Davis, K. J. Dempsey, *Tetrahedron: Asymmetry* 1995, 6, 2829;

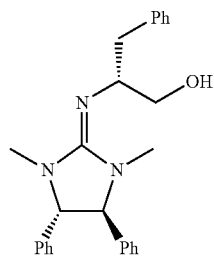 [SMILES: CN1C(=N[C@@H](CO)Cc2ccccc2)N(C)[C@@H](c2ccccc2)[C@@H]1c1ccccc1]

as described in Zhang, G.; Kumamoto, T.; Heima, T.; Ishikawa, T. Tetrahedron Lett. 2010, 51, 3927.

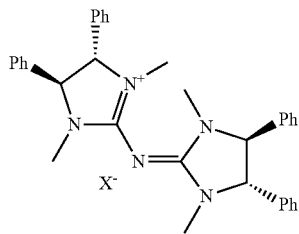

Where X is a halogen or $BF_4$ of $PF_6$, most preferably chloride as described in Ma, T.; Fu, X.; Kee, C. W.; Zong, L.; Pan, Y.; Huang, K.; Tan, C. J. Am. Chem. Soc. 2011, 133, 2828 and

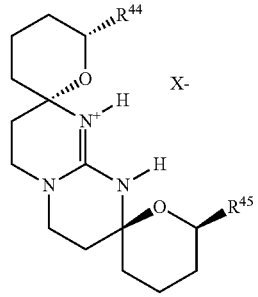

wherein $R^{44}$ and $R^{45}$ are independently $C_1$-$C_4$ alkyl, $C_1$-$C_4$ alkoxy-$C_1$-$C_4$ alkyl, TBDMS-$C_1$-$C_4$ alkyl or TBDPS-$C_1$-$C_4$ alkyl, preferably both $R^{44}$ and $R^{45}$ are either hydroxymethyl, TMDMS-methyl or TBDPS-methyl, and wherein X is an anion, preferably halogen or $BF_4^-$, more preferably chloride or $BF_4^-$, e.g. as described in M. T. Allingham, A. Howard-Jones, P. J. Murphy, D. A. Thomas, P. W. R. Caulkett, *Tetrahedron Lett.* 2003, 44, 8677.

Examples of the pyrrolidine derivatives as chiral catalysts (group 9) include proline, e.g. in combination with trans-2,5-dimethylpiperazine as described in S. Hanessian, V. Pham, *Org. Lett.* 2000, 2, 2975;

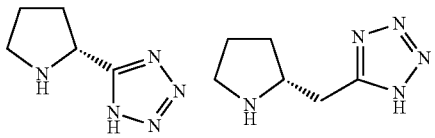

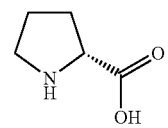

as described in C. E. T. Mitchell, S. E. Brenner and S. V. Ley, *Chem. Commun.*, 2005, 5346 and C. E. T. Mitchell, S. E. Brenner, J. Garcia-Fortanet and S. V. Ley, *Org. Biomol. Chem.*, 2006, 4, 2039;

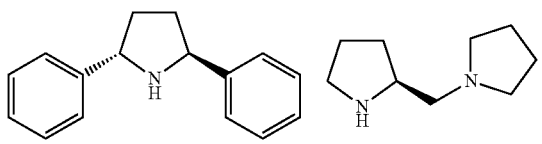

as described in N. Halland, R. G. Hazell, K. A. Jorgensen, *J. Org. Chem.* 2002, 67, 8331;

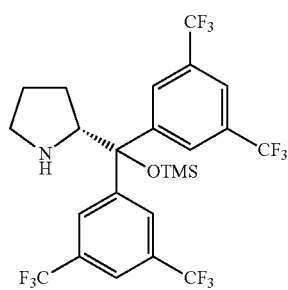

as described in C. Oliva, A. Silva, F. Paz, J. Calvaleiro, *Synlett*, 2010, 7, 1123-1127; and

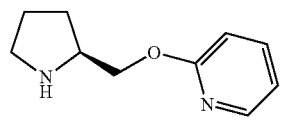 [SMILES: c1ccc(OC[C@@H]2CCCN2)nc1]

as described in Xu, D.; Shi, S.; Wang, Y. European Journal of Organic Chemistry 2009, (28), 4848-4853.

Examples of chiral imidazoline catalysts (group 10) include

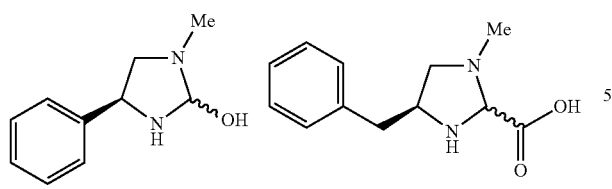

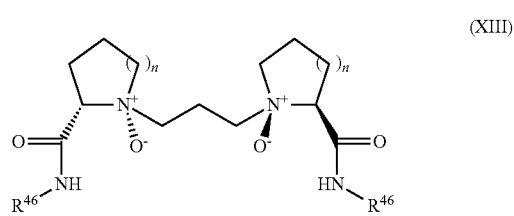
(XIII)

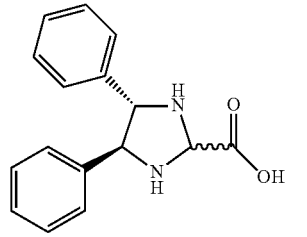

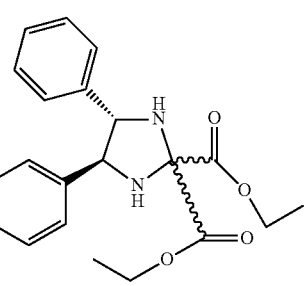
(XIV)

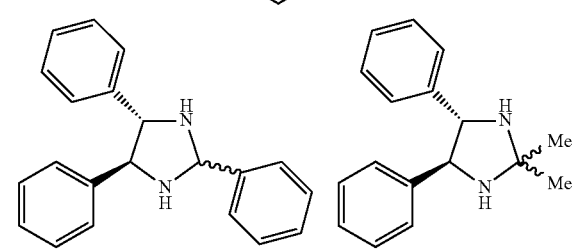

wherein $R^{46}$ and $R^{47}$ are phenyl optionally substituted by one to five halogen, $C_1$-$C_4$ alkyl, $C_1$-$C_4$ haloalkyl, $C_1$-$C_4$ alkoxy, $C_1$-$C_4$ haloalkoxy and wherein n is 1 or 2;

Examples include those wherein n is 1 and $R^{46}$ is 2,6-iPr$_2$C$_6$H$_3$; n is 1 and $R^{46}$ is C$_6$H$_5$; n is 1 and $R^{46}$ is 2-MeC$_6$H$_4$; n is 2 and $R^{46}$ is 2,6-iPr$_2$C$_6$H$_3$; $R^{47}$ is 2,6-iPr$_2$-C$_6$H$_3$; as described in L. Wang, Q. Zhang, X. Zhou, X. Liu, L. Lin, B. Qin, X. Feng, *Chemistry—A European Journal,* 2010, 16, (26), 7696-7699, Chiral binaphthyl phase transfer catalysts (group 12) include compounds of formula XV, XVI, XVII and XVIII

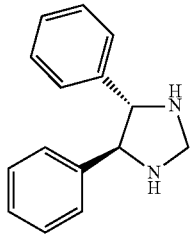

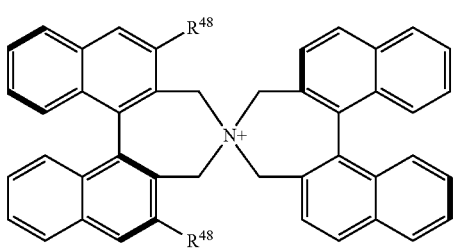
(XV)

as described in N. Halland, R. G. Hazell, K. A. Jørgensen, *J. Org. Chem.* 2002, 67, 8331; and

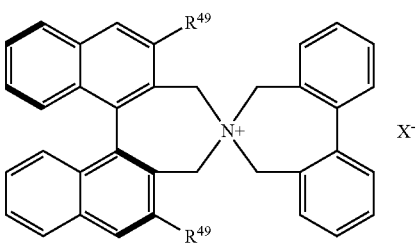
(XVI)

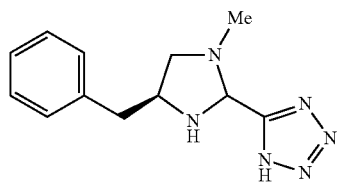 [SMILES: CN1C[C@H](Cc2ccccc2)NC1c1nnn[nH]1]

as described in A. Prieto, N. Halland, K. A. Jørgensen, *Org. Lett.* 2005, 7, 3897.

Examples of chiral N,N'-dioxide-scandium III complexes (group 11) include ligand-Sc(OTf)$_3$ complexes wherein the ligand is a compound of formula XIII or XIV

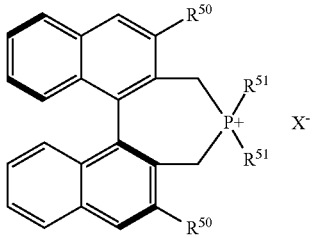
(XVII)

-continued

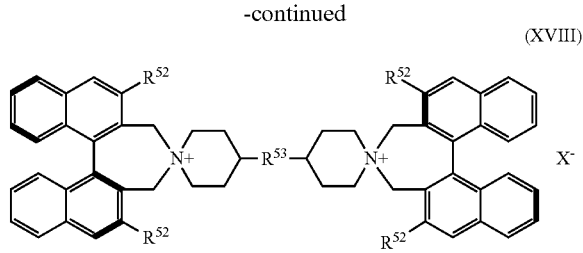
(XVIII)

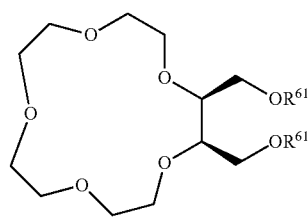

wherein $R^{48}$, $R^{29}$, $R^{50}$ and $R^{52}$ are each independently phenyl or naphthyl optionally substituted by one to five halogen, $C_1$-$C_4$ alkyl, $C_1$-$C_4$ haloalkyl, $C_1$-$C_4$ alkoxy, $C_1$-$C_4$ haloalkoxy; each $R^{51}$ is $C_1$-$C_8$ alkyl or $C_1$-$C_8$ haloalkyl, $R^{53}$ is a bond or $C_1$-$C_8$ alkylene and X is an anion, e.g. a halogen, preferably chlorine or bromine. Examples include those wherein each $R^{48}$ is 3,5-$(CF_3)_2(C_6H_3)$; each $R^{48}$ is 3,4,5-$F_3C_6H_2$; each $R^{49}$ is 3,5-$(CF_3)_2(C_6H_3)$; each $R^{49}$ is 3,4,5-$F_3C_6H_2$; each $R^{50}$ is 3,5-$(CF_3)_2(C_6H_3)$; each $R^{50}$ is 3,4,5-$F_3C_6H_2$; each $R^{51}$ is n-butyl; each $R^{52}$ is H and $R^{53}$ is a bond; each $R^{52}$ is H and $R^{53}$ is ethylene; each $R^{52}$ is H and $R^{53}$ is propylene; each $R^{52}$ is phenyl and $R^{53}$ is a bond; each $R^{52}$ is phenyl and $R^{53}$ is ethylene; each $R^{52}$ is phenyl and $R^{53}$ is propylene; each $R^{52}$ is 3,4,5-$F_3C_6H_2$ and $R^{53}$ is a bond; each $R^{52}$ is 3,4,5-$F_3C_6H_2$ and $R^{53}$ is ethylene; each $R^{52}$ is 3,4,5-$F_3C_6H_2$ and $R^{53}$ is propylene; each $R^{52}$ is ,5-$(CF_3)_2C_6H_2$ and $R^{53}$ is a bond; each $R^{52}$ is ,5-$(CF_3)_2C_6H_2$ and $R^{53}$ is ethylene; each $R^{52}$ is 3,5-$(CF_3)_2C_6H_2$ and $R^{53}$ is propylene; each $R^{48}$ is 2-naphthyl as described in M. Hua, H. Cui, L. Wang, J. Nie, J. Ma, *Angew. Chem.* 2010, 122, 2832 and T. Ooi, K. Maruoka, *Acc. Chem. Res.* 2004, 37, 526.

Examples of ligands for galodinium or strontium catalysis (group 13) include compounds of formula XIX and XX

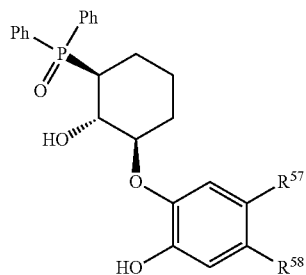
(XIX)

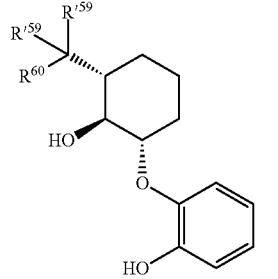
(XX)

wherein $R^{57}$ is CN or F, $R^{58}$ is H or F; each $R^{59}$ is phenyl or p-tolyl; $R^{60}$ is OH, OMe or Oi-Bu as described in Tanaka, Y.; Kanai, M.; Shibasaki, M. *J. Am. Chem. Soc.* 2008, 130, 6072; Tanaka, Y.; Kanai, M.; Shibasaki, M. *J. Am. Chem. Soc.* 2010, 132, 8862.

Examples of crown ether phase transfer catalysis (group 14) include compounds of formula XXI wherein each $R^{61}$ is H or benzyl as described in Dehmlow, D. E.; Sauerbier, C. Liebigs Ann. Chem. 1989, 181-185.

Examples of ligands for alkaline earth metal catalysis (group 15) include

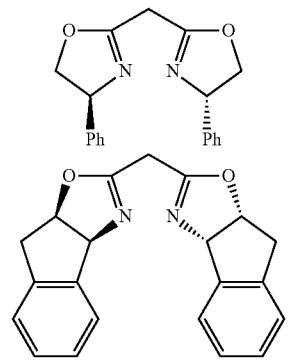

as described in Saito, S.; Tsubogo, T.; Kobayashi, S. *J. Am. Chem. Soc.* 2007, 129, 5364; Tsubogo, T.; Saibo, S.; Seki, K.; Yamashita, Y.; Kobayashi, S. *J. Am. Chem. Soc.* 2008, 130, 13321; Kobayashi, S.; Tsubogo, T.; Saito, S.; Yamashita, Y. *Org. Lett.* 2008, 10, 807

It will be clear to the person skilled in the art that in order to prepare the compounds of the invention with the indicated stereochemistry, the stereochemistry of the compound of formula II must be matched with the corresponding stereochemistry of the catalyst. It is understood that the stereochemistry of the catalysts depicted above is appropriate for a compound of formula IIA:

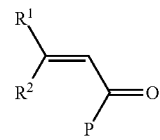
(IIA)

Processes (c) and (d) may also be used to produce racemic mixtures of compounds of formula I e.g. by omitting the chiral catalyst. These novel processes are further aspects of the invention.

In one aspect the invention provides a process for the preparation of the compound of formula Ir

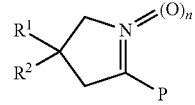
(Ir)

wherein

P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
$R^1$ is chlorodifluoromethyl or trifluoromethyl;
$R^2$ is optionally substituted aryl or optionally substituted heteroaryl;
n is 0 or 1;
comprising
(cr-i) reacting a compound of formula II

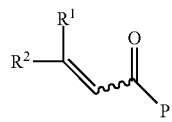

(II)

wherein P, $R^1$ and $R^2$ are as defined for the compound of formula I;
with a compound of formula XXII

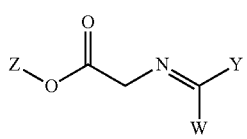

(XXII)

wherein W is hydrogen or optionally substituted aryl, Y is optionally substituted aryl, and Z is optionally substituted alkyl or optionally substituted arylalkylene;
to give a compound of formula XXIIIr

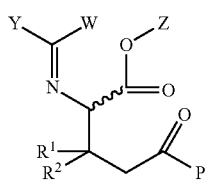

(XXIIIr)

wherein P, $R^1$ and $R^2$ are as defined for the compound of formula I, and Y, W and Z are as defined for the compound of formula XXII;
(cr-ii) treating the compound of formula XXIIIr with a suitable acid or a suitable base to release Y—C(=O)—W and give the compound of formula XXIVr

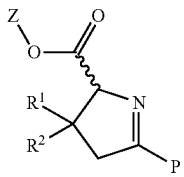

(XXIVr)

wherein P, $R^1$ and $R^2$ are as defined for the compound of formula I and Z is as defined for the compound of formula XXII; and
(cr-iii) decarboxylating the compound XXIVr to give the compound I, wherein n is 0;

In a further aspect the invention provides a process for the preparation of the compound of formula Ir

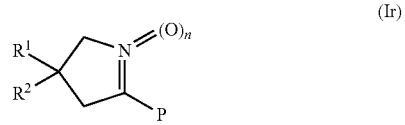

(Ir)

wherein
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
$R^1$ is chlorodifluoromethyl or trifluoromethyl;
$R^2$ is optionally substituted aryl or optionally substituted heteroaryl;
n is 0 or 1;
comprising
(dr-i) reacting a compound of formula XXV

(XXV)

wherein $R^1$ and $R^2$ are as defined for the compound of formula I;
with a compound of formula XXVI

(XXVI)

wherein P is as defined for the compound of formula I;
to give a compound of formula IIIr

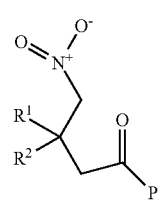

(IIIr)

wherein P, $R^1$ and $R^2$ are as defined for the compound of formula I; and
(dr-ii) reductively cyclising the compound of formula IIIr to give the compound of formula I.

In a further aspect the invention provides a compound of formula XXIIIr

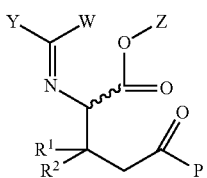

(XXIIIr)

wherein P, R¹ and R² are as defined for the compound of formula I, wherein W is hydrogen or optionally substituted aryl, Y is optionally substituted aryl, and Z is optionally substituted alkyl or optionally substituted arylalkylene. The preferred definitions of R¹, R² and P as defined for the compound of formula I also apply to the compound of formula XXIIIr. Y and W are preferably independently hydrogen or phenyl, more preferably at least one of Y and W is phenyl, even more preferably both Y and W are phenyl. Z is preferably $C_1$-$C_8$ alkyl or phenyl-$C_1$-$C_6$alkylene, more preferably $C_1$-$C_8$ alkyl or benzyl.

In a further aspect the invention provides a compound of formula XXIVr

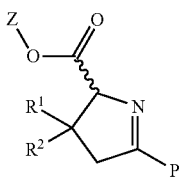

(XXIVr)

wherein P, R¹ and R² are as defined for the compound of formula I, and Z is optionally substituted alkyl or optionally substituted arylalkylene. The preferred definitions of R¹, R² and P as defined for the compound of formula I also apply to the compound of formula XXIV. Z is preferably $C_1$-$C_8$ alkyl or phenyl-$C_1$-$C_6$alkylene, more preferably $C_1$-$C_8$ alkyl or benzyl.

Preferably the compound of formula II is a compound of formula IIA.

Tables 1 to 55 provide preferred compounds of the invention.

Table X represents Table 1 when X is 1, Table 2 when X is 2, Table 3 when X is 3, Table 4 when X is 4, Table 5 when X is 5, Table 6 when X is 6, Table 7 when X is 7, Table 8 when X is 8, Table 9 when X is 9, Table 10 when X is 10, Table 11 when X is 11, Table 12 when X is 12, Table 13 when X is 13, Table 14 when X is 14, Table 15 when X is 15, Table 16 when X is 16, Table 17 when X is 17, Table 18 when X is 18, Table 19 when X is 19, Table 20 when X is 20, Table 21 when X is 21, Table 22 when X is 22, Table 23 when X is 23, Table 24 when X is 24, Table 25 when X is 25, Table 26 when X is 26, Table 27 when X is 27, Table 28 when X is 28, Table 29 when X is 29, Table 30 when X is 30, Table 31 when X is 31, Table 32 when X is 32, Table 33 when X is 33, Table 34 when X is 34, Table 35 when X is 35, Table 36 when X is 36, Table 37 when X is 37, Table 38 when X is 38, Table 39 when X is 39, Table 40 when X is 40, Table 41 when X is 41, Table 42 when X is 42, Table 43 when X is 43, Table 44 when X is 44, Table 45 when X is 45, Table 46 when X is 46, Table 47 when X is 47, Table 48 when X is 48, Table 49 when X is 49, Table 50 when X is 50, Table 51 when X is 51, Table 52 when X is 52, Table 53 when X is 53, Table 54 when X is 54, and Table 55 when X is 55.

| No. | R² | R⁷ |
|---|---|---|
| X.1 | 3,5-dichloro-phenyl | 1,1-dioxo-thietan-3-yl- |
| X.2 | 3,5-dichloro-phenyl | 3-methyl-thietan-3-yl- |
| X.3 | 3,5-dichloro-phenyl | 1-oxo-thietan-3-yl- |
| X.4 | 3,5-dichloro-phenyl | thietan-3-yl- |
| X.5 | 3,5-dichloro-phenyl | 1-oxo-cyclobutan-3-yl |
| X.6 | 3,5-dichloro-phenyl | cyclobutanone O-methyl-oxime-3-yl |
| X.7 | 3,5-dichloro-phenyl | cyclobutanone O-benzyl-oxime-3-yl |
| X.8 | 3,5-dichloro-phenyl | thietan-2-yl-methyl- |
| X.9 | 3,5-dichloro-phenyl | 1-oxo-thietan-2-yl-methyl- |
| X.10 | 3,5-dichloro-phenyl | 1,1-dioxo-thietan-2-yl-methyl- |
| X.11 | 3,5-dichloro-phenyl | 2-pyridylmethyl |
| X.12 | 3,5-dichloro-phenyl | methoxyimino group |
| X.13 | 3,5-dichloro-phenyl | tetrahydrofuran-2-yl |
| X.14 | 3,5-dichloro-phenyl | NH-CH₂CF₃ amide group |
| X.15 | 3,5-dichloro-phenyl | —CH₂—CF₃ |
| X.16 | 3,5-dichloro-phenyl | benzyl |
| X.17 | 3,5-dichloro-phenyl | thiazol-4-ylmethyl |
| X.18 | 3,5-Bis trifluoro methyl-phenyl | 1,1-dioxo-thietan-3-yl- |
| X.19 | 3,5-Bis trifluoro methyl-phenyl | 3-methyl-thietan-3-yl- |
| X.20 | 3,5-Bis trifluoro methyl-phenyl | 1-oxo-thietan-3-yl- |
| X.21 | 3,5-Bis trifluoro methyl-phenyl | thietan-3-yl- |
| X.22 | 3,5-Bis trifluoro methyl-phenyl | 1-oxo-cyclobutan-3-yl |
| X.23 | 3,5-Bis trifluoro methyl-phenyl | cyclobutanone O-methyl-oxime-3-yl |
| X.24 | 3,5-Bis trifluoro methyl-phenyl | cyclobutanone O-benzyl-oxime-3-yl |
| X.25 | 3,5-Bis trifluoro methyl-phenyl | thietan-2-yl-methyl- |
| X.26 | 3,5-Bis trifluoro methyl-phenyl | 1-oxo-thietan-2-yl-methyl- |
| X.27 | 3,5-Bis trifluoro methyl-phenyl | 1,1-dioxo-thietan-2-yl-methyl- |
| X.28 | 3,5-Bis trifluoro methyl-phenyl | 2-pyridylmethyl |
| X.29 | 3,5-Bis trifluoro methyl-phenyl | methoxyimino group |
| X.30 | 3,5-Bis trifluoro methyl-phenyl | tetrahydrofuran-2-yl |

-continued

| No. | R² | R⁷ |
|---|---|---|
| X.31 | 3,5-Bis trifluoro methyl-phenyl | 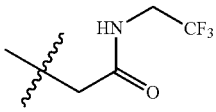 [SMILES: *CC(=O)NCC(F)(F)F] |
| X.32 | 3,5-Bis trifluoro methyl-phenyl | —CH₂—CF₃ |
| X.33 | 3,5-Bis trifluoro methyl-phenyl | benzyl |
| X.34 | 3,5-Bis trifluoro methyl-phenyl | 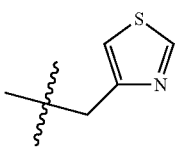 [SMILES: *Cc1cscn1] |
| X.35 | 3,4,5-Trichloro-phenyl | 1,1-dioxo-thietan-3-yl- |
| X.36 | 3,4,5-Trichloro-phenyl | 3-methyl-thietan-3-yl- |
| X.37 | 3,4,5-Trichloro-phenyl | 1-oxo-thietan-3-yl- |
| X.38 | 3,4,5-Trichloro-phenyl | thietan-3-yl- |
| X.39 | 3,4,5-Trichloro-phenyl | 1-oxo-cyclobutan-3-yl |
| X.40 | 3,4,5-Trichloro-phenyl | cyclobutanone O-methyl-oxime-3-yl |
| X.41 | 3,4,5-Trichloro-phenyl | cyclobutanone O-benzyl-oxime-3-yl |
| X.42 | 3,4,5-Trichloro-phenyl | thietan-2-yl-methyl- |
| X.43 | 3,4,5-Trichloro-phenyl | 1-oxo-thietan-2-yl-methyl- |
| X.44 | 3,4,5-Trichloro-phenyl | 1,1-dioxo-thietan-2-yl-methyl- |
| X.45 | 3,4,5-Trichloro-phenyl | 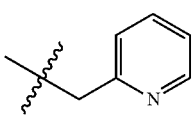 [SMILES: *Cc1ccccn1] |
| X.46 | 3,4,5-Trichloro-phenyl | 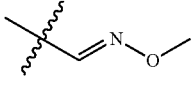 [SMILES: */C=N/OC] |
| X.47 | 3,4,5-Trichloro-phenyl | 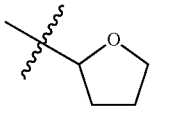 [SMILES: *C1CCCO1] |
| X.48 | 3,4,5-Trichloro-phenyl | 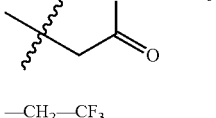 |
| X.49 | 3,4,5-Trichloro-phenyl | —CH₂—CF₃ |
| X.50 | 3,4,5-Trichloro-phenyl | benzyl |
| X.51 | 3,4,5-Trichloro-phenyl | 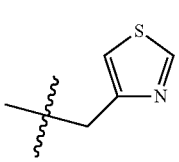 [SMILES: *Cc1cscn1] |
| X.52 | 3,5-dichloro-4-fluoro-phenyl | 1,1-dioxo-thietan-3-yl- |
| X.53 | 3,5-dichloro-4-fluoro-phenyl | 3-methyl-thietan-3-yl- |
| X.54 | 3,5-dichloro-4-fluoro-phenyl | 1-oxo-thietan-3-yl- |
| X.55 | 3,5-dichloro-4-fluoro-phenyl | thietan-3-yl- |
| X.56 | 3,5-dichloro-4-fluoro-phenyl | 1-oxo-cyclobutan-3-yl |
| X.57 | 3,5-dichloro-4-fluoro-phenyl | cyclobutanone O-methyl-oxime-3-yl |
| X.58 | 3,5-dichloro-4-fluoro-phenyl | cyclobutanone O-benzyl-oxime-3-yl |
| X.59 | 3,5-dichloro-4-fluoro-phenyl | thietan-2-yl-methyl- |
| X.60 | 3,5-dichloro-4-fluoro-phenyl | 1-oxo-thietan-2-yl-methyl- |
| X.61 | 3,5-dichloro-4-fluoro-phenyl | 1,1-dioxo-thietan-2-yl-methyl- |
| X.62 | 3,5-dichloro-4-fluoro-phenyl | 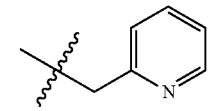 [SMILES: *Cc1ccccn1] |
| X.63 | 3,5-dichloro-4-fluoro-phenyl | 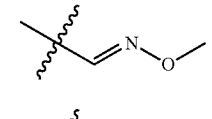 |
| X.64 | 3,5-dichloro-4-fluoro-phenyl | 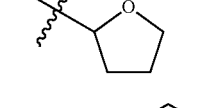 |
| X.65 | 3,5-dichloro-4-fluoro-phenyl | 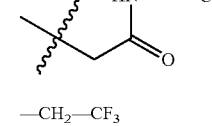 |
| X.66 | 3,5-dichloro-4-fluoro-phenyl | —CH₂—CF₃ |
| X.67 | 3,5-dichloro-4-fluoro-phenyl | benzyl |
| X.68 | 3,5-dichloro-4-fluoro-phenyl | 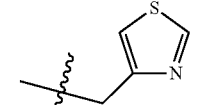 |
| X.69 | 3-chloro-5-trifluoro methyl-phenyl | 1,1-dioxo-thietan-3-yl- |
| X.70 | 3-chloro-5-trifluoro methyl-phenyl | 3-methyl-thietan-3-yl- |
| X.71 | 3-chloro-5-trifluoro methyl-phenyl | 1-oxo-thietan-3-yl- |
| X.72 | 3-chloro-5-trifluoro methyl-phenyl | thietan-3-yl- |
| X.73 | 3-chloro-5-trifluoro methyl-phenyl | 1-oxo-cyclobutan-3-yl |
| X.74 | 3-chloro-5-trifluoro methyl-phenyl | cyclobutanone O-methyl-oxime-3-yl |
| X.75 | 3-chloro-5-trifluoro methyl-phenyl | cyclobutanone O-benzyl-oxime-3-yl |
| X.76 | 3-chloro-5-trifluoro methyl-phenyl | thietan-2-yl-methyl- |
| X.77 | 3-chloro-5-trifluoro methyl-phenyl | 1-oxo-thietan-2-yl-methyl- |
| X.78 | 3-chloro-5-trifluoro methyl-phenyl | 1,1-dioxo-thietan-2-yl-methyl- |
| X.79 | 3-chloro-5-trifluoro methyl-phenyl | 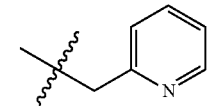 [SMILES: *Cc1ccccn1] |
| X.80 | 3-chloro-5-trifluoro methyl-phenyl | 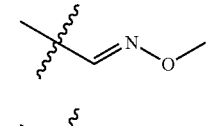 |
| X.81 | 3-chloro-5-trifluoro methyl-phenyl | 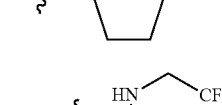 |
| X.82 | 3-chloro-5-trifluoro methyl-phenyl | 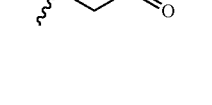 |

-continued

| No. | R² | R⁷ |
|---|---|---|
| X.83 | 3-chloro-5-trifluoro methyl-phenyl | —CH₂—CF₃ |
| X.84 | 3-chloro-5-trifluoro methyl-phenyl | benzyl |
| X.85 | 3-chloro-5-trifluoro methyl-phenyl | (thiazol-4-yl-methyl) |
| X.86 | 3-chloro-5-bromo-phenyl | 1,1-dioxo-thietan-3-yl- |
| X.87 | 3-chloro-5-bromo-phenyl | 3-methyl-thietan-3-yl- |
| X.88 | 3-chloro-5-bromo-phenyl | 1-oxo-thietan-3-yl- |
| X.89 | 3-chloro-5-bromo-phenyl | thietan-3-yl- |
| X.90 | 3-chloro-5-bromo-phenyl | 1-oxo-cyclobutan-3-yl |
| X.91 | 3-chloro-5-bromo-phenyl | cyclobutanone O-methyl-oxime-3-yl |
| X.92 | 3-chloro-5-bromo-phenyl | cyclobutanone O-benzyl-oxime-3-yl |
| X.93 | 3-chloro-5-bromo-phenyl | thietan-2-yl-methyl- |
| X.94 | 3-chloro-5-bromo-phenyl | 1-oxo-thietan-2-yl-methyl- |
| X.95 | 3-chloro-5-bromo-phenyl | 1,1-dioxo-thietan-2-yl-methyl- |
| X.96 | 3-chloro-5-bromo-phenyl | (pyridin-2-yl-methyl) |
| X.97 | 3-chloro-5-bromo-phenyl | (=N-OMe) |
| X.98 | 3-chloro-5-bromo-phenyl | (tetrahydrofuran-2-yl) |
| X.99 | 3-chloro-5-bromo-phenyl | —CH₂—C(=O)—NH—CH₂—CF₃ |
| X.100 | 3-chloro-5-bromo-phenyl | —CH2—CF3 |
| X.101 | 3-chloro-5-bromo-phenyl | benzyl |
| X.102 | 3-chloro-5-bromo-phenyl | (thiazol-4-yl-methyl) |
| X.103 | 3,5-dichloro-phenyl | cyclobutyl |
| X.104 | 3,5-dichloro-phenyl | cyclobutanone O-trifluoroethyl-oxime-3-yl |
| X.105 | 3,5-dichloro-phenyl | (=N-OEt) |
| X.106 | 3,5-dichloro-phenyl | —CH₂—CH₂—S—CH₃ |
| X.107 | 3,5-dichloro-phenyl | —CH₂—CH₂—S(=O)—CH₃ |
| X.108 | 3,5-dichloro-phenyl | —CH₂—CH₂—S(=O)₂—CH₃ |
| X.109 | 3,5-Bis trifluoro methyl-phenyl | cyclobutyl |
| X.110 | 3,5-Bis trifluoro methyl-phenyl | cyclobutanone O-trifluoroethyl-oxime-3-yl |
| X.111 | 3,5-Bis trifluoro methyl-phenyl | (=N-OEt) |
| X.112 | 3,5-Bis trifluoro methyl-phenyl | —CH₂—CH₂—S—CH₃ |
| X.113 | 3,5-Bis trifluoro methyl-phenyl | —CH₂—CH₂—S(=O)—CH₃ |
| X.114 | 3,5-Bis trifluoro methyl-phenyl | —CH₂—CH₂—S(=O)₂—CH₃ |
| X.115 | 3,4,5-Trichloro-phenyl | cyclobutyl |
| X.116 | 3,4,5-Trichloro-phenyl | cyclobutanone O-trifluoroethyl-oxime-3-yl |
| X.117 | 3,4,5-Trichloro-phenyl | (=N-OEt) |
| X.118 | 3,4,5-Trichloro-phenyl | —CH₂—CH₂—S—CH₃ |
| X.119 | 3,4,5-Trichloro-phenyl | —CH₂—CH₂—S(=O)—CH₃ |
| X.120 | 3,4,5-Trichloro-phenyl | —CH₂—CH₂—S(=O)₂—CH₃ |
| X.121 | 3,5-dichloro-4-fluoro-phenyl | cyclobutyl |
| X.122 | 3,5-dichloro-4-fluoro-phenyl | cyclobutanone O-trifluoroethyl-oxime-3-yl |
| X.123 | 3,5-dichloro-4-fluoro-phenyl | (=N-OEt) |

55
-continued

| No. | R² | R⁷ |
|---|---|---|
| X.124 | 3,5-dichloro-4-fluoro-phenyl | –CH₂CH₂SCH₃ |
| X.125 | 3,5-dichloro-4-fluoro-phenyl | –CH₂CH₂S(O)CH₃ |
| X.126 | 3,5-dichloro-4-fluoro-phenyl | –CH₂CH₂S(O)₂CH₃ |
| X.127 | 3-chloro-5-trifluoro methyl-phenyl | cyclobutyl |
| X.128 | 3-chloro-5-trifluoro methyl-phenyl | cyclobutanone O-trifluoroethyl-oxime-3-yl |
| X.129 | 3-chloro-5-trifluoro methyl-phenyl | –CH=N–OCH₂CH₃ |
| X.130 | 3-chloro-5-trifluoro methyl-phenyl | –CH₂CH₂SCH₃ |
| X.131 | 3-chloro-5-trifluoro methyl-phenyl | –CH₂CH₂S(O)CH₃ |
| X.132 | 3-chloro-5-trifluoro methyl-phenyl | –CH₂CH₂S(O)₂CH₃ |
| X.133 | 3-chloro-5-bromo-phenyl | cyclobutyl |
| X.134 | 3-chloro-5-bromo-phenyl | cyclobutanone O-trifluoroethyl-oxime-3-yl |
| X.135 | 3-chloro-5-bromo-phenyl | –CH=N–OCH₂CH₃ |
| X.136 | 3-chloro-5-bromo-phenyl | –CH₂CH₂SCH₃ |
| X.137 | 3-chloro-5-bromo-phenyl | –CH₂CH₂S(O)CH₃ |
| X.138 | 3-chloro-5-bromo-phenyl | –CH₂CH₂S(O)₂CH₃ |

Table 1

Table 1 discloses compounds 1.1 to 1.138 of the formula I-a

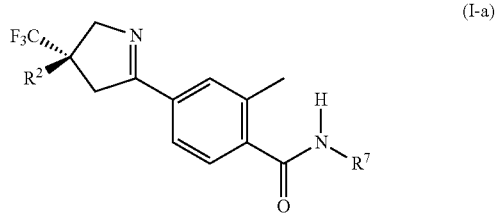

(I-a)

wherein $R^2$ and $R^7$ have the values given in the Table

Table 2

Table 2 discloses compounds 2.1 to 2.138 of the formula I-b

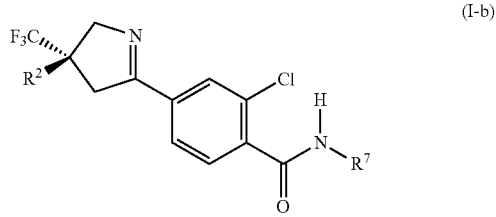

(I-b)

wherein $R^2$ and $R^7$ have the values given in the Table

Table 3

Table 3 discloses compounds 3.1 to 3.138 of the formula I-c

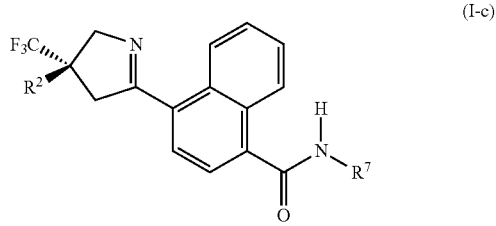

(I-c)

wherein $R^2$ and $R^7$ have the values given in the Table

Table 4

Table 4 discloses compounds 4.1 to 4.138 of the formula I-d

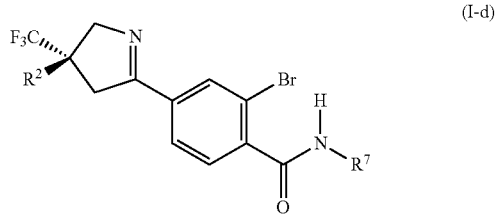

(I-d)

wherein $R^2$ and $R^7$ have the values given in the Table

Table 5
Table 5 discloses compounds 5.1 to 5.138 of the formula I-e

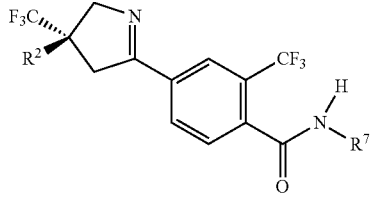
(I-e)

wherein $R^2$ and $R^7$ have the values given in the Table

Table 6
Table 6 discloses compounds 6.1 to 6.138 of the formula III-a

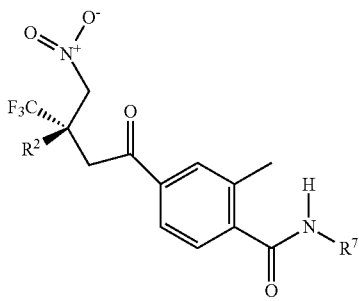
(III-a)

wherein $R^2$ and $R^7$ have the values given in the Table

Table 7
Table 7 discloses compounds 7.1 to 7.138 of the formula III-b

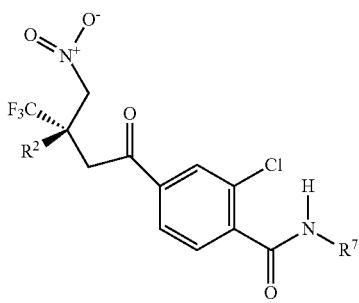
(III-b)

wherein $R^2$ and $R^7$ have the values given in the Table

Table 8
Table 8 discloses compounds 8.1 to 8.138 of the formula III-c

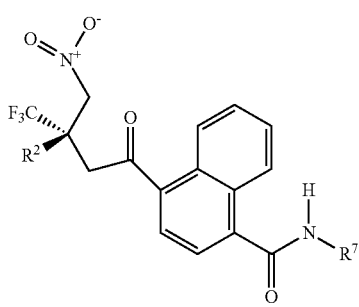
(III-c)

wherein $R^2$ and $R^7$ have the values given in the Table

Table 9
Table 9 discloses compounds 9.1 to 9.138 of the formula III-d

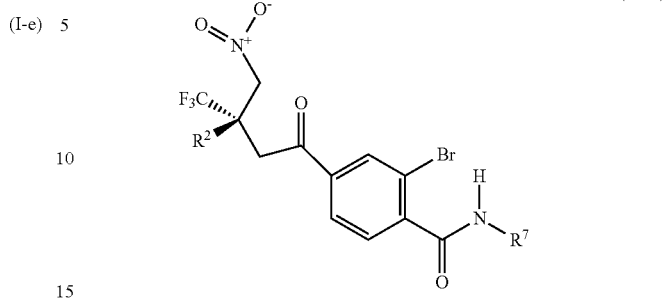
(III-d)

wherein $R^2$ and $R^7$ have the values given in the Table

Table 10
Table 10 discloses compounds 10.1 to 10.138 of the formula III-e

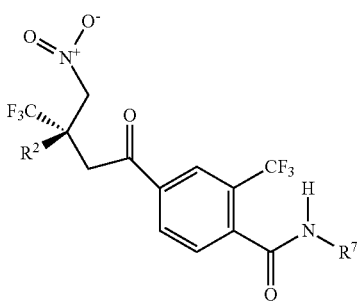
(III-e)

wherein $R^2$ and $R^7$ have the values given in the Table

Table 11
Table 11 discloses compounds 11.1 to 11.138 of the formula IV-a

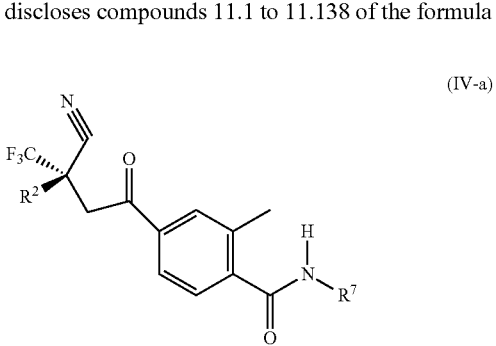
(IV-a)

wherein $R^2$ and $R^7$ have the values given in the Table

Table 12
Table 12 discloses compounds 12.1 to 12.138 of the formula IV-b

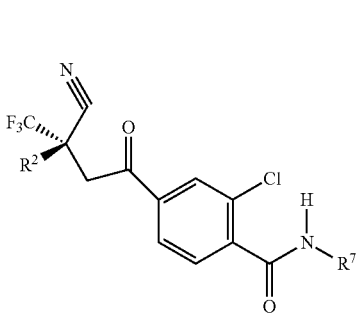
(IV-b)

wherein $R^2$ and $R^7$ have the values given in the Table

Table 13
Table 13 discloses compounds 13.1 to 13.138 of the formula IV-c

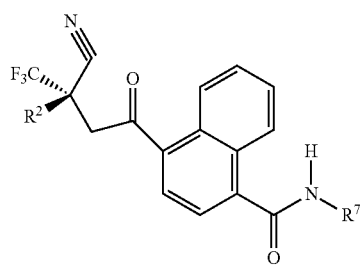
(IV-c)

wherein R² and R⁷ have the values given in the Table

Table 14
Table 14 discloses compounds 14.1 to 14.138 of the formula IV-d

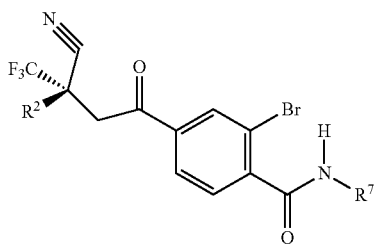
(IV-d)

wherein R² and R⁷ have the values given in the Table

Table 15
Table 15 discloses compounds 15.1 to 15.138 of the formula IV-e

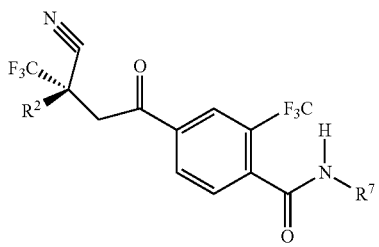
(IV-e)

wherein R² and R⁷ have the values given in the Table

Table 16
Table 16 discloses compounds 16.1 to 16.138 of the formula II-a1

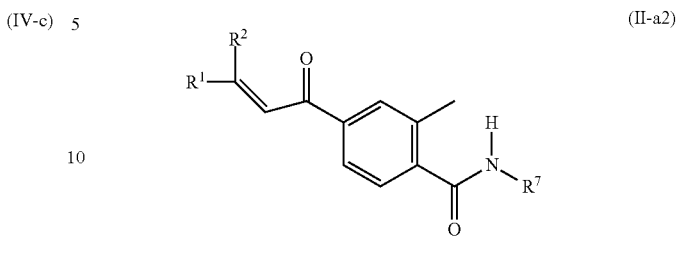
(II-a1)

wherein R² and R⁷ have the values given in the Table and R¹ is CF₃

Table 17
Table 17 discloses compounds 17.1 to 17.138 of the formula II-a2

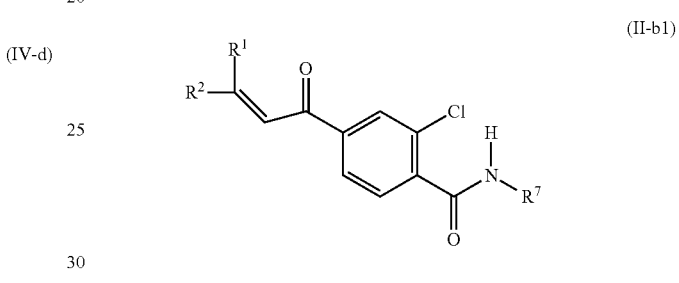
(II-a2)

wherein R² and R⁷ have the values given in the Table and R¹ is CF₃

Table 18
Table 18 discloses compounds 18.1 to 18.138 of the formula II-b1

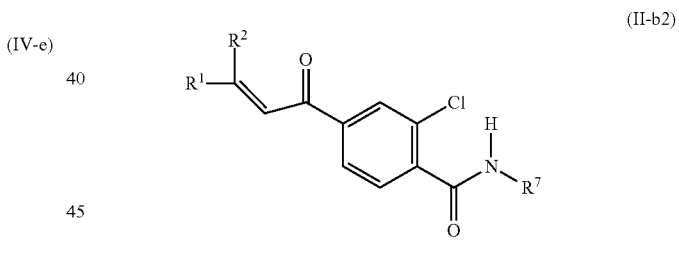
(II-b1)

wherein R² and R⁷ have the values given in the Table and R¹ is CF₃

Table 19
Table 19 discloses compounds 19.1 to 19.138 of the formula II-b2

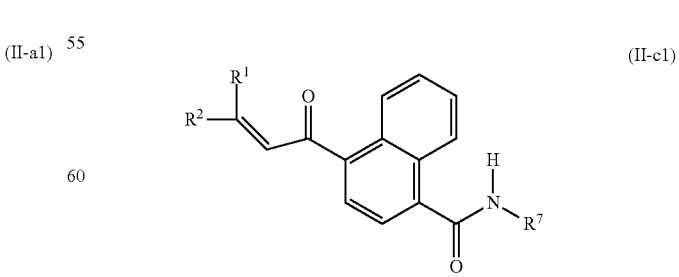
(II-b2)

wherein R² and R⁷ have the values given in the Table and R¹ is CF₃

Table 20
Table 20 discloses compounds 20.1 to 20.138 of the formula II-c1

(II-c1)

wherein R² and R⁷ have the values given in the Table and R¹ is CF₃

Table 21
Table 21 discloses compounds 21.1 to 21.138 of the formula II-c2

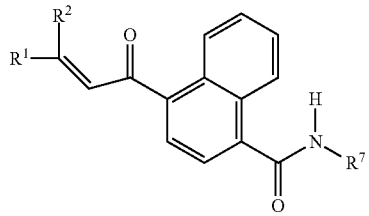
(II-c2)

Table 22
Table 22 discloses compounds 22.1 to 22.138 of the formula II-d1

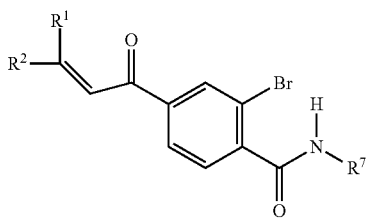
(II-d1)

wherein $R^2$ and $R^7$ have the values given in the Table and $R^1$ is $CF_3$

Table 23
Table 23 discloses compounds 23.1 to 23.138 of the formula II-d2

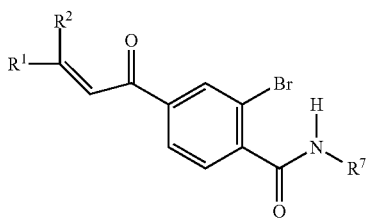
(II-d2)

wherein $R^2$ and $R^7$ have the values given in the Table and $R^1$ is $CF_3$

Table 24
Table 24 discloses compounds 24.1 to 24.138 of the formula II-e1

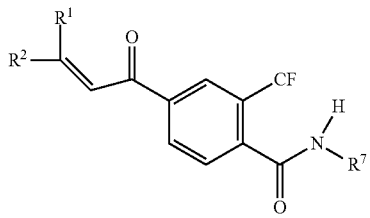
(II-e1)

wherein $R^2$ and $R^7$ have the values given in the Table and $R^1$ is $CF_3$

Table 25
Table 25 discloses compounds 25.1 to 25.138 of the formula II-e2

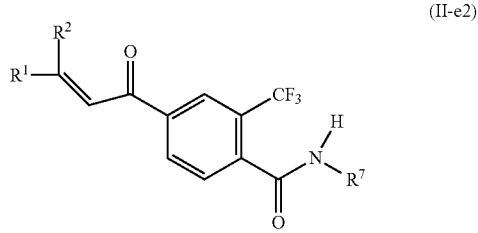
(II-e2)

wherein $R^2$ and $R^7$ have the values given in the Table and $R^1$ is $CF_3$.

Table 26
Table 26 discloses compounds 26.1 to 26.138 of the formula XXIII-a1

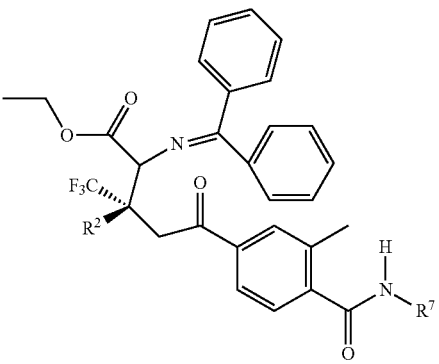
(XXIII-a1)

wherein $R^2$ and $R^7$ have the values given in the Table

Table 27
Table 27 discloses compounds 27.1 to 27.138 of the formula XXIII-b1

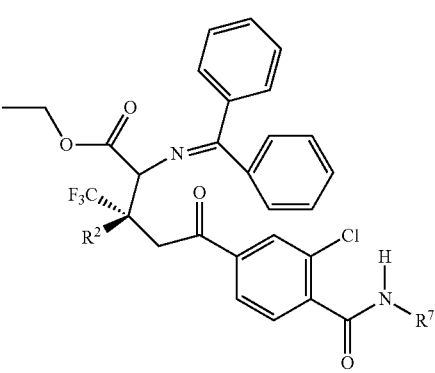
(XXIII-b1)

wherein $R^2$ and $R^7$ have the values given in the Table

Table 28
Table 28 discloses compounds 28.1 to 28.138 of the formula XXIII-c1

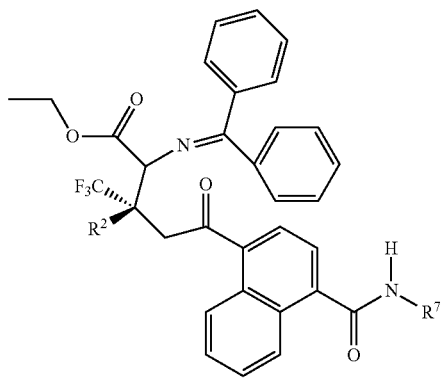

(XXIII-c1)

wherein $R^2$ and $R^7$ have the values given in the Table
Table 29
Table 29 discloses compounds 29.1 to 29.138 of the formula XXIII-d1

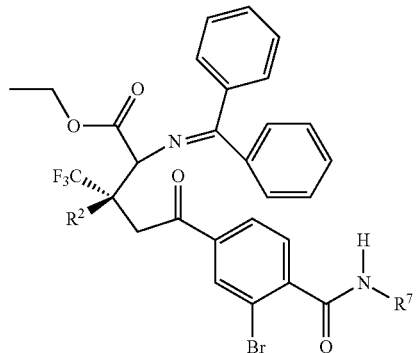

(XXIII-d1)

wherein $R^2$ and $R^7$ have the values given in the Table
Table 30
Table 30 discloses compounds 30.1 to 30.138 of the formula XXIII-e1

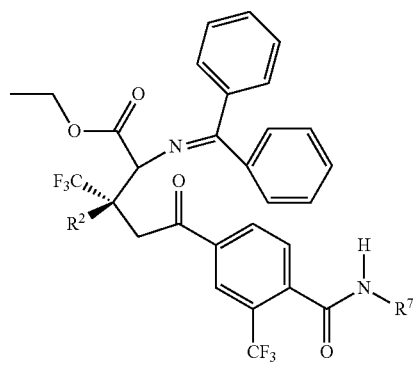

(XXIII-e1)

wherein $R^2$ and $R^7$ have the values given in the Table

Table 31
Table 31 discloses compounds 31.1 to 31.138 of the formula XXIII-a2

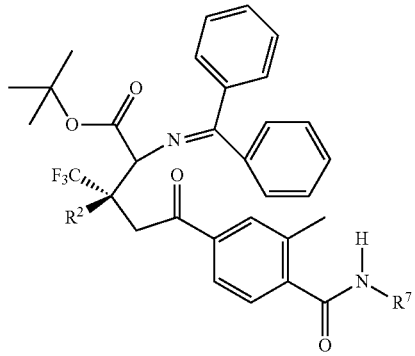

(XXIII-a2)

wherein $R^2$ and $R^7$ have the values given in the Table
Table 32
Table 32 discloses compounds 32.1 to 32.138 of the formula XXIII-b2

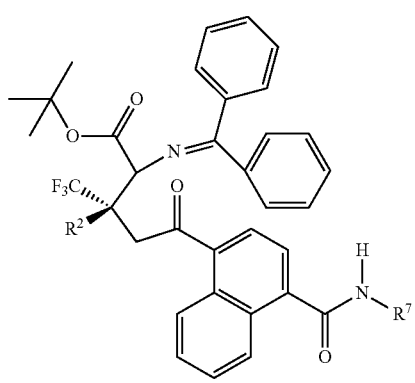

(XXIII-b2)

wherein $R^2$ and $R^7$ have the values given in the Table
Table 33
Table 33 discloses compounds 33.1 to 33.138 of the formula XXIII-c2

(XXIII-c2)

wherein $R^2$ and $R^7$ have the values given in the Table

Table 34
Table 34 discloses compounds 34.1 to 34.138 of the formula XXIII-d2

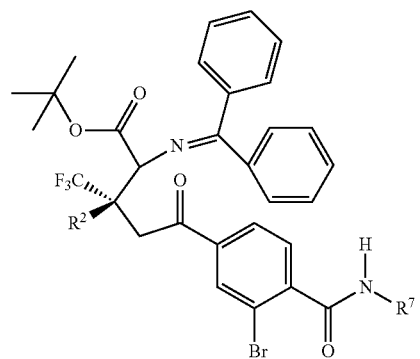
(XXIII-d2)

wherein R² and R⁷ have the values given in the Table

Table 35
Table 35 discloses compounds 35.1 to 35.138 of the formula XXIII-e2

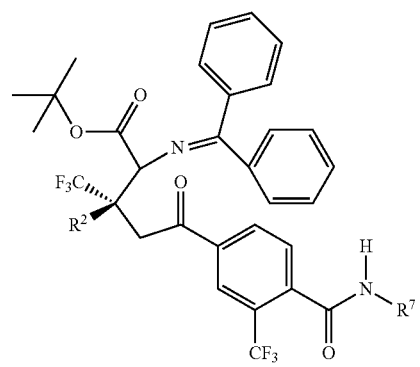
(XXIII-e2)

wherein R² and R⁷ have the values given in the Table

Table 36
Table 36 discloses compounds 36.1 to 36.138 of the formula XXIII-a3

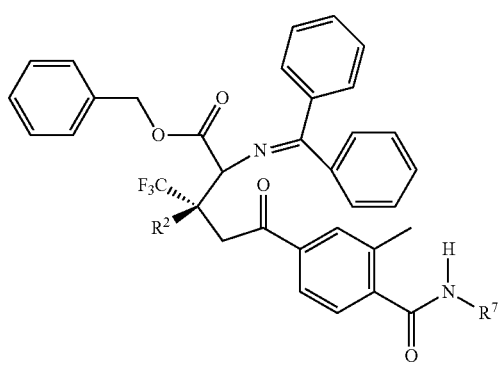
(XXIII-a3)

wherein R² and R⁷ have the values given in the Table

Table 37
Table 37 discloses compounds 37.1 to 37.138 of the formula XXIII-b3

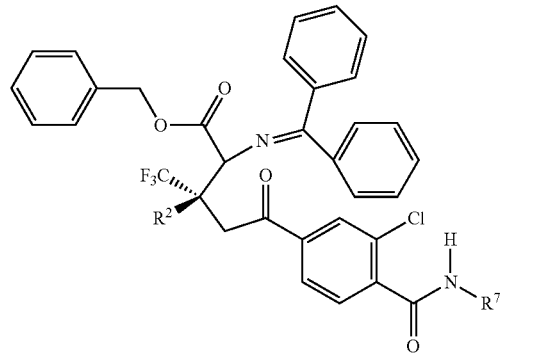
(XXIII-b3)

wherein R² and R⁷ have the values given in the Table

Table 38
Table 38 discloses compounds 38.1 to 38.138 of the formula XXIII-c3

(XXIII-c3)

wherein R² and R⁷ have the values given in the Table

Table 39
Table 39 discloses compounds 39.1 to 39.138 of the formula XXIII-d3

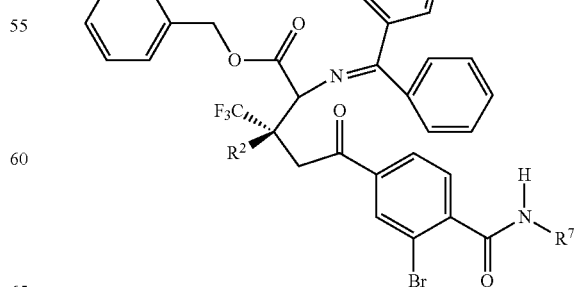
(XXIII-d3)

wherein R² and R⁷ have the values given in the Table

Table 40

Table 40 discloses compounds 40.1 to 40.138 of the formula XXIII-e3

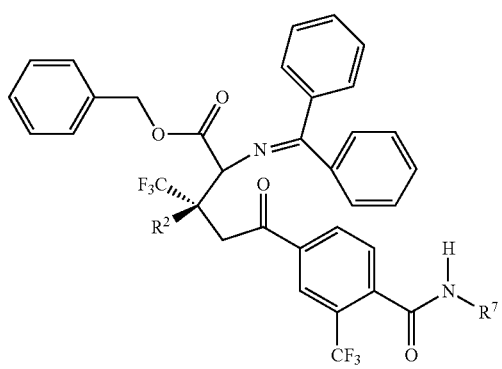
(XXIII-e3)

wherein $R^2$ and $R^7$ have the values given in the Table

Table 41

Table 41 discloses compounds 41.1 to 41.138 of the formula XXIV-a1

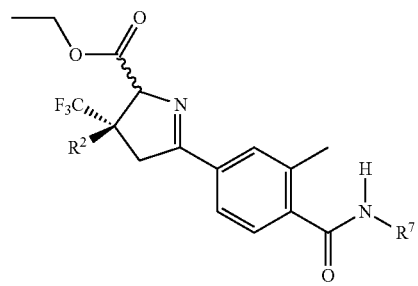
(XXIV-a1)

wherein $R^2$ and $R^7$ have the values given in the Table

Table 42

Table 42 discloses compounds 42.1 to 42.138 of the formula XXIV-b1

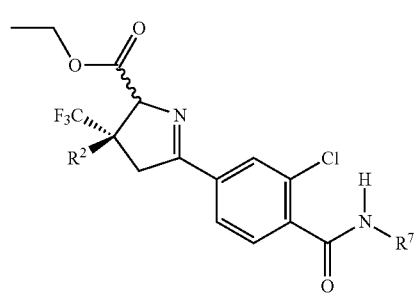
(XXIV-b1)

wherein $R^2$ and $R^7$ have the values given in the Table

Table 43

Table 43 discloses compounds 43.1 to 43.138 of the formula XXIV-c1

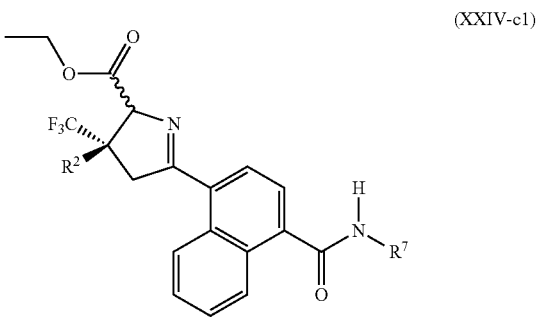
(XXIV-c1)

wherein $R^2$ and $R^7$ have the values given in the Table

Table 44

Table 44 discloses compounds 44.1 to 44.138 of the formula XXIV-d1

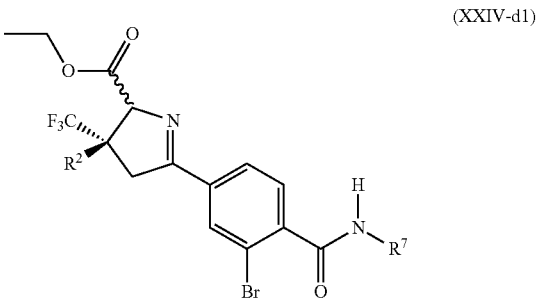
(XXIV-d1)

wherein $R^2$ and $R^7$ have the values given in the Table

Table 45

Table 45 discloses compounds 45.1 to 45.138 of the formula XXIV-e1

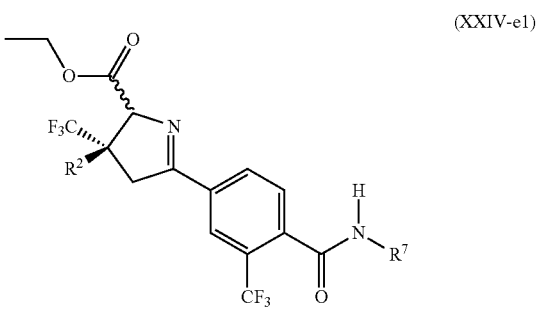
(XXIV-e1)

wherein $R^2$ and $R^7$ have the values given in the Table

Table 46

Table 46 discloses compounds 46.1 to 46.138 of the formula XXIV-a2

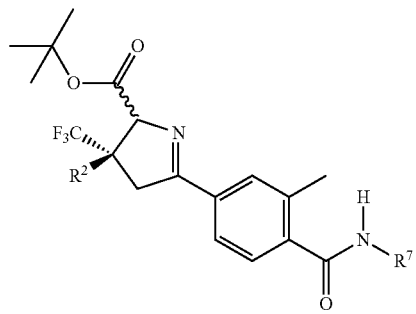

wherein R² and R⁷ have the values given in the Table

Table 47

Table 47 discloses compounds 47.1 to 47.138 of the formula XXIV-b2

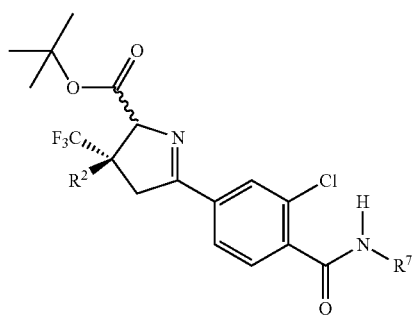

wherein R² and R⁷ have the values given in the Table

Table 48

Table 48 discloses compounds 48.1 to 48.138 of the formula XXIV-c2

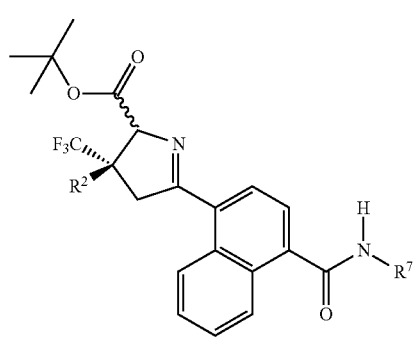

wherein R² and R⁷ have the values given in the Table

Table 49

Table 49 discloses compounds 49.1 to 49.138 of the formula XXIV-d2

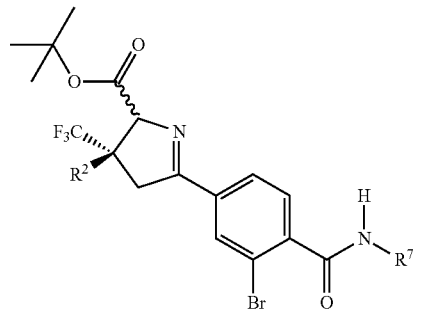

wherein R² and R⁷ have the values given in the Table

Table 50

Table 50 discloses compounds 50.1 to 50.138 of the formula XXIV-e2

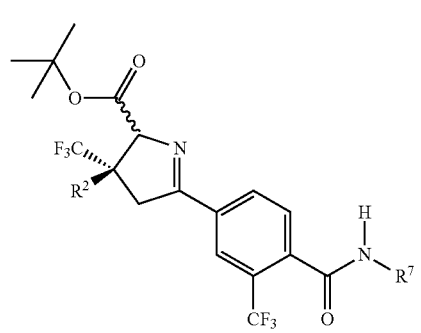

wherein R² and R⁷ have the values given in the Table

Table 51

Table 51 discloses compounds 51.1 to 51.138 of the formula XXIV-a3

wherein R² and R⁷ have the values given in the Table

Table 52

Table 52 discloses compounds 52.1 to 52.138 of the formula XXIV-b3

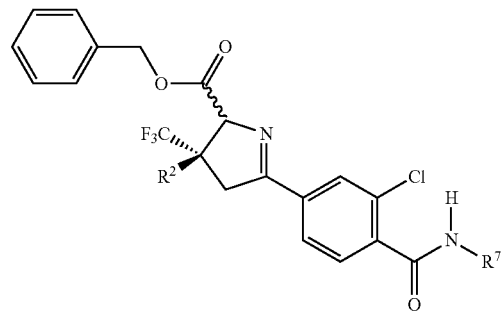

(XXIV-b3)

wherein $R^2$ and $R^7$ have the values given in the Table

Table 53

Table 53 discloses compounds 53.1 to 53.138 of the formula XXIV-c3

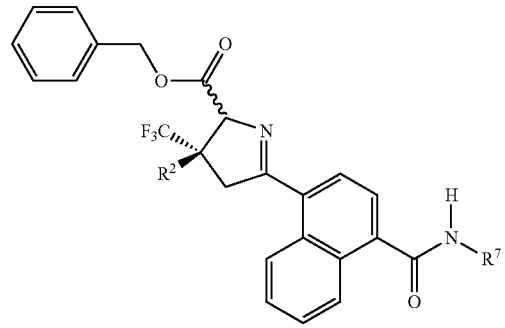

(XXIV-c3)

wherein $R^2$ and $R^7$ have the values given in the Table

Table 54

Table 54 discloses compounds 54.1 to 54.138 of the formula XXIV-d3

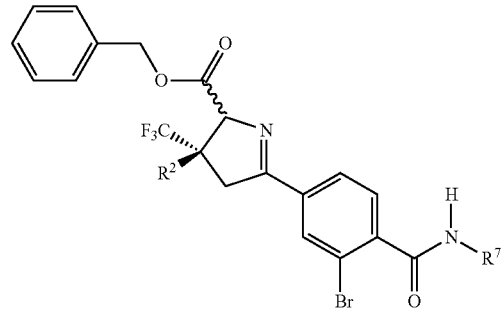

(XXIV-d3)

wherein $R^2$ and $R^7$ have the values given in the Table

Table 55

Table 55 discloses compounds 55.1 to 55.138 of the formula XXIV-e3

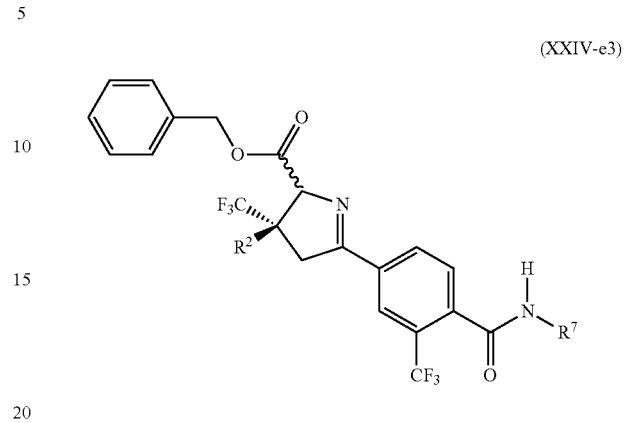

(XXIV-e3)

wherein $R^2$ and $R^7$ have the values given in the Table

Tables 56 to 66 provide further preferred compounds of the invention.

Table Y represents Table 56 when Y is 56, Table 57 when Y is 57, Table 58 when Y is 58, Table 59 when Y is 59, Table 60 when Y is 60, Table 61 when Y is 61, Table 62 when Y is 62, Table 63 when Y is 63, Table 64 when Y is 64, Table 65 when Y is 65, and Table 66 when Y is 66.

| No. | $R^2$ | $R^5$ | R |
|---|---|---|---|
| Y.1 | 3,5-dichloro-phenyl | CN | 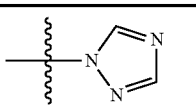 1,2,4-triazol-1-yl |
| Y.2 | 3,5-dichloro-phenyl | CN | 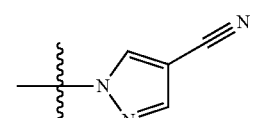 4-cyano-pyrazol-1-yl |
| Y.3 | 3,5-dichloro-phenyl | CN | 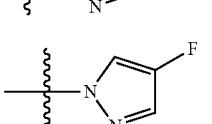 4-fluoro-pyrazol-1-yl |
| Y.4 | 3,5-dichloro-phenyl | CN | 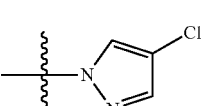 4-chloro-pyrazol-1-yl |
| Y.5 | 3,5-dichloro-phenyl | H | 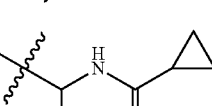 |
| Y.6 | 3,5-dichloro-phenyl | H | 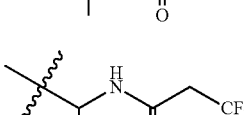 |
| Y.7 | 3,5-dichloro-phenyl | Cl | 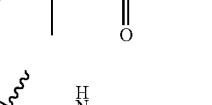 |

-continued

| No. | R² | R⁵ | R |
|---|---|---|---|
| Y.8 | 3,5-dichloro-phenyl | Cl | 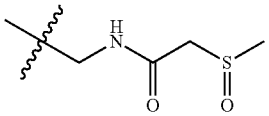 [SMILES: *CNC(=O)CS(C)=O] |
| Y.9 | 3,5-dichloro-phenyl | Cl | 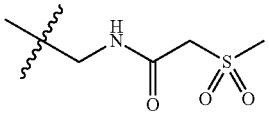 [SMILES: *CNC(=O)CS(C)(=O)=O] |
| Y.10 | 3,5-dichloro-phenyl | Cl | 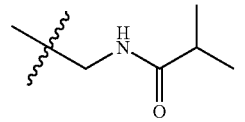 [SMILES: *CNC(=O)C(C)C] |
| Y.11 | 3,5-dichloro-phenyl | Cl | 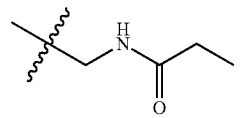 [SMILES: *CNC(=O)CC] |
| Y.12 | 3,5-dichloro-phenyl | Cl | 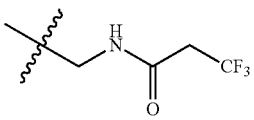 [SMILES: *CNC(=O)CC(F)(F)F] |
| Y.13 | 3,5-dichloro-phenyl | Cl | 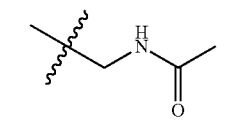 [SMILES: *CNC(C)=O] |
| Y.14 | 3,5-dichloro-phenyl | Cl | 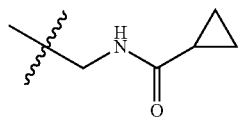 |
| Y.15 | 3,5-dichloro-phenyl | Br | 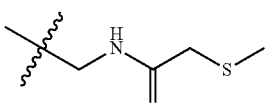 |
| Y.16 | 3,5-dichloro-phenyl | Br | 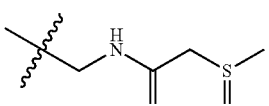 |
| Y.17 | 3,5-dichloro-phenyl | Br | 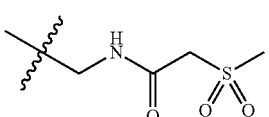 |
| Y.18 | 3,5-dichloro-phenyl | Br | 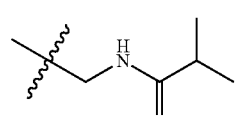 |
| Y.19 | 3,5-dichloro-phenyl | Br | 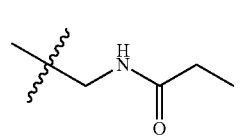 [SMILES: *CNC(=O)CC] |

-continued

| No. | R² | R⁵ | R |
|---|---|---|---|
| Y.20 | 3,5-dichloro-phenyl | Br | 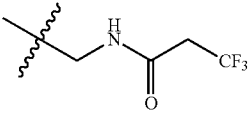 [SMILES: *CNC(=O)CC(F)(F)F] |
| Y.21 | 3,5-dichloro-phenyl | Br | 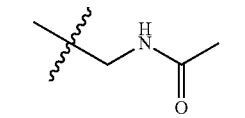 [SMILES: *CNC(C)=O] |
| Y.22 | 3,5-dichloro-phenyl | Br | 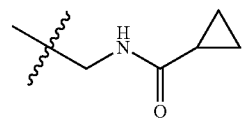 [SMILES: *CNC(=O)C1CC1] |
| Y.23 | 3,5-dichloro-phenyl | CF₃ | 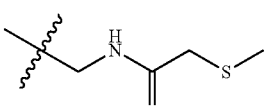 |
| Y.24 | 3,5-dichloro-phenyl | CF₃ | 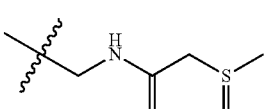 |
| Y.25 | 3,5-dichloro-phenyl | CF₃ | 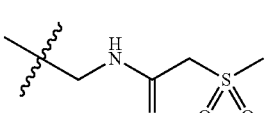 |
| Y.26 | 3,5-dichloro-phenyl | CF₃ | 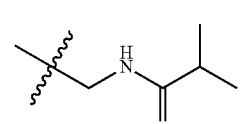 |
| Y.27 | 3,5-dichloro-phenyl | CF₃ | 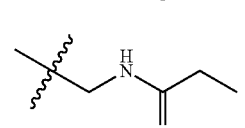 |
| Y.28 | 3,5-dichloro-phenyl | CF₃ | 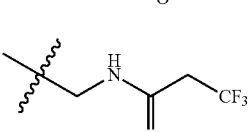 |
| Y.29 | 3,5-dichloro-phenyl | CF₃ | 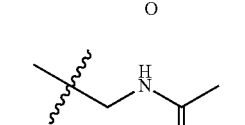 |
| Y.30 | 3,5-dichloro-phenyl | CF₃ | 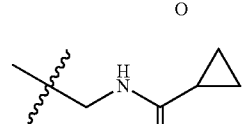 |
| Y.31 | 3,5-Bis trifluoro methyl-phenyl | CN | 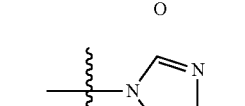 |

75
-continued

| No. | R² | R⁵ | R |
|---|---|---|---|
| Y.32 | 3,5-Bis trifluoro methyl-phenyl | CN | 4-cyanopyrazol-1-yl |
| Y.33 | 3,5-Bis trifluoro methyl-phenyl | CN | 4-fluoropyrazol-1-yl |
| Y.34 | 3,5-Bis trifluoro methyl-phenyl | CN | 4-chloropyrazol-1-yl |
| Y.35 | 3,5-Bis trifluoro methyl-phenyl | H | -CH(CH₃)NHC(O)-cyclopropyl |
| Y.36 | 3,5-Bis trifluoro methyl-phenyl | H | -CH(CH₃)NHC(O)CH₂CF₃ |
| Y.37 | 3,5-Bis trifluoro methyl-phenyl | Cl | -CH₂NHC(O)CH₂SCH₃ |
| Y.38 | 3,5-Bis trifluoro methyl-phenyl | Cl | -CH₂NHC(O)CH₂S(O)CH₃ |
| Y.39 | 3,5-Bis trifluoro methyl-phenyl | Cl | -CH₂NHC(O)CH₂S(O)₂CH₃ |
| Y.40 | 3,5-Bis trifluoro methyl-phenyl | Cl | -CH₂NHC(O)CH(CH₃)₂ |
| Y.41 | 3,5-Bis trifluoro methyl-phenyl | Cl | -CH₂NHC(O)CH₂CH₃ |
| Y.42 | 3,5-Bis trifluoro methyl-phenyl | Cl | -CH₂NHC(O)CH₂CF₃ |
| Y.43 | 3,5-Bis trifluoro methyl-phenyl | Cl | -CH₂NHC(O)CH₃ |

76
-continued

| No. | R² | R⁵ | R |
|---|---|---|---|
| Y.44 | 3,5-Bis trifluoro methyl-phenyl | Cl | -CH₂NHC(O)-cyclopropyl |
| Y.45 | 3,5-Bis trifluoro methyl-phenyl | Br | -CH₂NHC(O)CH₂SCH₃ |
| Y.46 | 3,5-Bis trifluoro methyl-phenyl | Br | -CH₂NHC(O)CH₂S(O)CH₃ |
| Y.47 | 3,5-Bis trifluoro methyl-phenyl | Br | -CH₂NHC(O)CH₂S(O)₂CH₃ |
| Y.48 | 3,5-Bis trifluoro methyl-phenyl | Br | -CH₂NHC(O)CH(CH₃)₂ |
| Y.49 | 3,5-Bis trifluoro methyl-phenyl | Br | -CH₂NHC(O)CH₂CH₃ |
| Y.50 | 3,5-Bis trifluoro methyl-phenyl | Br | -CH₂NHC(O)CH₂CF₃ |
| Y.51 | 3,5-Bis trifluoro methyl-phenyl | Br | -CH₂NHC(O)CH₃ |
| Y.52 | 3,5-Bis trifluoro methyl-phenyl | Br | -CH₂NHC(O)-cyclopropyl |
| Y.53 | 3,5-Bis trifluoro methyl-phenyl | CF₃ | -CH₂NHC(O)CH₂SCH₃ |
| Y.54 | 3,5-Bis trifluoro methyl-phenyl | CF₃ | -CH₂NHC(O)CH₂S(O)CH₃ |
| Y.55 | 3,5-Bis trifluoro methyl-phenyl | CF₃ | -CH₂NHC(O)CH₂S(O)₂CH₃ |

| No. | R² | R⁵ | R |
|---|---|---|---|
| Y.56 | 3,5-Bis trifluoro methyl-phenyl | CF₃ | -CH₂-NH-C(O)-CH(CH₃)₂ |
| Y.57 | 3,5-Bis trifluoro methyl-phenyl | CF₃ | -CH₂-NH-C(O)-CH₂CH₃ |
| Y.58 | 3,5-Bis trifluoro methyl-phenyl | CF₃ | -CH₂-NH-C(O)-CH₂-CF₃ |
| Y.59 | 3,5-Bis trifluoro methyl-phenyl | CF₃ | -CH₂-NH-C(O)-CH₃ |
| Y.60 | 3,5-Bis trifluoro methyl-phenyl | CF₃ | -CH₂-NH-C(O)-cyclopropyl |
| Y.61 | 3,4,5-Trichloro-phenyl | CN | 1,2,4-triazol-1-yl |
| Y.62 | 3,4,5-Trichloro-phenyl | CN | 4-cyano-pyrazol-1-yl |
| Y.63 | 3,4,5-Trichloro-phenyl | CN | 4-fluoro-pyrazol-1-yl |
| Y.64 | 3,4,5-Trichloro-phenyl | CN | 4-chloro-pyrazol-1-yl |
| Y.65 | 3,4,5-Trichloro-phenyl | H | -CH(CH₃)-NH-C(O)-cyclopropyl |
| Y.66 | 3,4,5-Trichloro-phenyl | H | -CH(CH₃)-NH-C(O)-CH₂-CF₃ |
| Y.67 | 3,4,5-Trichloro-phenyl | Cl | -CH₂-NH-C(O)-CH₂-S-CH₃ |
| Y.68 | 3,4,5-Trichloro-phenyl | Cl | -CH₂-NH-C(O)-CH₂-S(O)-CH₃ |
| Y.69 | 3,4,5-Trichloro-phenyl | Cl | -CH₂-NH-C(O)-CH₂-S(O)₂-CH₃ |
| Y.70 | 3,4,5-Trichloro-phenyl | Cl | -CH₂-NH-C(O)-CH(CH₃)₂ |
| Y.71 | 3,4,5-Trichloro-phenyl | Cl | -CH₂-NH-C(O)-CH₂CH₃ |
| Y.72 | 3,4,5-Trichloro-phenyl | Cl | -CH₂-NH-C(O)-CH₂-CF₃ |
| Y.73 | 3,4,5-Trichloro-phenyl | Cl | -CH₂-NH-C(O)-CH₃ |
| Y.74 | 3,4,5-Trichloro-phenyl | Cl | -CH₂-NH-C(O)-cyclopropyl |
| Y.75 | 3,4,5-Trichloro-phenyl | Br | -CH₂-NH-C(O)-CH₂-S-CH₃ |
| Y.76 | 3,4,5-Trichloro-phenyl | Br | -CH₂-NH-C(O)-CH₂-S(O)-CH₃ |
| Y.77 | 3,4,5-Trichloro-phenyl | Br | -CH₂-NH-C(O)-CH₂-S(O)₂-CH₃ |
| Y.78 | 3,4,5-Trichloro-phenyl | Br | -CH₂-NH-C(O)-CH(CH₃)₂ |
| Y.79 | 3,4,5-Trichloro-phenyl | Br | -CH₂-NH-C(O)-CH₂CH₃ |

-continued

| No. | R² | R⁵ | R |
|---|---|---|---|
| Y.80 | 3,4,5-Trichloro-phenyl | Br | 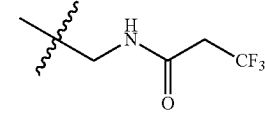 [SMILES: *CNC(=O)CC(F)(F)F] |
| Y.81 | 3,4,5-Trichloro-phenyl | Br | 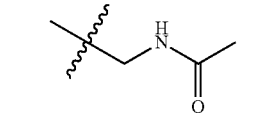 [SMILES: *CNC(C)=O] |
| Y.82 | 3,4,5-Trichloro-phenyl | Br | 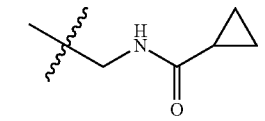 [SMILES: *CNC(=O)C1CC1] |
| Y.83 | 3,4,5-Trichloro-phenyl | CF₃ | 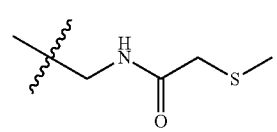 [SMILES: *CNC(=O)CSC] |
| Y.84 | 3,4,5-Trichloro-phenyl | CF₃ | 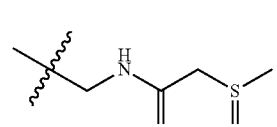 |
| Y.85 | 3,4,5-Trichloro-phenyl | CF₃ | 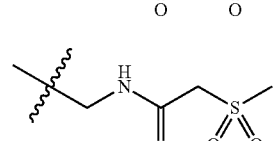 |
| Y.86 | 3,4,5-Trichloro-phenyl | CF₃ | 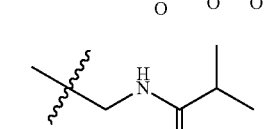 |
| Y.87 | 3,4,5-Trichloro-phenyl | CF₃ | 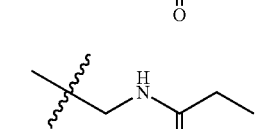 |
| Y.88 | 3,4,5-Trichloro-phenyl | CF₃ | 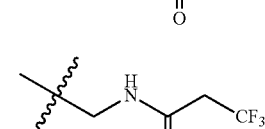 |
| Y.89 | 3,4,5-Trichloro-phenyl | CF₃ | 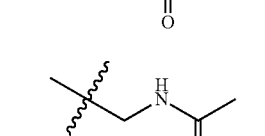 |
| Y.90 | 3,4,5-Trichloro-phenyl | CF₃ | 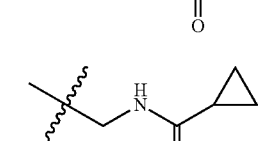 |
| Y.91 | 3,5-dichloro-4-fluoro-phenyl | CN | 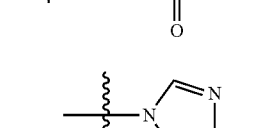 |

-continued

| No. | R² | R⁵ | R |
|---|---|---|---|
| Y.92 | 3,5-dichloro-4-fluoro-phenyl | CN | 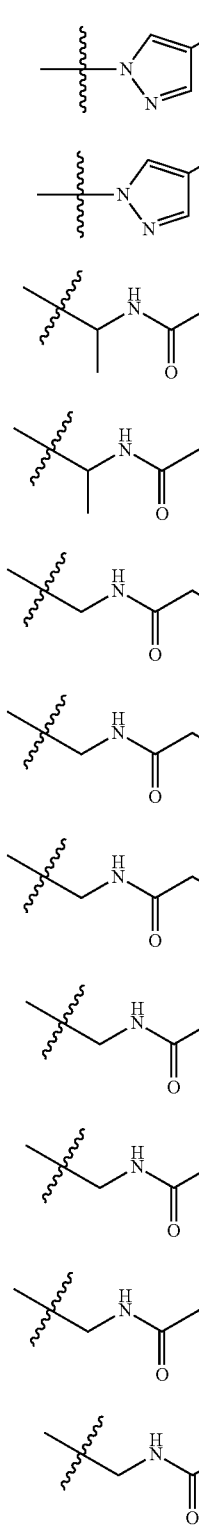 |
| Y.93 | 3,5-dichloro-4-fluoro-phenyl | CN | 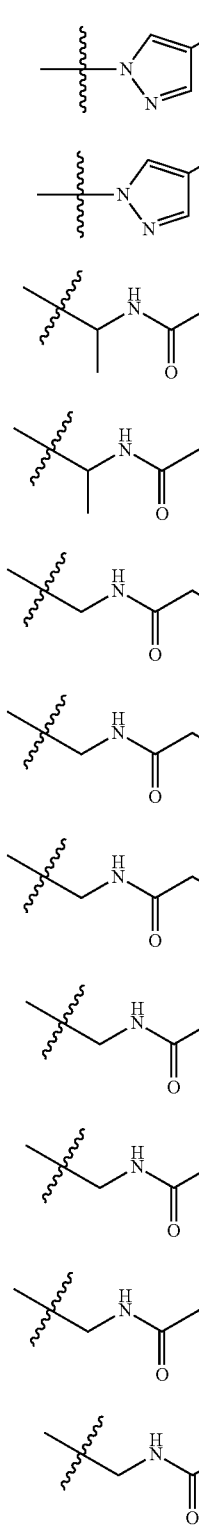 |
| Y.94 | 3,5-dichloro-4-fluoro-phenyl | CN | 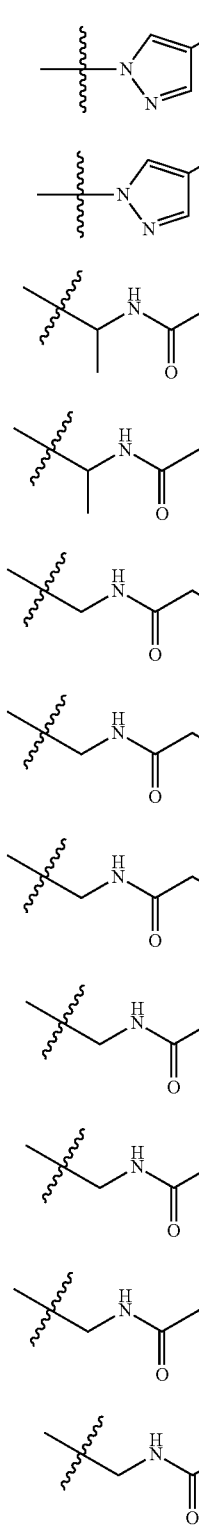 |
| Y.95 | 3,5-dichloro-4-fluoro-phenyl | H | 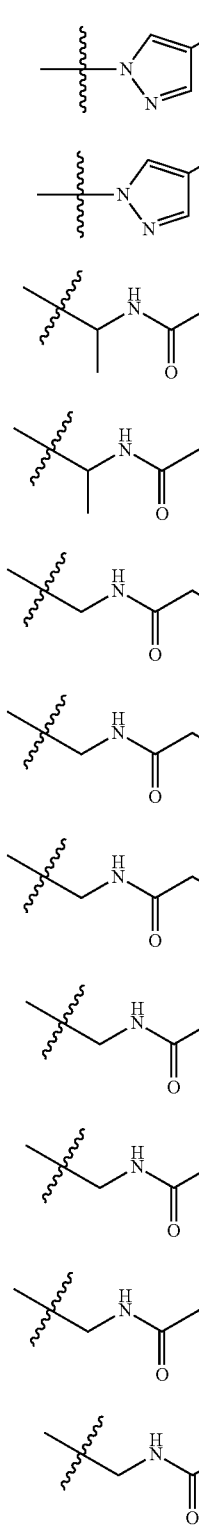 |
| Y.96 | 3,5-dichloro-4-fluoro-phenyl | H | 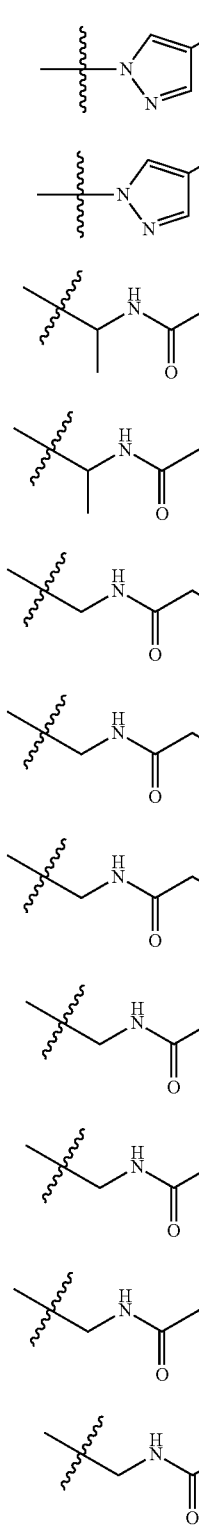 |
| Y.97 | 3,5-dichloro-4-fluoro-phenyl | Cl | 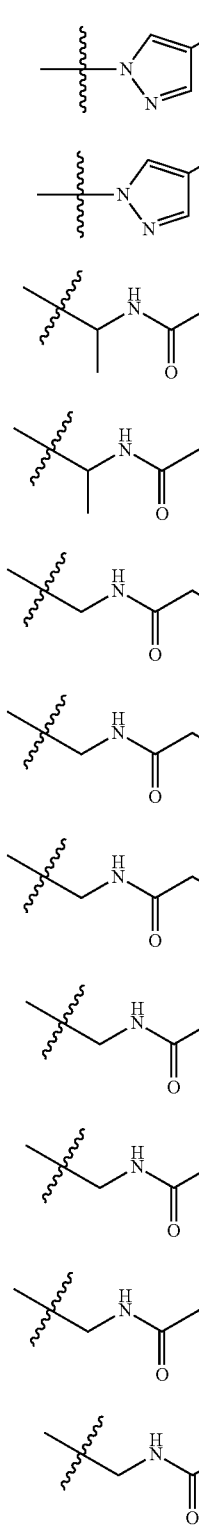 |
| Y.98 | 3,5-dichloro-4-fluoro-phenyl | Cl | 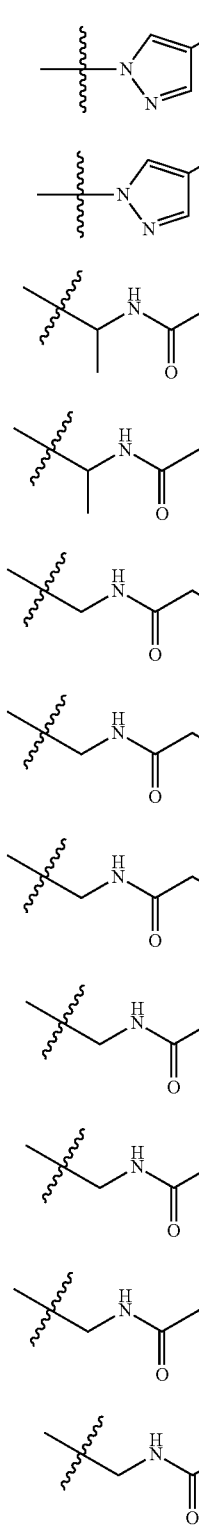 |
| Y.99 | 3,5-dichloro-4-fluoro-phenyl | Cl | 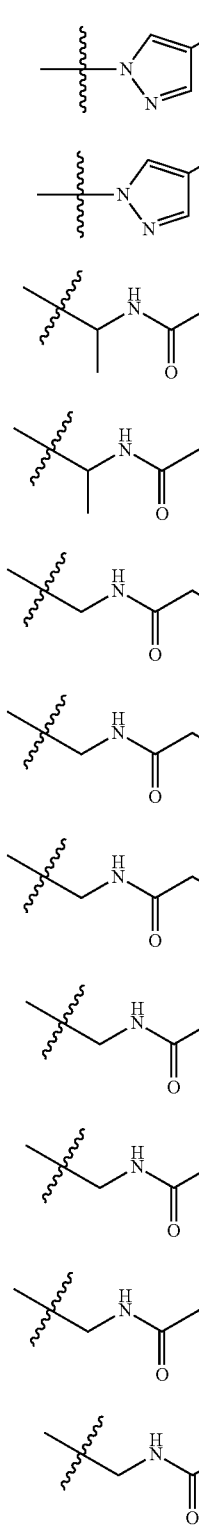 |
| Y.100 | 3,5-dichloro-4-fluoro-phenyl | Cl | 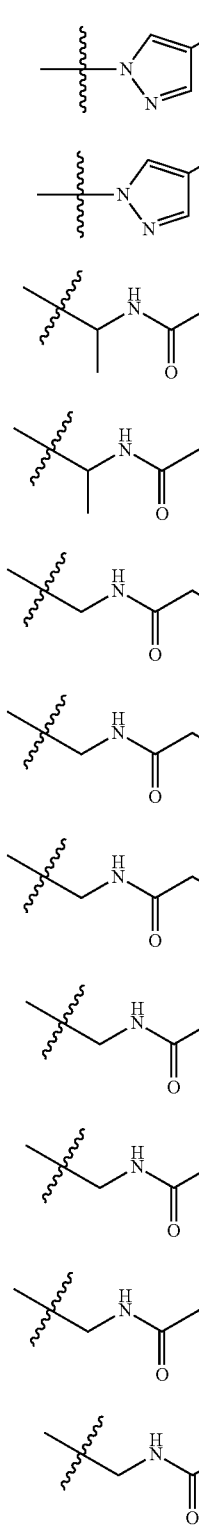 |
| Y.101 | 3,5-dichloro-4-fluoro-phenyl | Cl | 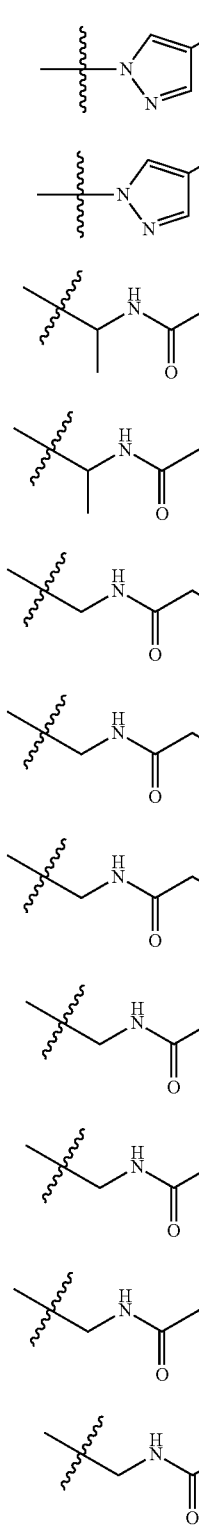 |
| Y.102 | 3,5-dichloro-4-fluoro-phenyl | Cl | 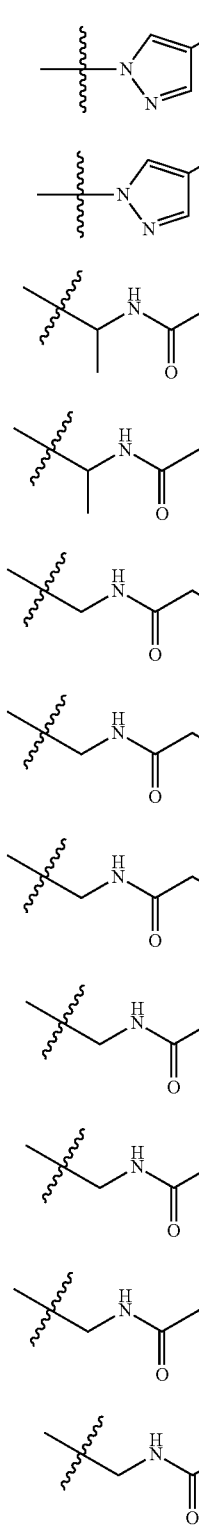 |
| Y.103 | 3,5-dichloro-4-fluoro-phenyl | Cl | 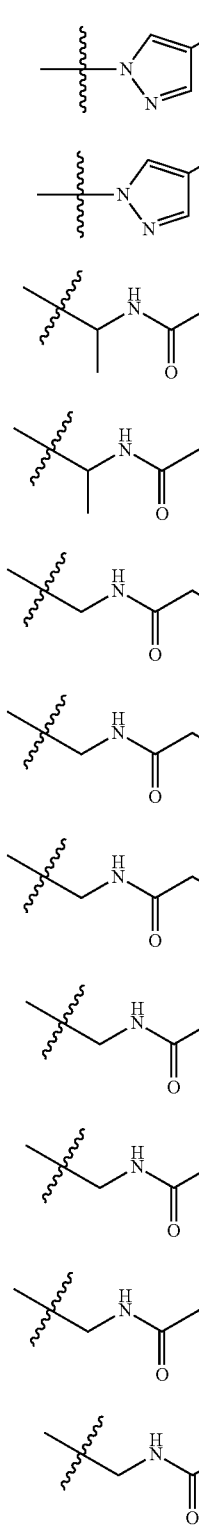 |

| No. | R² | R⁵ | R |
|---|---|---|---|
| Y.104 | 3,5-dichloro-4-fluoro-phenyl | Cl | -CH₂-NH-C(O)-cyclopropyl |
| Y.105 | 3,5-dichloro-4-fluoro-phenyl | Br | -CH₂-NH-C(O)-CH₂-S-CH₃ |
| Y.106 | 3,5-dichloro-4-fluoro-phenyl | Br | -CH₂-NH-C(O)-CH₂-S(O)-CH₃ |
| Y.107 | 3,5-dichloro-4-fluoro-phenyl | Br | -CH₂-NH-C(O)-CH₂-S(O)₂-CH₃ |
| Y.108 | 3,5-dichloro-4-fluoro-phenyl | Br | -CH₂-NH-C(O)-CH(CH₃)₂ |
| Y.109 | 3,5-dichloro-4-fluoro-phenyl | Br | -CH₂-NH-C(O)-CH₂CH₃ |
| Y.110 | 3,5-dichloro-4-fluoro-phenyl | Br | -CH₂-NH-C(O)-CH₂-CF₃ |
| Y.111 | 3,5-dichloro-4-fluoro-phenyl | Br | -CH₂-NH-C(O)-CH₃ |
| Y.112 | 3,5-dichloro-4-fluoro-phenyl | Br | -CH₂-NH-C(O)-cyclopropyl |
| Y.113 | 3,5-dichloro-4-fluoro-phenyl | CF₃ | -CH₂-NH-C(O)-CH₂-S-CH₃ |
| Y.114 | 3,5-dichloro-4-fluoro-phenyl | CF₃ | -CH₂-NH-C(O)-CH₂-S(O)-CH₃ |
| Y.115 | 3,5-dichloro-4-fluoro-phenyl | CF₃ | -CH₂-NH-C(O)-CH₂-S(O)₂-CH₃ |
| Y.116 | 3,5-dichloro-4-fluoro-phenyl | CF₃ | -CH₂-NH-C(O)-CH(CH₃)₂ |
| Y.117 | 3,5-dichloro-4-fluoro-phenyl | CF₃ | -CH₂-NH-C(O)-CH₂CH₃ |
| Y.118 | 3,5-dichloro-4-fluoro-phenyl | CF₃ | -CH₂-NH-C(O)-CH₂-CF₃ |
| Y.119 | 3,5-dichloro-4-fluoro-phenyl | CF₃ | -CH₂-NH-C(O)-CH₃ |
| Y.120 | 3,5-dichloro-4-fluoro-phenyl | CF₃ | -CH₂-NH-C(O)-cyclopropyl |
| Y.121 | 3-chloro-5-trifluoro methyl-phenyl | CN | -(1,2,4-triazol-1-yl) |
| Y.122 | 3-chloro-5-trifluoro methyl-phenyl | CN | -(4-cyano-pyrazol-1-yl) |
| Y.123 | 3-chloro-5-trifluoro methyl-phenyl | CN | -(4-fluoro-pyrazol-1-yl) |
| Y.124 | 3-chloro-5-trifluoro methyl-phenyl | CN | -(4-chloro-pyrazol-1-yl) |
| Y.125 | 3-chloro-5-trifluoro methyl-phenyl | H | -CH(CH₃)-NH-C(O)-cyclopropyl |
| Y.126 | 3-chloro-5-trifluoro methyl-phenyl | H | -CH(CH₃)-NH-C(O)-CH₂-CF₃ |
| Y.127 | 3-chloro-5-trifluoro methyl-phenyl | Cl | -CH₂-NH-C(O)-CH₂-S-CH₃ |

| No. | R² | R⁵ | R |
|---|---|---|---|
| Y.128 | 3-chloro-5-trifluoro methyl-phenyl | Cl | 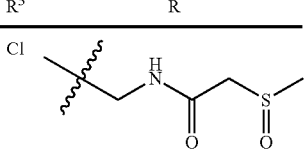 |
| Y.129 | 3-chloro-5-trifluoro methyl-phenyl | Cl | 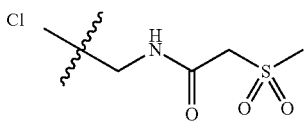 |
| Y.130 | 3-chloro-5-trifluoro methyl-phenyl | Cl | 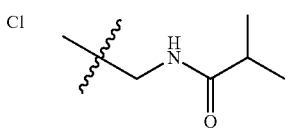 |
| Y.131 | 3-chloro-5-trifluoro methyl-phenyl | Cl | 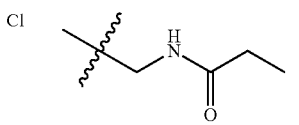 |
| Y.132 | 3-chloro-5-trifluoro methyl-phenyl | Cl | 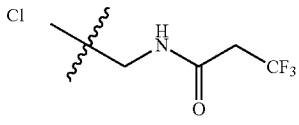 |
| Y.133 | 3-chloro-5-trifluoro methyl-phenyl | Cl | 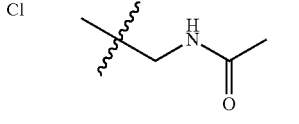 |
| Y.134 | 3-chloro-5-trifluoro methyl-phenyl | Cl | 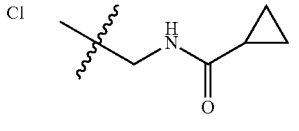 |
| Y.135 | 3-chloro-5-trifluoro methyl-phenyl | Br | 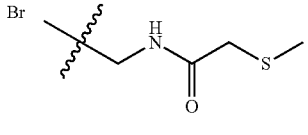 |
| Y.136 | 3-chloro-5-trifluoro methyl-phenyl | Br | 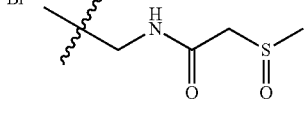 |
| Y.137 | 3-chloro-5-trifluoro methyl-phenyl | Br | 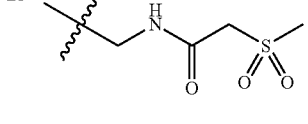 |
| Y.138 | 3-chloro-5-trifluoro methyl-phenyl | Br | 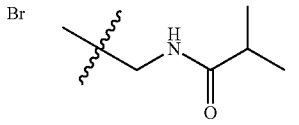 |
| Y.139 | 3-chloro-5-trifluoro methyl-phenyl | Br | 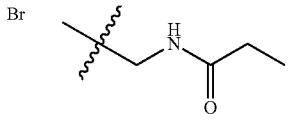 |
| Y.140 | 3-chloro-5-trifluoro methyl-phenyl | Br | 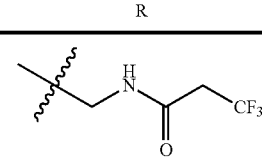 |
| Y.141 | 3-chloro-5-trifluoro methyl-phenyl | Br | 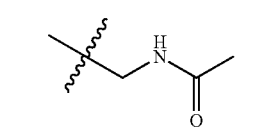 [SMILES: *CNC(C)=O] |
| Y.142 | 3-chloro-5-trifluoro methyl-phenyl | Br | 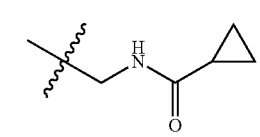 [SMILES: *CNC(=O)C1CC1] |
| Y.143 | 3-chloro-5-trifluoro methyl-phenyl | CF₃ | 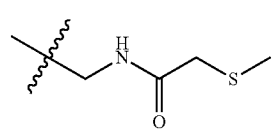 [SMILES: *CNC(=O)CSC] |
| Y.144 | 3-chloro-5-trifluoro methyl-phenyl | CF₃ | 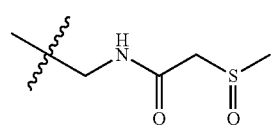 [SMILES: *CNC(=O)CS(C)=O] |
| Y.145 | 3-chloro-5-trifluoro methyl-phenyl | CF₃ | 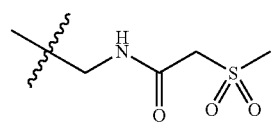 [SMILES: *CNC(=O)CS(C)(=O)=O] |
| Y.146 | 3-chloro-5-trifluoro methyl-phenyl | CF₃ | 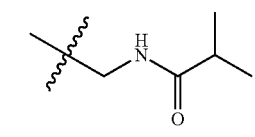 [SMILES: *CNC(=O)C(C)C] |
| Y.147 | 3-chloro-5-trifluoro methyl-phenyl | CF₃ | 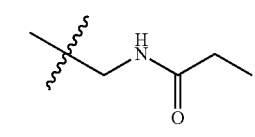 |
| Y.148 | 3-chloro-5-trifluoro methyl-phenyl | CF₃ | 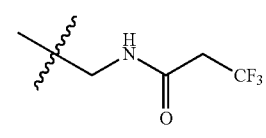 |
| Y.149 | 3-chloro-5-trifluoro methyl-phenyl | CF₃ | 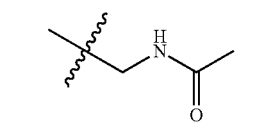 |
| Y.150 | 3-chloro-5-trifluoro methyl-phenyl | CF₃ | 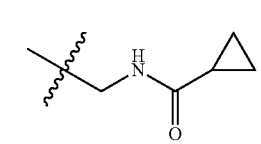 [SMILES: *CNC(=O)C1CC1] |
| Y.151 | 3-chloro-5-bromo-phenyl | CN | 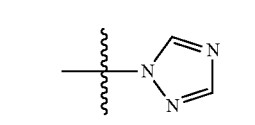 [SMILES: *n1cncn1] |

-continued

| No. | R² | R⁵ | R |
|---|---|---|---|
| Y.152 | 3-chloro-5-bromo-phenyl | CN | pyrazole-4-CN |
| Y.153 | 3-chloro-5-bromo-phenyl | CN | 4-F-pyrazole |
| Y.154 | 3-chloro-5-bromo-phenyl | CN | 4-Cl-pyrazole |
| Y.155 | 3-chloro-5-bromo-phenyl | H | CH(CH₃)NHC(O)-cyclopropyl |
| Y.156 | 3-chloro-5-bromo-phenyl | H | CH(CH₃)NHC(O)CH₂CF₃ |
| Y.157 | 3-chloro-5-bromo-phenyl | Cl | CH₂NHC(O)CH₂SCH₃ |
| Y.158 | 3-chloro-5-bromo-phenyl | Cl | CH₂NHC(O)CH₂S(O)CH₃ |
| Y.159 | 3-chloro-5-bromo-phenyl | Cl | CH₂NHC(O)CH₂S(O)₂CH₃ |
| Y.160 | 3-chloro-5-bromo-phenyl | Cl | CH₂NHC(O)CH(CH₃)₂ |
| Y.161 | 3-chloro-5-bromo-phenyl | Cl | CH₂NHC(O)CH₂CH₃ |
| Y.162 | 3-chloro-5-bromo-phenyl | Cl | CH₂NHC(O)CH₂CF₃ |
| Y.163 | 3-chloro-5-bromo-phenyl | Cl | CH₂NHC(O)CH₃ |

-continued

| No. | R² | R⁵ | R |
|---|---|---|---|
| Y.164 | 3-chloro-5-bromo-phenyl | Cl | CH₂NHC(O)-cyclopropyl |
| Y.165 | 3-chloro-5-bromo-phenyl | Br | CH₂NHC(O)CH₂SCH₃ |
| Y.166 | 3-chloro-5-bromo-phenyl | Br | CH₂NHC(O)CH₂S(O)CH₃ |
| Y.167 | 3-chloro-5-bromo-phenyl | Br | CH₂NHC(O)CH₂S(O)₂CH₃ |
| Y.168 | 3-chloro-5-bromo-phenyl | Br | CH₂NHC(O)CH(CH₃)₂ |
| Y.169 | 3-chloro-5-bromo-phenyl | Br | CH₂NHC(O)CH₂CH₃ |
| Y.170 | 3-chloro-5-bromo-phenyl | Br | CH₂NHC(O)CH₂CF₃ |
| Y.171 | 3-chloro-5-bromo-phenyl | Br | CH₂NHC(O)CH₃ |
| Y.172 | 3-chloro-5-bromo-phenyl | Br | CH₂NHC(O)-cyclopropyl |
| Y.173 | 3-chloro-5-bromo-phenyl | CF₃ | CH₂NHC(O)CH₂SCH₃ |
| Y.174 | 3-chloro-5-bromo-phenyl | CF₃ | CH₂NHC(O)CH₂S(O)CH₃ |
| Y.175 | 3-chloro-5-bromo-phenyl | CF₃ | CH₂NHC(O)CH₂S(O)₂CH₃ |

| No. | R² | R⁵ | R |
|---|---|---|---|
| Y.176 | 3-chloro-5-bromo-phenyl | CF₃ | 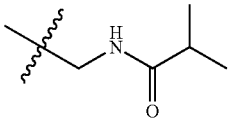 [SMILES: *CNC(=O)C(C)C] |
| Y.177 | 3-chloro-5-bromo-phenyl | CF₃ | 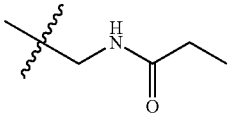 [SMILES: *CNC(=O)CC] |
| Y.178 | 3-chloro-5-bromo-phenyl | CF₃ | 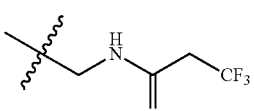 |
| Y.179 | 3-chloro-5-bromo-phenyl | CF₃ | 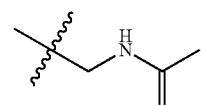 |
| Y.180 | 3-chloro-5-bromo-phenyl | CF₃ | 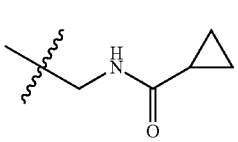 [SMILES: *CNC(=O)C1CC1] |

Table 56
Table 26 discloses compounds 56.1 to 56.180 of the formula I-f

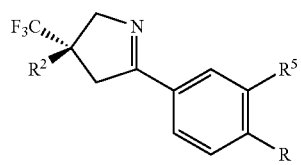

(I-f)

wherein R², R⁵ and R have the values given in the Table

Table 57
Table 57 discloses compounds 57.1 to 57.180 of the formula III-f

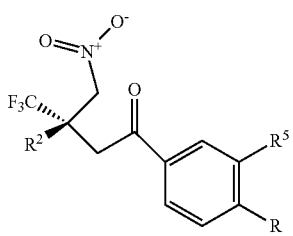

(III-f)

wherein R², R⁵ and R have the values given in the Table

Table 58
Table 58 discloses compounds 58.1 to 58.180 of the formula IV-f

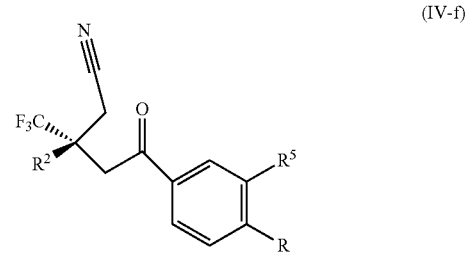

(IV-f)

wherein R², R⁵ and R have the values given in the Table

Table 59
Table 59 discloses compounds 59.1 to 59.180 of the formula II-f1

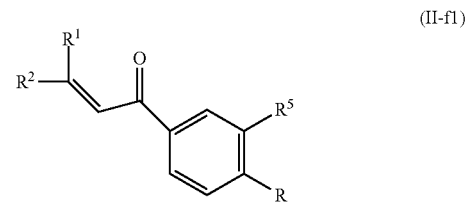

(II-f1)

wherein R², R⁵ and R have the values given in the Table and R¹ is CF₃

Table 60
Table 60 discloses compounds 60.1 to 60.180 of the formula II-f2

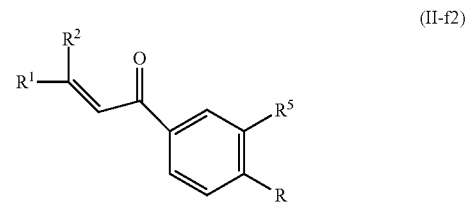

(II-f2)

wherein R², R⁵ and R have the values given in the Table and R¹ is CF₃

Table 61
Table 61 discloses compounds 61.1 to 61.180 of the formula XXIII-f1

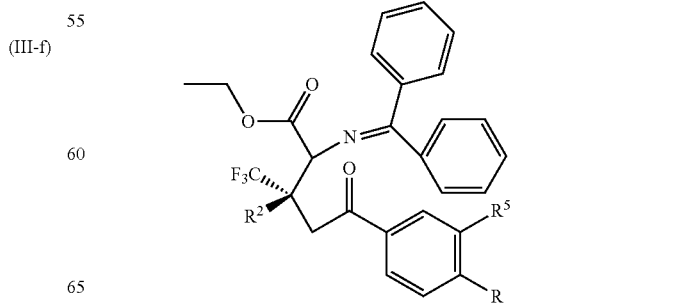

(XXIII-f1)

wherein R², R⁵ and R have the values given in the Table

Table 62

Table 62 discloses compounds 62.1 to 62.180 of the formula XXIII-f2

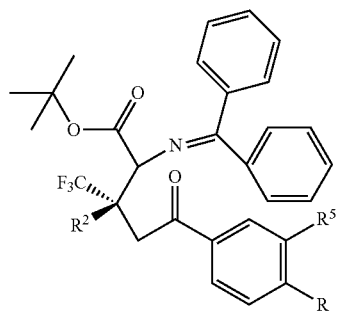

(XXIII-f2)

wherein $R^2$, $R^5$ and R have the values given in the Table

Table 63

Table 63 discloses compounds 63.1 to 63.180 of the formula XXIII-f3

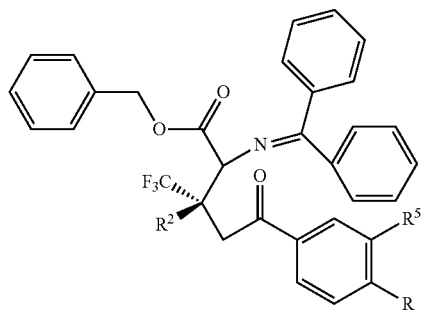

(XXIII-f3)

wherein $R^2$, $R^5$ and R have the values given in the Table

Table 64

Table 64 discloses compounds 64.1 to 64.180 of the formula XXIV-f1

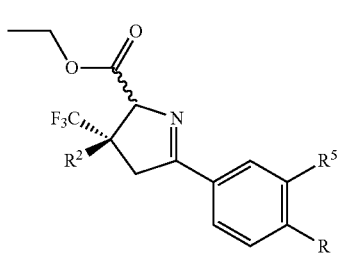

(XXIV-f1)

wherein $R^2$, $R^5$ and R have the values given in the Table

Table 65

Table 65 discloses compounds 65.1 to 65.180 of the formula XXIV-f2

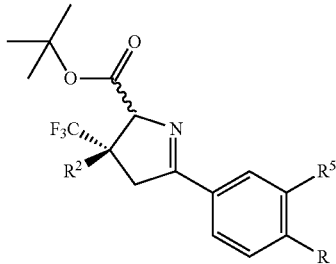

(XXIV-f2)

wherein $R^2$, $R^5$ and R have the values given in the Table

Table 66

Table 66 discloses compounds 66.1 to 66.180 of the formula XXIV-f3

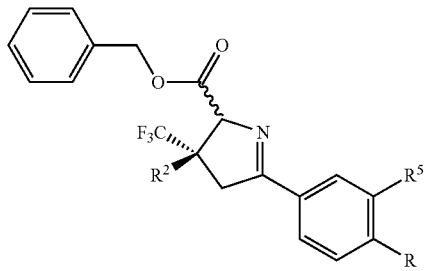

(XXIV-f3)

wherein $R^2$, $R^5$ and R have the values given in the Table

Tables 67 to 121 provide further preferred compounds of the invention.

Table Z represents Table 67 when Z is 67, Table 68 when Z is 68, Table 69 when Z is 69, Table 70 when Z is 70, Table 71 when Z is 71, Table 72 when Z is 72, Table 73 when Z is 73, Table 74 when Z is 74, Table 75 when Z is 75, Table 76 when Z is 76, Table 77 when Z is 77, Table 78 when Z is 78, Table 79 when Z is 79, Table 80 when Z is 80, Table 81 when Z is 81, Table 82 when Z is 82, Table 83 when Z is 83, Table 84 when Z is 84 and Table 85 when Z is 85, Table 86 when Z is 86, Table 87 when Z is 87, Table 88 when Z is 88, Table 89 when Z is 89, Table 90 when Z is 90, Table 91 when Z is 91, Table 92 when Z is 92, Table 93 when Z is 93, Table 94 when Z is 94, Table 95 when Z is 95, Table 96 when Z is 96, Table 97 when Z is 97, Table 98 when Z is 98, Table 99 when Z is 99, Table 100 when Z is 100, Table 101 when Z is 101, Table 102 when Z is 102, Table 103 when Z is 103, Table 104 when Z is 104 and Table 105 when Z is 105, Table 106 when Z is 106, Table 107 when Z is 107, Table 108 when Z is 108, Table 109 when Z is 109, Table 110 when Z is 110, Table 111 when Z is 111, Table 112 when Z is 112, Table 113 when Z is 113, Table 114 when Z is 114 and Table 115 when Z is 115, Table 116 when Z is 116, Table 117 when Z is 117, Table 118 when Z is 118, Table 119 when Z is 119, Table 120 when Z is 120, and Table 121 when Z is 121.

| No. | $R^2$ | Q |
|---|---|---|
| Z.1 | 3,5-dichloro-phenyl | Cl |
| Z.2 | 3,5-dichloro-phenyl | Br |
| Z.3 | 3,5-dichloro-phenyl | I |

-continued

| No. | R² | Q |
|---|---|---|
| Z.4 | 3,5-dichloro-phenyl | F |
| Z.5 | 3,5-dichloro-phenyl | NO₂ |
| Z.6 | 3,5-dichloro-phenyl | NH₂ |
| Z.7 | 3,5-dichloro-phenyl | Cyano |
| Z.8 | 3,5-dichloro-phenyl | —OMe |
| Z.9 | 3,5-dichloro-phenyl | —OEt |
| Z.10 | 3,5-dichloro-phenyl | —OSO₂Me |
| Z.11 | 3,5-dichloro-phenyl | —OSO2CF₃ |
| Z.12 | 3,5-dichloro-phenyl | —OSO₂(p-tolyl) |
| Z.13 | 3,5-dichloro-phenyl | —C(=O)Cl |
| Z.14 | 3,5-dichloro-phenyl | —C(=O)F |
| Z.15 | 3,5-dichloro-phenyl | —C(=O)OH |
| Z.16 | 3,5-dichloro-phenyl | —C(=O)OMe |
| Z.17 | 3,5-dichloro-phenyl | —C(=O)OEt |
| Z.18 | 3,5-dichloro-phenyl | —C(=O)On-Pr |
| Z.19 | 3,5-dichloro-phenyl | —C(=O)Oi-Pr |
| Z.20 | 3,5-dichloro-phenyl | —C(=O)On-Bu |
| Z.21 | 3,5-dichloro-phenyl | —C(=O)Oi-Bu |
| Z.22 | 3,5-dichloro-phenyl | —C(=O)Ot-Bu |
| Z.23 | 3,5-dichloro-phenyl | —C(=O)Oallyl |
| Z.24 | 3,5-dichloro-phenyl | —C(=O)O-benzyl |
| Z.25 | 3,5-dichloro-phenyl | —C(=O)O-(2-pyridine). |
| Z.26 | 3,5-Bis trifluoro methyl-phenyl | Cl |
| Z.27 | 3,5-Bis trifluoro methyl-phenyl | Br |
| Z.28 | 3,5-Bis trifluoro methyl-phenyl | I |
| Z.29 | 3,5-Bis trifluoro methyl-phenyl | F |
| Z.30 | 3,5-Bis trifluoro methyl-phenyl | NO₂ |
| Z.31 | 3,5-Bis trifluoro methyl-phenyl | NH₂ |
| Z.32 | 3,5-Bis trifluoro methyl-phenyl | Cyano |
| Z.33 | 3,5-Bis trifluoro methyl-phenyl | —OMe |
| Z.34 | 3,5-Bis trifluoro methyl-phenyl | —OEt |
| Z.35 | 3,5-Bis trifluoro methyl-phenyl | —OSO₂Me |
| Z.36 | 3,5-Bis trifluoro methyl-phenyl | —OSO2CF₃ |
| Z.37 | 3,5-Bis trifluoro methyl-phenyl | —OSO₂(p-tolyl) |
| Z.38 | 3,5-Bis trifluoro methyl-phenyl | —C(=O)Cl |
| Z.39 | 3,5-Bis trifluoro methyl-phenyl | —C(=O)F |
| Z.40 | 3,5-Bis trifluoro methyl-phenyl | —C(=O)OH |
| Z.41 | 3,5-Bis trifluoro methyl-phenyl | —C(=O)OMe |
| Z.42 | 3,5-Bis trifluoro methyl-phenyl | —C(=O)OEt |
| Z.43 | 3,5-Bis trifluoro methyl-phenyl | —C(=O)On-Pr |
| Z.44 | 3,5-Bis trifluoro methyl-phenyl | —C(=O)Oi-Pr |
| Z.45 | 3,5-Bis trifluoro methyl-phenyl | —C(=O)On-Bu |
| Z.46 | 3,5-Bis trifluoro methyl-phenyl | —C(=O)Oi-Bu |
| Z.47 | 3,5-Bis trifluoro methyl-phenyl | —C(=O)Ot-Bu |
| Z.48 | 3,5-Bis trifluoro methyl-phenyl | —C(=O)Oallyl |
| Z.49 | 3,5-Bis trifluoro methyl-phenyl | —C(=O)O-benzyl |
| Z.50 | 3,5-Bis trifluoro methyl-phenyl | —C(=O)O-(2-pyridine) |
| Z.51 | 3,4,5-Trichloro-phenyl | Cl |
| Z.52 | 3,4,5-Trichloro-phenyl | Br |
| Z.53 | 3,4,5-Trichloro-phenyl | I |
| Z.54 | 3,4,5-Trichloro-phenyl | F |
| Z.55 | 3,4,5-Trichloro-phenyl | NO₂ |
| Z.56 | 3,4,5-Trichloro-phenyl | NH₂ |
| Z.57 | 3,4,5-Trichloro-phenyl | Cyano |
| Z.58 | 3,4,5-Trichloro-phenyl | —OMe |
| Z.59 | 3,4,5-Trichloro-phenyl | —OEt |
| Z.60 | 3,4,5-Trichloro-phenyl | —OSO₂Me |
| Z.61 | 3,4,5-Trichloro-phenyl | —OSO2CF₃ |
| Z.62 | 3,4,5-Trichloro-phenyl | —OSO₂(p-tolyl) |
| Z.63 | 3,4,5-Trichloro-phenyl | —C(=O)Cl |
| Z.64 | 3,4,5-Trichloro-phenyl | —C(=O)F |
| Z.65 | 3,4,5-Trichloro-phenyl | —C(=O)OH |
| Z.66 | 3,4,5-Trichloro-phenyl | —C(=O)OMe |
| Z.67 | 3,4,5-Trichloro-phenyl | —C(=O)OEt |
| Z.68 | 3,4,5-Trichloro-phenyl | —C(=O)On-Pr |
| Z.69 | 3,4,5-Trichloro-phenyl | —C(=O)Oi-Pr |
| Z.70 | 3,4,5-Trichloro-phenyl | —C(=O)On-Bu |
| Z.71 | 3,4,5-Trichloro-phenyl | —C(=O)Oi-Bu |
| Z.72 | 3,4,5-Trichloro-phenyl | —C(=O)Ot-Bu |
| Z.73 | 3,4,5-Trichloro-phenyl | —C(=O)Oallyl |
| Z.74 | 3,4,5-Trichloro-phenyl | —C(=O)O-benzyl |
| Z.75 | 3,4,5-Trichloro-phenyl | —C(=O)O-(2-pyridine) |
| Z.76 | 3,5-dichloro-4-fluoro-phenyl | Cl |
| Z.77 | 3,5-dichloro-4-fluoro-phenyl | Br |
| Z.78 | 3,5-dichloro-4-fluoro-phenyl | I |
| Z.79 | 3,5-dichloro-4-fluoro-phenyl | F |
| Z.80 | 3,5-dichloro-4-fluoro-phenyl | NO₂ |
| Z.81 | 3,5-dichloro-4-fluoro-phenyl | NH₂ |
| Z.82 | 3,5-dichloro-4-fluoro-phenyl | Cyano |
| Z.83 | 3,5-dichloro-4-fluoro-phenyl | —OMe |
| Z.84 | 3,5-dichloro-4-fluoro-phenyl | —OEt |
| Z.85 | 3,5-dichloro-4-fluoro-phenyl | —OSO₂Me |
| Z.86 | 3,5-dichloro-4-fluoro-phenyl | —OSO₂CF₃ |
| Z.87 | 3,5-dichloro-4-fluoro-phenyl | —OSO₂(p-tolyl) |
| Z.88 | 3,5-dichloro-4-fluoro-phenyl | —C(=O)Cl |
| Z.89 | 3,5-dichloro-4-fluoro-phenyl | —C(=O)F |
| Z.90 | 3,5-dichloro-4-fluoro-phenyl | —C(=O)OH |
| Z.91 | 3,5-dichloro-4-fluoro-phenyl | —C(=O)OMe |
| Z.92 | 3,5-dichloro-4-fluoro-phenyl | —C(=O)OEt |
| Z.93 | 3,5-dichloro-4-fluoro-phenyl | —C(=O)On-Pr |
| Z.94 | 3,5-dichloro-4-fluoro-phenyl | —C(=O)Oi-Pr |
| Z.95 | 3,5-dichloro-4-fluoro-phenyl | —C(=O)On-Bu |
| Z.96 | 3,5-dichloro-4-fluoro-phenyl | —C(=O)Oi-Bu |
| Z.97 | 3,5-dichloro-4-fluoro-phenyl | —C(=O)Ot-Bu |
| Z.98 | 3,5-dichloro-4-fluoro-phenyl | —C(=O)Oallyl |
| Z.99 | 3,5-dichloro-4-fluoro-phenyl | —C(=O)O-benzyl |
| Z.100 | 3,5-dichloro-4-fluoro-phenyl | —C(=O)O-(2-pyridine) |
| Z.101 | 3-chloro-5-trifluoro methyl-phenyl | Cl |
| Z.102 | 3-chloro-5-trifluoro methyl-phenyl | Br |
| Z.103 | 3-chloro-5-trifluoro methyl-phenyl | I |
| Z.104 | 3-chloro-5-trifluoro methyl-phenyl | F |
| Z.105 | 3-chloro-5-trifluoro methyl-phenyl | NO₂ |
| Z.106 | 3-chloro-5-trifluoro methyl-phenyl | NH₂ |
| Z.107 | 3-chloro-5-trifluoro methyl-phenyl | Cyano |
| Z.108 | 3-chloro-5-trifluoro methyl-phenyl | —OMe |
| Z.109 | 3-chloro-5-trifluoro methyl-phenyl | —OEt |
| Z.110 | 3-chloro-5-trifluoro methyl-phenyl | —OSO₂Me |
| Z.111 | 3-chloro-5-trifluoro methyl-phenyl | —OSO₂CF₃ |
| Z.112 | 3-chloro-5-trifluoro methyl-phenyl | —OSO₂(p-tolyl) |
| Z.113 | 3-chloro-5-trifluoro methyl-phenyl | —C(=O)Cl |
| Z.114 | 3-chloro-5-trifluoro methyl-phenyl | —C(=O)F |
| Z.115 | 3-chloro-5-trifluoro methyl-phenyl | —C(=O)OH |
| Z.116 | 3-chloro-5-trifluoro methyl-phenyl | —C(=O)OMe |
| Z.117 | 3-chloro-5-trifluoro methyl-phenyl | —C(=O)OEt |
| Z.118 | 3-chloro-5-trifluoro methyl-phenyl | —C(=O)On-Pr |
| Z.119 | 3-chloro-5-trifluoro methyl-phenyl | —C(=O)Oi-Pr |
| Z.120 | 3-chloro-5-trifluoro methyl-phenyl | —C(=O)On-Bu |
| Z.121 | 3-chloro-5-trifluoro methyl-phenyl | —C(=O)Oi-Bu |
| Z.122 | 3-chloro-5-trifluoro methyl-phenyl | —C(=O)Ot-Bu |
| Z.123 | 3-chloro-5-trifluoro methyl-phenyl | —C(=O)Oallyl |
| Z.124 | 3-chloro-5-trifluoro methyl-phenyl | —C(=O)O-benzyl |
| Z.125 | 3-chloro-5-trifluoro methyl-phenyl | —C(=O)O-(2-pyridine) |
| Z.126 | 3-chloro-5-bromo-phenyl | Cl |
| Z.127 | 3-chloro-5-bromo-phenyl | Br |
| Z.128 | 3-chloro-5-bromo-phenyl | I |
| Z.129 | 3-chloro-5-bromo-phenyl | F |
| Z.130 | 3-chloro-5-bromo-phenyl | NO₂ |
| Z.131 | 3-chloro-5-bromo-phenyl | NH₂ |
| Z.132 | 3-chloro-5-bromo-phenyl | Cyano |
| Z.133 | 3-chloro-5-bromo-phenyl | —OMe |
| Z.134 | 3-chloro-5-bromo-phenyl | —OEt |
| Z.135 | 3-chloro-5-bromo-phenyl | —OSO₂Me |
| Z.136 | 3-chloro-5-bromo-phenyl | —OSO₂CF₃ |
| Z.137 | 3-chloro-5-bromo-phenyl | —OSO₂(p-tolyl) |
| Z.138 | 3-chloro-5-bromo-phenyl | —C(=O)Cl |
| Z.139 | 3-chloro-5-bromo-phenyl | —C(=O)F |
| Z.140 | 3-chloro-5-bromo-phenyl | —C(=O)OH |
| Z.141 | 3-chloro-5-bromo-phenyl | —C(=O)OMe |
| Z.142 | 3-chloro-5-bromo-phenyl | —C(=O)OEt |
| Z.142 | 3-chloro-5-bromo-phenyl | —C(=O)On-Pr |
| Z.143 | 3-chloro-5-bromo-phenyl | —C(=O)Oi-Pr |
| Z.144 | 3-chloro-5-bromo-phenyl | —C(=O)On-Bu |
| Z.145 | 3-chloro-5-bromo-phenyl | —C(=O)Oi-Bu |
| Z.146 | 3-chloro-5-bromo-phenyl | —C(=O)Ot-Bu |
| Z.147 | 3-chloro-5-bromo-phenyl | —C(=O)Oallyl |
| Z.148 | 3-chloro-5-bromo-phenyl | —C(=O)O-benzyl |
| Z.149 | 3-chloro-5-bromo-phenyl | —C(=O)O-(2-pyridine) |

Table 67

Table 67 discloses compounds 671.1 to 67.149 of the formula I-aa

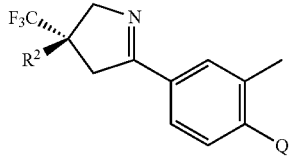

(I-aa)

wherein R² and Q have the values given in the Table

Table 68

Table 68 discloses compounds 68.1 to 68.149 of the formula I-bb

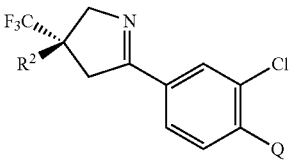

(I-bb)

wherein R² and Q have the values given in the Table

Table 69

Table 69 discloses compounds 69.1 to 69.149 of the formula I-cc

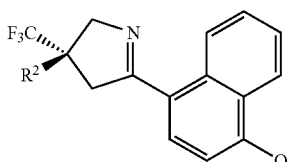

(I-cc)

wherein R² and Q have the values given in the Table

Table 70

Table 70 discloses compounds 70.1 to 70.149 of the formula I-dd

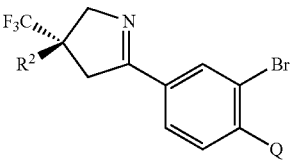

(I-dd)

wherein R² and Q have the values given in the Table

Table 71

Table 71 discloses compounds 71.1 to 71.149 of the formula I-ee

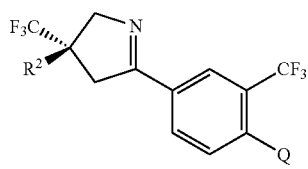

(I-ee)

wherein R² and Q have the values given in the Table

Table 72

Table 72 discloses compounds 72.1 to 72.149 of the formula III-aa

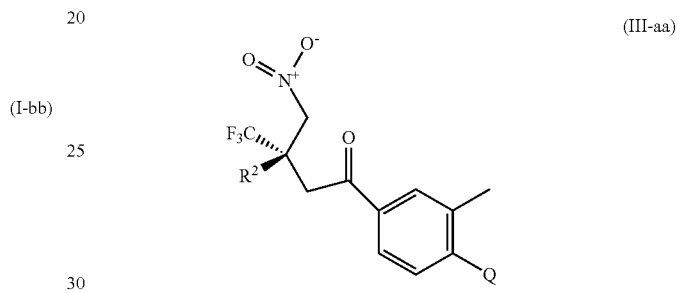

(III-aa)

wherein R² and Q have the values given in the Table

Table 73

Table 73 discloses compounds 73.1 to 73.149 of the formula III-bb

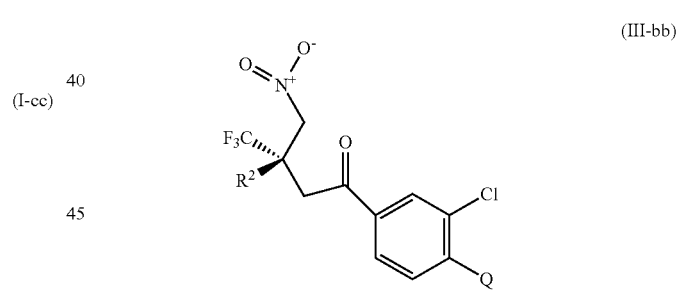

(III-bb)

wherein R² and Q have the values given in the Table

Table 74

Table 74 discloses compounds 74.1 to 74.149 of the formula III-cc

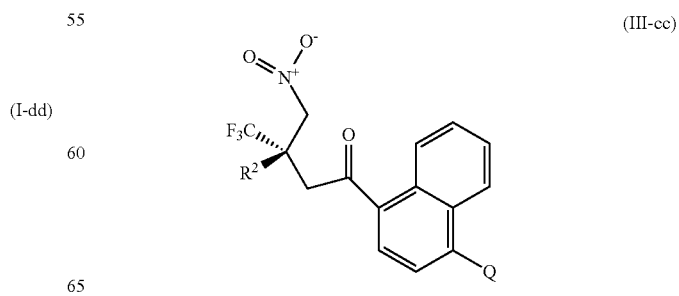

(III-cc)

wherein R² and Q have the values given in the Table

Table 75
Table 75 discloses compounds 75.1 to 75.149 of the formula III-dd

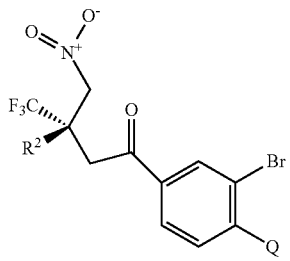
(III-dd)

wherein R² and Q have the values given in the Table

Table 76
Table 76 discloses compounds 76.1 to 76.149 of the formula III-ee

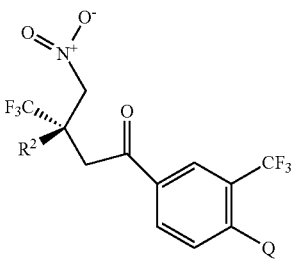
(III-ee)

wherein R² and Q have the values given in the Table

Table 77
Table 77 discloses compounds 77.1 to 77.149 of the formula IV-aa

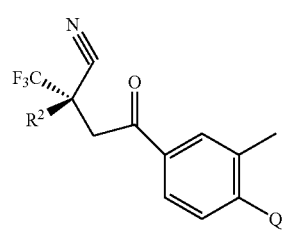
(IV-aa)

wherein R² and Q have the values given in the Table

Table 78
Table 78 discloses compounds 78.1 to 78.149 of the formula IV-bb

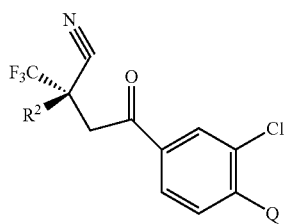
(IV-bb)

wherein R² and Q have the values given in the Table

Table 79
Table 79 discloses compounds 79.1 to 79.149 of the formula IV-cc

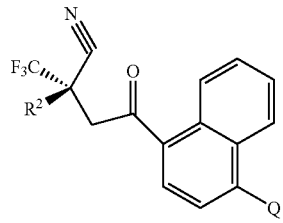
(IV-cc)

wherein R² and Q have the values given in the Table

Table 80
Table 80 discloses compounds 80.1 to 80.149 of the formula IV-dd

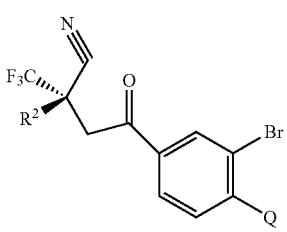
(IV-dd)

wherein R² and Q have the values given in the Table

Table 81
Table 81 discloses compounds 81.1 to 81.149 of the formula IV-ee (IV-ee)

wherein R² and Q have the values given in the Table

Table 82
Table 82 discloses compounds 82.1 to 82.149 of the formula II-aa1

(II-aa1)

wherein R² and Q have the values given in the Table and R¹ is CF₃

Table 83
Table 83 discloses compounds 83.1 to 837.149 of the formula II-aa2

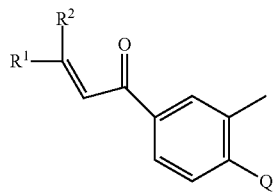
(II-aa2)

wherein $R^2$ and Q have the values given in the Table and $R^1$ is $CF_3$

Table 84
Table 84 discloses compounds 84.1 to 84.149 of the formula II-bb1

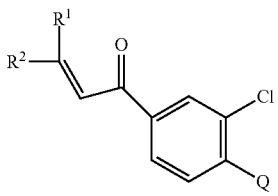
(II-bb1)

wherein $R^2$ and Q have the values given in the Table and $R^1$ is $CF_3$

Table 85
Table 85 discloses compounds 85.1 to 85.149 of the formula II-bb2

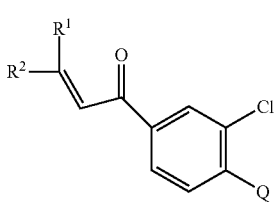
(II-bb2)

wherein $R^2$ and Q have the values given in the Table and $R^1$ is $CF_3$

Table 86
Table 50 discloses compounds 86.1 to 86.149 of the formula II-cc1

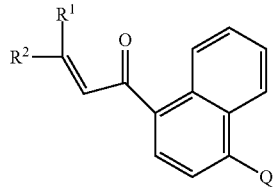
(II-cc1)

wherein $R^2$ and Q have the values given in the Table and $R^1$ is $CF_3$

Table 87
Table 87 discloses compounds 87.1 to 87.149 of the formula II-cc2

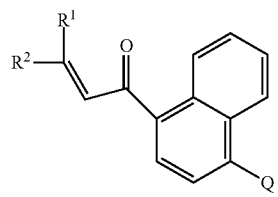
(II-cc2)

wherein $R^2$ and Q have the values given in the Table and $R^1$ is $CF_3$

Table 88
Table 88 discloses compounds 88.1 to 88.149 of the formula II-dd1

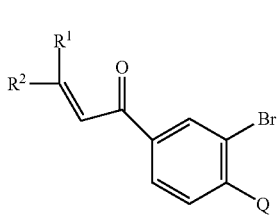
(II-dd1)

wherein $R^2$ and Q have the values given in the Table and $R^1$ is $CF_3$

Table 89
Table 89 discloses compounds 89.1 to 89.149 of the formula II-dd2

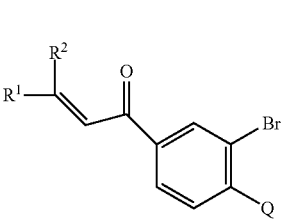
(II-dd2)

wherein $R^2$ and Q have the values given in the Table and $R^1$ is $CF_3$

Table 90
Table 90 discloses compounds 90.1 to 90.149 of the formula II-ee1

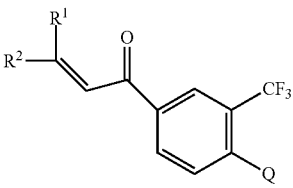
(II-ee1)

wherein $R^2$ and Q have the values given in the Table and $R^1$ is $CF_3$

Table 91

Table 91 discloses compounds 91.1 to 91.149 of the formula II-ee2

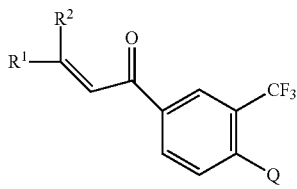
(II-ee2)

wherein $R^2$ and Q have the values given in the Table and $R^1$ is $CF_3$

Table 92

Table 92 discloses compounds 92.1 to 92.138 of the formula XXIII-aa1

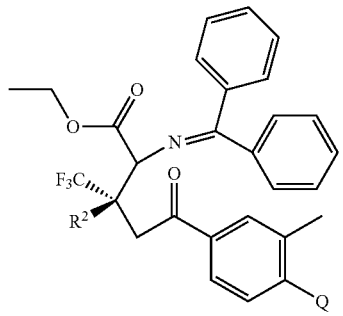
(XXIII-aa1)

wherein $R^2$ and Q have the values given in the Table

Table 93

Table 93 discloses compounds 93.1 to 93.138 of the formula XXIII-bb1

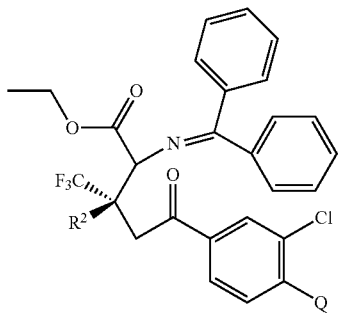
(XXIII-bb1)

wherein $R^2$ and Q have the values given in the Table

Table 94

Table 94 discloses compounds 94.1 to 94.138 of the formula XXIII-cc1

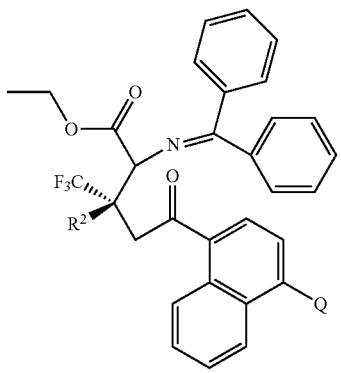
(XXIII-cc1)

wherein $R^2$ and Q have the values given in the Table

Table 95

Table 95 discloses compounds 95.1 to 95.138 of the formula XXIII-dd1

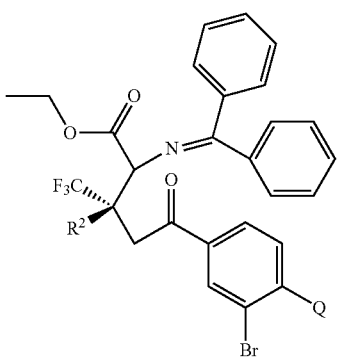
(XXIII-dd1)

wherein $R^2$ and Q have the values given in the Table

Table 96

Table 96 discloses compounds 96.1 to 96.138 of the formula XXIII-ee1

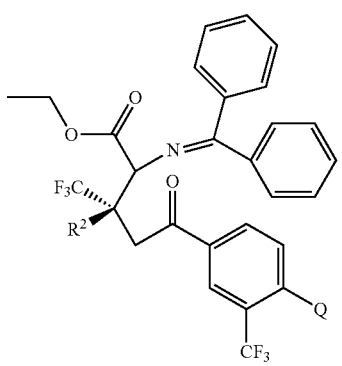
(XXIII-ee1)

wherein $R^2$ and Q have the values given in the Table

Table 97

Table 97 discloses compounds 97.1 to 97.138 of the formula XXIII-aa2

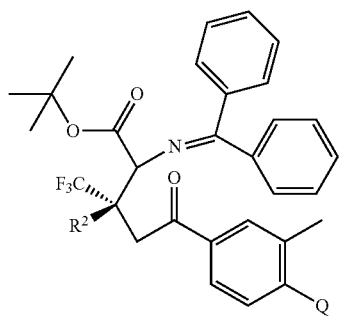
(XXIII-aa2)

wherein R² and Q have the values given in the Table

Table 98

Table 98 discloses compounds 98.1 to 98.138 of the formula XXIII-bb2

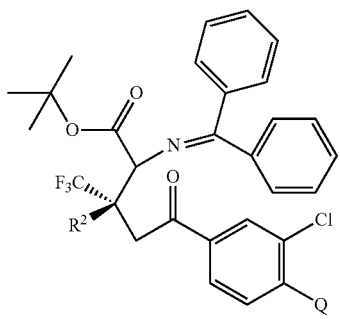
(XXIII-bb2)

wherein R² and Q have the values given in the Table

Table 99

Table 99 discloses compounds 99.1 to 99.138 of the formula XXIII-cc2

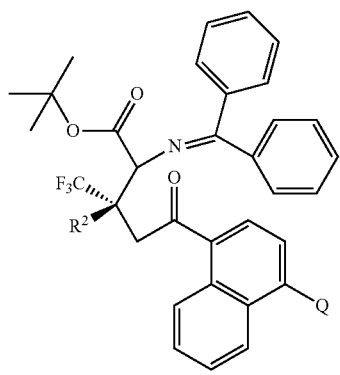
(XXIII-cc2)

wherein R² and Q have the values given in the Table

Table 100

Table 100 discloses compounds 100.1 to 100.138 of the formula XXIII-dd2

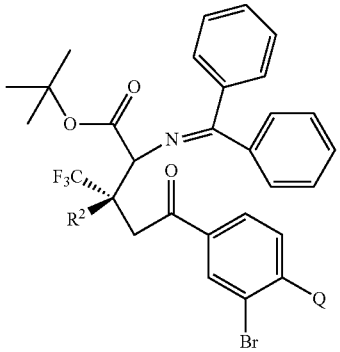
(XXIII-dd2)

wherein R² and Q have the values given in the Table

Table 101

Table 101 discloses compounds 101.1 to 101.138 of the formula XXIII-ee2

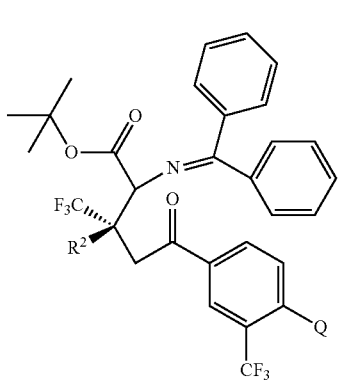
(XXIII-ee2)

wherein R² and Q have the values given in the Table

Table 102

Table 102 discloses compounds 102.1 to 102.138 of the formula XXIII-aa3

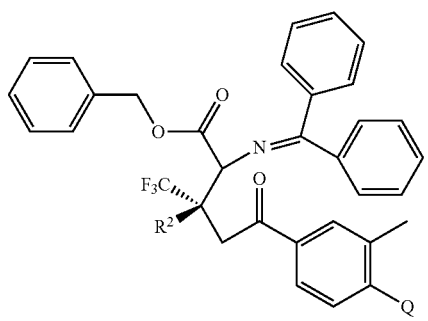
(XXIII-aa3)

wherein R² and Q have the values given in the Table

Table 103

Table 103 discloses compounds 103.1 to 103.138 of the formula XXIII-bb3

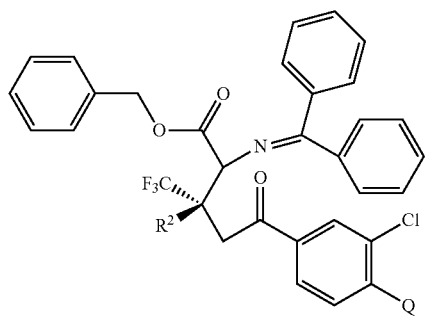
(XXIII-bb3)

wherein R² and Q have the values given in the Table

Table 104

Table 104 discloses compounds 104.1 to 104.138 of the formula XXIII-cc3

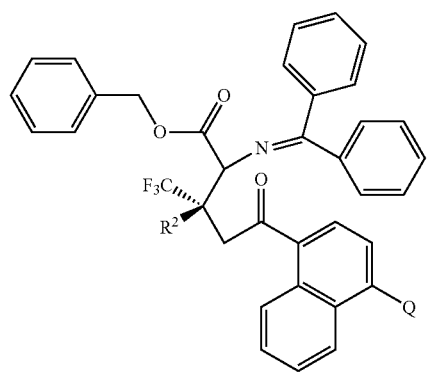
(XXIII-cc3)

wherein R² and Q have the values given in the Table

Table 105

Table 105 discloses compounds 105.1 to 105.138 of the formula XXIII-dd3

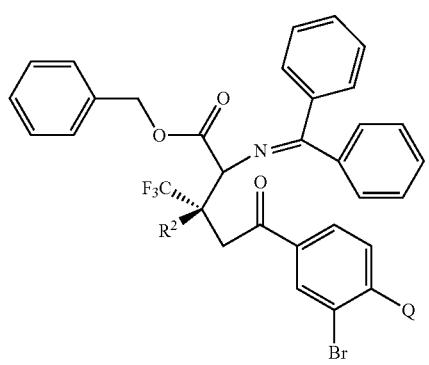
(XXIII-dd3)

wherein R² and Q have the values given in the Table

Table 106

Table 106 discloses compounds 106.1 to 106.138 of the formula XXIII-ee3

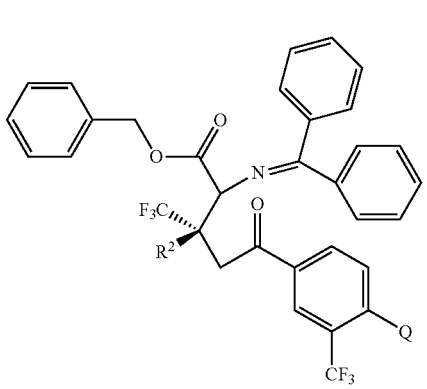
(XXIII-ee3)

wherein R² and Q have the values given in the Table

Table 107

Table 107 discloses compounds 107.1 to 107.138 of the formula XXIV-aa1

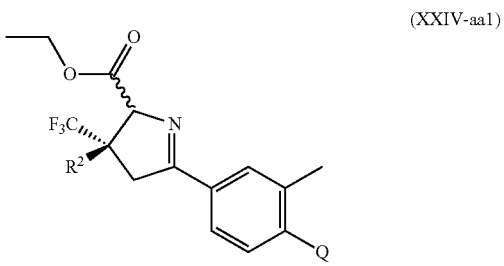
(XXIV-aa1)

wherein R² and Q have the values given in the Table

Table 108

Table 108 discloses compounds 108.1 to 108.138 of the formula XXIV-bb1

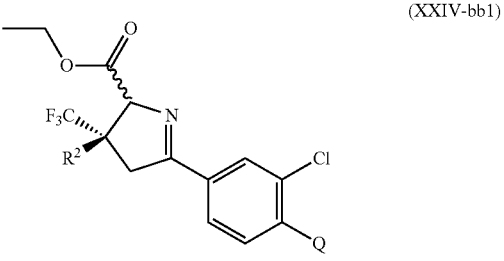
(XXIV-bb1)

wherein R² and Q have the values given in the Table

Table 109

Table 109 discloses compounds 109.1 to 109.138 of the formula XXIV-cc1

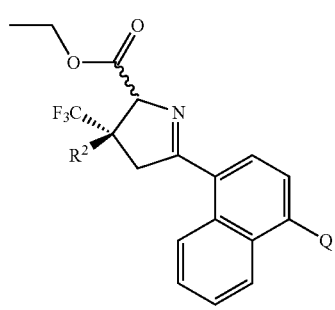
(XXIV-cc1)

wherein R² and Q have the values given in the Table

Table 110

Table 110 discloses compounds 110.1 to 110.138 of the formula XXIV-dd1

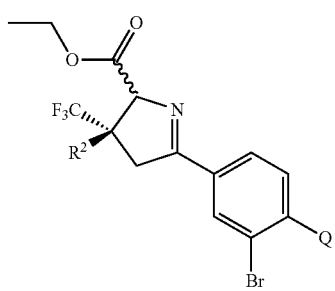
(XXIV-dd1)

wherein R² and Q have the values given in the Table

Table 111

Table 111 discloses compounds 111.1 to 111.138 of the formula XXIV-ee1

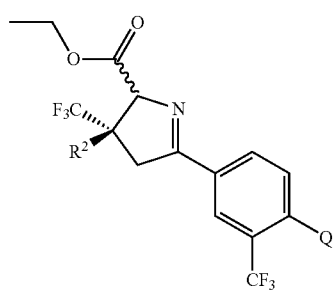
(XXIV-ee1)

wherein R² and Q have the values given in the Table

Table 112

Table 112 discloses compounds 112.1 to 112.138 of the formula XXIV-aa2

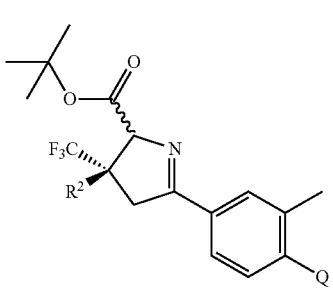
(XXIV-aa2)

wherein R² and Q have the values given in the Table

Table 113

Table 113 discloses compounds 113.1 to 113.138 of the formula XXIV-bb2

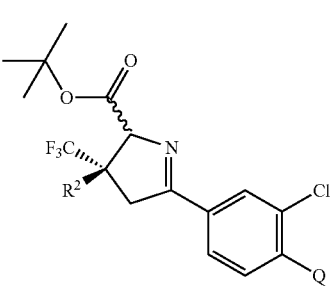
(XXIV-bb2)

wherein R² and Q have the values given in the Table

Table 114

Table 114 discloses compounds 114.1 to 114.138 of the formula XXIV-cc2

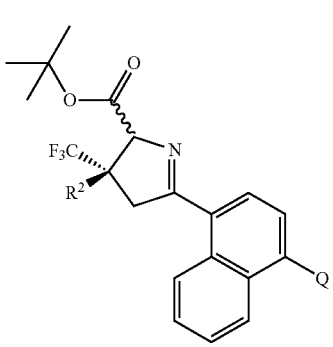
(XXIV-cc2)

wherein R² and Q have the values given in the Table

Table 115

Table 115 discloses compounds 115.1 to 115.138 of the formula XXIV-dd2

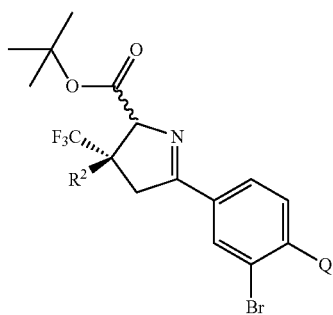
(XXIV-dd2)

wherein R² and Q have the values given in the Table

Table 116

Table 116 discloses compounds 116.1 to 116.138 of the formula XXIV-ee2

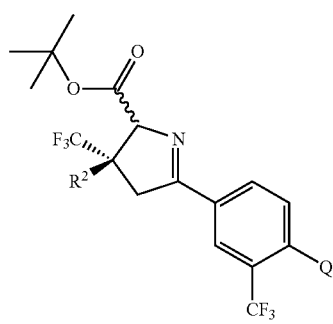
(XXIV-ee2)

wherein R² and Q have the values given in the Table

Table 117

Table 117 discloses compounds 117.1 to 117.138 of the formula XXIV-aa3

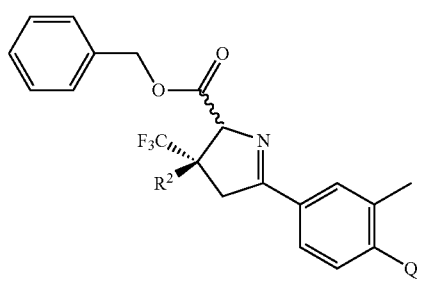
(XXIV-aa3)

wherein R² and R⁷ have the values given in the Table

Table 118

Table 118 discloses compounds 118.1 to 118.138 of the formula XXIV-bb3

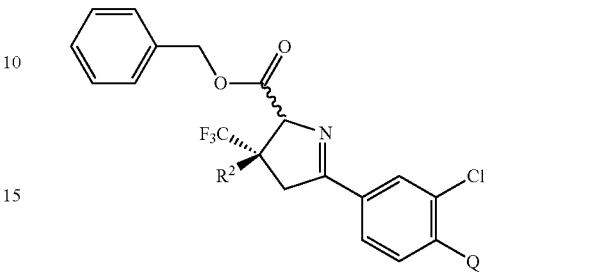
(XXIV-bb3)

wherein R² and Q have the values given in the Table

Table 119

Table 119 discloses compounds 119.1 to 119.138 of the formula XXIV-cc3

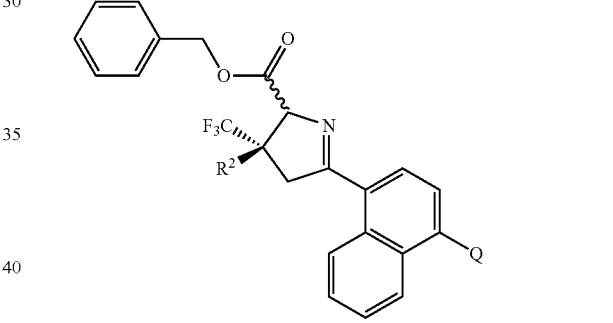
(XXIV-cc3)

wherein R² and Q have the values given in the Table

Table 120

Table 120 discloses compounds 120.1 to 120.138 of the formula XXIV-dd3

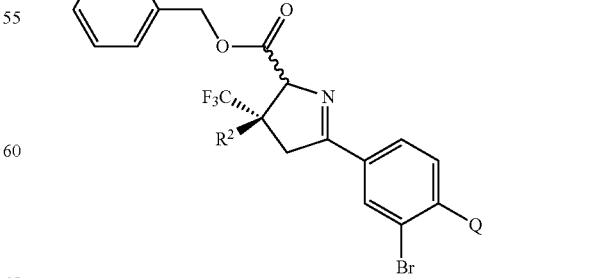
(XXIV-dd3)

wherein R² and Q have the values given in the Table

Table 121

Table 121 discloses compounds 121.1 to 121.138 of the formula XXIV-ee3

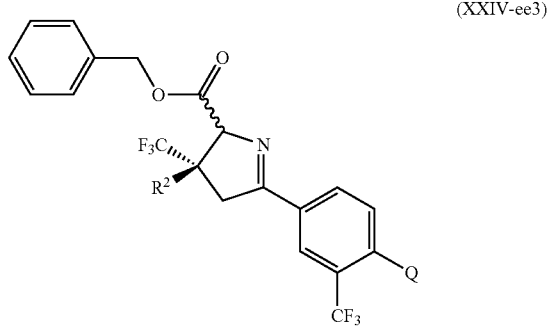

wherein $R^2$ and Q have the values given in the Table

Procedures for carrying out the processes of the invention and reaction suitable reaction conditions are described in more detail below.

Scheme 1 illustrates process (a).

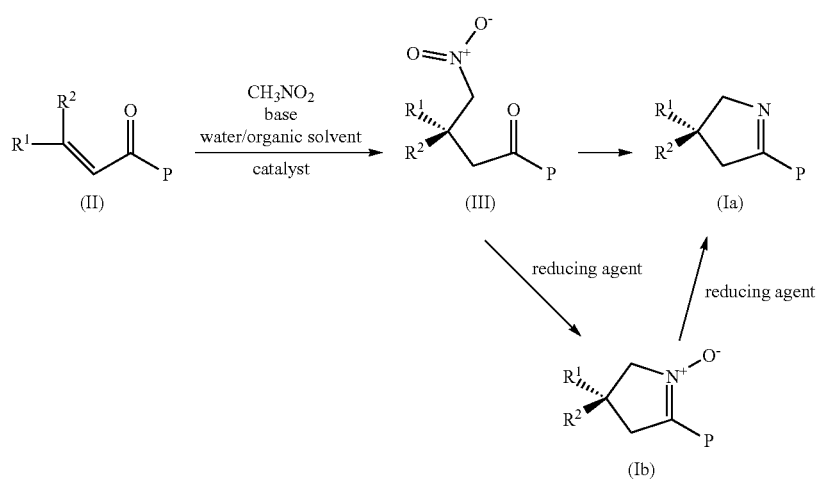

1) Enantioenriched compounds of formula (III) can be prepared by reacting a compound of formula (II) with nitromethane in the presence of a chiral catalyst. In most cases it is advantageous to conduct the reaction using nitromethane as a solvent at dilution between 0.1 M to 1 M, preferably 0.3 M to 0.5 M. Alternatively suitable organic solvents could be used, for example toluene, 1,2-dichloroethane, dichloromethane, tetrahydrofuran, methanol or ethyl acetate at a temperature from 0° C. to 100° C., preferably between 40 and 100° C., and at dilution of e.g. between 0.1 M to 1 M. The reaction time is usually between 12 and 96 hours, preferably between 24 and 72 hours. The amount of catalyst is usually between 0.02 and 0.2 molar equivalents, preferably between 0.05 and 0.1 molar equivalents. If a solvent other than nitromethane is used, the amount of nitromethane added is between 1.5 and 20 molar equivalents, preferably between 1.5 and 5 molar equivalents. Reaction with some chiral catalysts, notably bifunctional thiourea or urea catalysts, do not require any additives. In most other cases, however, it is necessary or useful to add a base to the reaction media. Suitable bases include amines, such as triethylamine, 2,5-dimethylpiperazine, tetramethylpiperidine, 4-dimethylamino pyridine, metal alkoxides, such as sodium t-butoxide, metal carbonates, such as potassium carbonate or metal fluorides, such as cesium fluoride or cesium chloride. In some instances an additional proton source such as 4-nitrophenol or t-butanol is needed or useful. If phase transfer catalysts of group I are used, the addition of small amounts of water (1-4 molar equivalents) is often beneficial.

2) Compounds of formula (I) can be prepared by reducing and cyclizing compounds of formula (III). Suitable reducing agents include iron and zinc in the presence of a strong acid, Raney nickel under the atmosphere of hydrogen or a mixture of titanium (IV) chloride with zinc or titanium (III) chloride. A reduction with Raney nickel is performed in suitable alcoholic solvents, such as methanol or ethanol, at temperatures from 20° C. to 60° C. Hydrogen pressure used is from 1 bar to 20 bar and the amount of catalyst used is between 5 and 20 weight percent. The reaction time is usually between 10 min and 6 hours, preferably between 30 min and 2 hours. The extent of reduction could potentially be controlled by varying temperature and pressure of hydrogen. A reduction with zinc and acid is carried out in suitable polar solvents, such as dimethylformamide, which are miscible with water. The pH of a solution is kept at 1-2 and the amount of zinc powder used is between 2 and 10 molar equivalents, preferably between 2 and 4 molar equivalents. The reaction time is usually between 30 min and 4 hours, preferably between 30 min and 2 hours.

3) Compounds of formula (Ib) could be formed by partial reduction followed by cyclization of compounds of formula (III). A suitable method is a reduction with nickel borohydride made in situ from sodium borohydride and nickel (II) chloride or a reduction with zinc powder in the presence of a mild acid. A reduction with nickel borohydride is carried out by adding sodium borohydride to a solution of compound of formula (III) and nickel (II) chloride in a suitable protic solvent, such as methanol. The amount of nickel chloride used is between 1 and 2 molar equivalents, preferably 1 molar equivalent. The amount of sodium borohydride used is between 3 and 15 molar equivalents, preferably between 3 and 8 molar equivalents. The reaction temperature is kept between −20° C. and +20° C., preferably 0° C. The reaction time is between 10 min and 1 hour, preferably between 10 min and 20 min. The reduction with zinc and acid is carried out in suitable polar solvents, such as dimethylformamide, which are miscible with water. The pH of a solution is kept at 4-7 and the amount of zinc powder used is between 2 and 10 molar equivalents, preferably between 2 and 4 molar equivalents. The reaction time is usually between 30 min and 4 hours, preferably between 30 min and 2 hours.

4) Compounds of formula (Ia) could be formed by a reduction of compounds of formula (Ib). Suitable reagents for this transformation include trialkyl phosphines, for example tributylphosphine; or benzyltriethylammonium tetrathiomolybdate. Other suitable reducing agents include iron and zinc in the presence of a strong acid, Raney nickel under the atmosphere of hydrogen or a mixture of titanium (IV) or titanium (III) chloride with zinc. The reduction with trialkyl phosphines is carried out by adding a trialkylphosphine, such as tributylphosphine, to a solution of compound of formula (Ib) in a suitable polar solvent, such as THF or diethylether. The reaction times are usually between 6 hours and 72 hours and the reaction temperature is between 20° C. and 70° C. The amount of trialkylphosphine used is between 1 and 3 molar equivalents, preferably 1 molar equivalent. A reduction with zinc and acid is carried out in suitable polar solvents, such as dimethylformamide, which are miscible with water. The pH of a solution is kept at 1-2 and the amount of zinc powder used is between 2 and 5 molar equivalents, preferably between 2 and 3 molar equivalents. The reaction time is usually between 30 min and 4 hours, preferably between 30 min and 2 hours. A reduction with benzyltriethylammonium tetrathiomolybdate is carried out by adding the reducing agent to compound of formula (Ib) in a suitable polar organic solvent, such as acetonitrile. The amount of benzyltriethylammonium tetrathiomolybdate used is between 1 and 2 molar equivalents, preferably 1 molar equivalent. The reaction is usually conducted at ambient temperature and the reaction time is usually between 12 and 90 hours.

Scheme 2 illustrates process (b).

Scheme 2

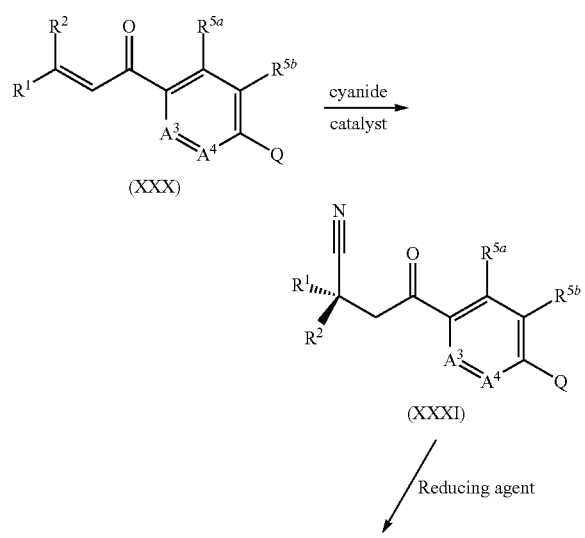

(XXX)

(XXXI)

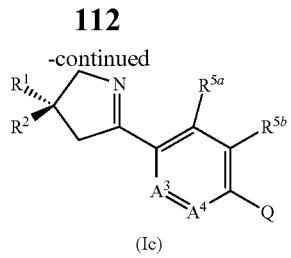

(Ic)

5) Enantioenriched compounds of formula (XXXI) can be prepared by reacting a compound of formula (XXX) with a suitable cyanide source in the presence of a chiral catalyst. Suitable cyanide sources include, but are not limited to alkali metal cyanides, trimethylsilyl and tert-butyldimethylsilyl cyanides, hydrogen cyanide, $CNCO_2Et$ and acetone cyanohydrin. Depending from the catalyst used, suitable solvents include dioxane, tetrahydrofuran, dichloromethane, t-butyl-methyl ether, 1,2-dichloroethane, dimethoxyethane, xylenes and toluene. In certain cases additives such as cesium fluoride, cesium chloride, lithium phenolate or 2,6-dimethylphenol are often required. In most cases it is advantageous to conduct the reaction in a suitable solvent at dilution between 0.1 M to 1 M, preferably 0.3 M to 0.5 M. The reaction temperature could be from −40° C. to 100° C., preferably between −20° C. and 50° C. The reaction time is usually between 1 hour and 96 hours, preferably between 6 hours and 24 hours. The amount of catalyst is usually between 0.02 and 0.2 molar equivalents, preferably between 0.05 and 0.1 molar equivalents. Certain catalysts require a presence of a Lewis acid, such as galodinium trifluoromethansulfonate or strontium trifluoromethanesulfonate.

If chiral phase transfer catalysts of group I are used the addition of small amounts of water (between one and four molar equivalents) is often beneficial. Conducting the reaction in a biphasic system (water/suitable organic solvent) is, however, usually detrimental to chemical reactivity.

6) Enantioenriched compounds of formula (Ic) can be prepared by reaction of compounds of formula (XXXI) with a suitable reducing reagent. The most suitable, but not exclusive, method is hydrogenation in the presence of Raney Ni. The most useful solvents are alcohols such as methanol or ethanol and in most cases it is advantageous to conduct the reaction at dilution between 0.1 M to 1 M, preferably 0.3 M to 0.5 M. The amount of catalyst added is usually between 1 molar equivalent and 50 molar equivalents and the reaction time in most cases is between 1 hour and 6 hours.

Although scheme 2 depicts synthesis of compounds of formula (Ic), the skilled person will understand that the conditions described in paragraphs 5 and 6 are also applicable for synthesis of compounds of formula (I) according to process (b) as described in the claims.

Scheme 3 illustrates process (c).

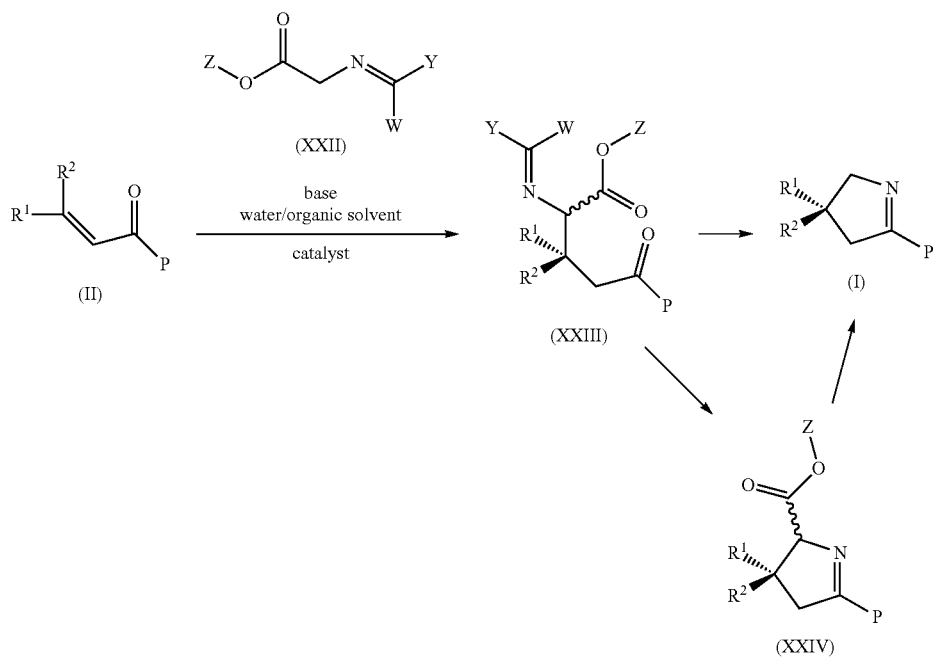

7) Enantioenriched compounds of formula (XXIII) wherein P, $R^1$ and $R^2$ are as defined for the compound of formula I, and Y and W are as defined above, can be prepared by reacting a compound of formula (II) with a glycine Schiff base of formula (XXII), in the presence of a chiral catalyst. In most cases it is advantageous to conduct the reaction using a solvent at a dilution of 0.1 M to 1 M, preferably 0.3 M to 0.5 M. Suitable organic solvents could be used, for example toluene, 1,2-dichloroethane, dichloromethane, tetrahydrofuran, methanol or ethyl acetate. The reaction temperature is usually between 0° C. to 100° C., preferably between 40 and 100° C. When a solvent is used the reacants are usually at a dilution of e.g. between 0.1 M to 1 M. The reaction time is usually between 12 and 96 hours, preferably between 24 and 72 hours. The amount of catalyst is usually between 0.02 and 0.2 molar equivalents, preferably between 0.05 and 0.1 molar equivalents. Reaction with some chiral catalysts, notably bifunctional thiourea or urea catalysts, do not require any additives. In most other cases, however, it is necessary or useful to add a base to the reaction media. Suitable bases include amines, such as triethylamine, 2,5-dimethylpiperazine, tetramethylpiperidine, 4-dimethylamino pyridine, potassium carbonate, metal alkoxides, such as sodium t-butoxide or metal fluorides, such as cesium fluoride. In some instances an additional proton source such as 4-nitrophenol or t-butanol is needed or useful. When process (c) is used to produce racemic mixtures of compounds of formula (I). No chiral catalyst need be used.

8) Compounds of formula (XXIV) can be prepared by deprotecting and cyclizing compounds of formula (XXIII). Suitable conditions for this transformation include acidic conditions, for instance the presence of strong acids such as trifluoroacetic acid, sulfonic acid or hydrochloric acid. Suitable solvents can be used, for example acetone, dimethylsulfoxide, dimethylformamide, toluene, xylenes, 1,2-dichloroethane, dichloromethane, tetrahydrofuran, methanol ethanol, tert-butanol, water or ethyl acetate at a temperature from 0° C. to 140° C., preferably between 0° C. and 80° C., and at dilution of e.g. between 0.1 M to 1 M. The reaction time is usually between 1 and 24 hours, preferably between 1 and 6 hours.

9) Alternatively, compounds of formula (I) can be prepared by decarboxylating compounds of formula (XXIV). Suitable conditions for this transformation involve heating the compounds in a suitable media, which depending on the group Z may include some standard additives known by a person skilled in the art. Suitable solvents can be used, for example acetone, dimethylsulfoxide, dimethylformamide, toluene, xylenes, 1,2-dichloroethane, dichloromethane, tetrahydrofuran, methanol ethanol, tert-butanol, water or ethyl acetate. The temperature is usually between 0° C. and 200° C., preferably between 50 and 180° C. Where a solvent is used, the reactants are usually at dilution of e.g. between 0.1 M to 1M. The reaction time is usually between 12 and 96 hours, preferably between 24 and 72 hours. The reaction can also be performed under microwave conditions, preferably between 40 and 100° C., In some cases, however, it is necessary or useful to add an additive, such as a metal halide, for instance sodium chloride or potassium iodide, or a metal cyanide, such as sodium cyanide to the reaction media, or a base (e.g. when group Z is alkyl). In the case where Z is aryl-methylene (e.g. benzyl), suitable deprotection conditions include hydrogenation conditions. The most useful solvents are alcohols such as methanol or ethanol and in most cases it is advantageous to conduct the reaction at dilution between 0.1 M to 1 M, preferably 0.3 M to 0.5 M. The amount of catalyst, such as palladium on charcoal added is usually between 1 molar equivalent and 50 molar equivalents and the reaction time in most cases is between 1 hour and 6 hours.

10) Compounds of formula (I) can be prepared by deprotecting, decarboxylating and cyclizing compounds of formula (XXIII) according to a one-pot stepwise procedure without isolating the intermediates. Suitable conditions for this transformation include acidic conditions, for instance the presence of strong acids such as trifluoroacetic acid or hydrochloric acid, or basic conditions, depending on the group Z. Suitable solvents could be used, for example acetone, dimethylsulfoxide, dimethylformamide, toluene, xylenes, 1,2-dichloroethane, dichloromethane, tetrahydrofuran, methanol ethanol, tert-butanol, water or ethyl acetate. The temperature is usually between 0° C. and 200° C., preferably between 50 and 180° C. Where a solvent is used the reactants are usually at dilution of e.g. between 0.1 M to 1M. The reaction time is usually between 1 and 96 hours, preferably between 1 and 12 hours. The reaction can also be performed under microwave conditions, preferably between 40 and 100° C., In some cases, however, it is necessary or useful to add an additive, such as a metal halide, for instance sodium chloride or potassium iodide, or a metal cyanide, such as sodium cyanide to the reaction media.

Scheme 4 illustrates process (d).

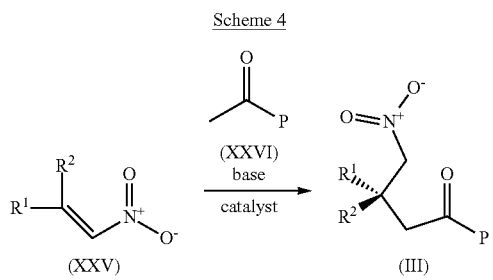

acetophenone of formula (XXVI) in the presence of a chiral catalyst. Compound of formula (XXV) are known in the literature or can be prepared using methods known to a person skilled in the art (see for example Journal of the American Chemical Society (2008), 130(42), 13862-13863) and compounds of formula (XXVI) are known in the literature or can be prepared using methods known to a person skilled in the art (see for example WO2009/080250). In most cases it is advantageous to conduct the reaction using suitable organic solvents, for example toluene, 1,2-dichloroethane, dichloromethane, tetrahydrofuran, methanol or ethyl acetate. The temperature is usually between 0° C. and 100° C., preferably between 40 and 100° C. Where a solvent is used the reactants are usually at a dilution of e.g. between 0.1 M to 1 M. The reaction time is usually between 1 and 96 hours, preferably between 1 and 24 hours. The amount of catalyst is usually between 0.02 and 0.2 molar equivalents, preferably between 0.05 and 0.1 molar equivalents. Reaction with some chiral catalysts, notably bifunctional thiourea or urea catalysts, do not require any additives. In some cases, however, it is necessary or useful to add an acid to the reaction media. Suitable acids are benzoic acids. In some instances an additional proton source such as 4-nitrophenol, phenols, naphthalenol or t-butanol is needed or useful. When process (d) is used to produce racemic mixtures of compounds of formula (I) no chiral catalyst need be used.

12) Compounds of formula III can be converted into compound of formula I using the methodology described under scheme 1.

Scheme 5 indicates the utility of compounds of formula V and VI in the preparation of biologically active compounds.

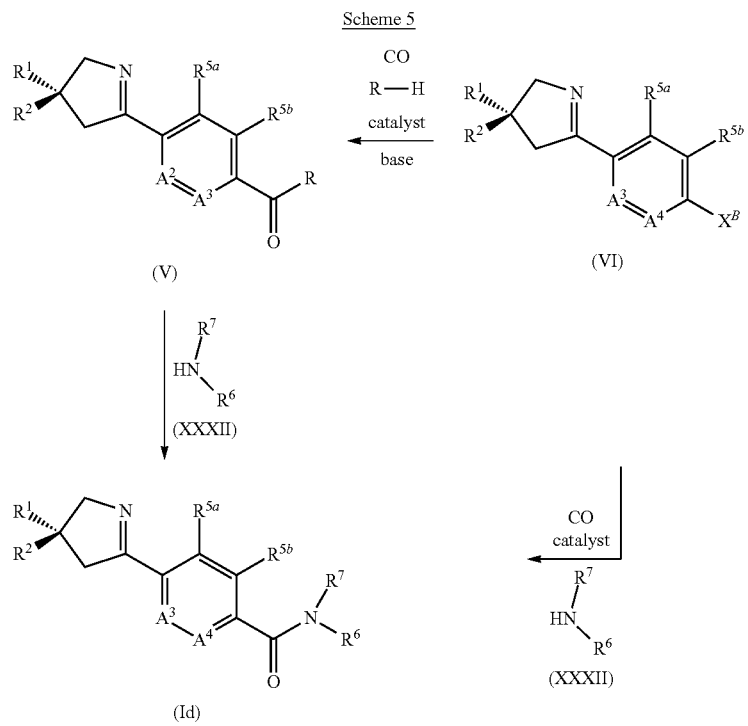

11) Enantioenriched compounds of formula (III) can be prepared by reacting a compound of formula (XXV) with an 13) Compounds of formula (Id) can be prepared by reacting a compound of formula (V) wherein R is OH, C₁-C₆alkoxy or Cl, F or Br, with an amine of formula (XXXII) as shown in Scheme 5. When R is OH such reactions are usually carried out in the presence of a coupling reagent, such as N,N'-dicyclohexylcarbodiimide ("DCC"), 1-ethyl-3-(3-dimethyl-amino-propyl)carbodiimide hydrochloride ("EDC") or bis(2-oxo-3-oxazolidinyl)phosphonic chloride ("BOP—Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is C₁-C₆alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (XXXII) are known in the literature or can be prepared using methods known to a person skilled in the art (see for example WO2010/020522).

14) Acid halides of formula (V), wherein R is Cl, F or Br, may be made from carboxylic acids of formula (V), wherein R is OH, under standard conditions, such as treatment with thionyl chloride or oxalyl chloride. A preferred solvent is dichloromethane. The reaction is carried out at a temperature of from 0° C. to 100° C., preferably from 15° C. to 30° C., in particular at ambient temperature.

15) Carboxylic acids of formula (V), wherein R is OH, may be formed from esters of formula (V) and R is C₁-C₆alkoxy. It is known to a person skilled in the art that there are many methods for the hydrolysis of such esters depending on the nature of the alkoxy group. One widely used method to achieve such a transformation is the treatment of the ester with an alkali hydroxide, such as lithium hydroxide, sodium hydroxide or potassium hydroxide, in a solvent, such as ethanol or tetrahydrofuran, in the presence of water. Another is the treatment of the ester with an acid, such as trifluoroacetic acid, in a solvent, such as dichloromethane, followed by addition of water. The reaction is carried out at a temperature of from 0° C. to 150° C., preferably from 15° C. to 100° C., in particular at 50° C.

16) Compounds of formula (V) wherein R is C₁-C₆alkoxy, can be prepared by reacting a compound of formula (VI) wherein $X^B$ is a leaving group, for example a halogen, such as bromo, with carbon monoxide and an alcohol of formula R—OH, such as ethanol, in the presence of a catalyst, such as bis(triphenylphosphine)palladium(II) dichloride, and a base, such as pyridine, triethylamine, 4-(dimethylamino)-pyridine ("DMAP") or diisopropyl-ethylamine (Hunig's base). The reaction is carried out at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar.

17) Alternatively, compounds of formula (Id) can be prepared by reacting a compound of formula (VI) wherein $X^B$ is a leaving group, for example a halogen, such as bromo, with carbon monoxide and an amine of formula (XXXII), in the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

In the description accompanying schemes 1-5, where a reaction condition, e.g. temperature, time, concentration, is given as a range, e.g. value X to value Y, the skilled person will understand that these values serve as guidelines and that it may in some cases be possible to perform the reactions outside the given values.

Compounds of formula (I) include biologically active compounds (e.g. when Q is —C(=O)N(R⁶)R⁷, —C(R¹⁵)(R¹⁶)N(R¹⁷)R¹⁸, or a heterocycle selected from H1 to H9). Such compounds can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The biologically active compounds of the invention may be used for example on turf, ornamentals, such as flowers, shrubs, broad-leaved trees or evergreens, for example conifers, as well as for tree injection, pest management and the like.

Examples of pest species which may be controlled by the biologically active compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example

*Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of controlling insects, acarines, nematodes or molluscs which comprises applying an insecticidally, acaricidally, nematicidally or molluscicidally effective amount of a compound of formula (I) (when Q is $-C(=O)N(R^6)R^7$, $-C(R^{15})(R^{16})N(R^{17})R^{18}$, or a heterocycle selected from H1 to H9) or a composition containing such a compound of formula (I), including mixtures comprising a compound of formula I and a compound of formula IA that is enriched in the compound of formula I, to a pest, a locus of pest, preferably a plant, or to a plant susceptible to attack by a pest. The compounds of formula (I) are preferably used against insects or acarines. The compounds of the invention may also be used for controlling insects that are resistant to known insecticides.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and for example a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately diesters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity. The biologically active compounds of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. The weight ratio of the biologically active compound of formula I to an additional active ingredient may for example be between 1000:1 and 1:1000. Examples of suitable pesticides include the following:

a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, lufeneron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen;

s) Diamides, such as flubendiamide, chlorantraniliprole (Rynaxypyr®) or cyantraniliprole;

t) Sulfoxaflor; or u) Metaflumizone;

v) Fipronil and Ethiprole;

w) Pyrifluquinazon;

x) buprofezin; or y) 4-[(6-Chloro-pyridin-3-ylmethyl)-(2,2-difluoro-ethyl)-amino]-5H-furan-2-one (DE 102006015467).

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704) (e.g. acibenzolar-5-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)—N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-Al, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, 1,3-Difluoroimethyl-1H-pyrazole-4-carboxylic acid (4'-methylsulfanyl-biphenyl-2-yl)-amide, 1,3-Difluoroimethyl-1H-pyrazole-4-carboxylic acid (2-dichloromethylene-3-ethyl-1-methyl-indan-4-yl)-amide, and 1,3-Difluoromethyl-4H-pyrazole-4-carboxylic acid [2-(2,4-dichlorophenyl)-2-methoxy-1-methyl-ethyl]-amide.

The biologically active compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

EXAMPLES

The following Examples illustrate, but do not limit, the invention.

The following abbreviations were used in this section: DCE=1,2-dichloroethane, s=singlet; bs=broad singlet; d=doublet; dd=double doublet; dt=double triplet; t=triplet, tt=triple triplet, q=quartet, sept=septet; m=multiplet;

Me=methyl; Et=ethyl; Pr=propyl; Bu=butyl; M.p.=melting point; RT=retention time, [M+H]⁺=molecular mass of the molecular cation, [M−H]⁻=molecular mass of the molecular anion, ee=enantiomeric excess.

The following LC-MS methods were used to characterize the compounds:

Method F

| | | | | |
|---|---|---|---|---|
| MS | ZQ Mass Spectrometer from Waters (single quadrupole mass spectrometer), ionization method: electrospray, polarity: negative ionization, capillary (kV) 3.00, cone (V) 45.00, source temperature (° C.) 100, desolvation temperature (° C.) 250, cone gas flow (L/Hr) 50, desolvation gas flow (L/Hr) 400, mass range: 150 to 1000 Da. | | | |
| LC | HP 1100 HPLC from Agilent: solvent degasser, binary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). | | | |

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |
| 3.1 | 95 | 5 | 1.7 |

Example P1

Preparation of 4-[(R)-3-(3,5-Dichloro-phenyl)-4,4,4-trifluoro-3-nitromethyl-butyryl]-2-methyl-benzoic acid tert-butyl ester

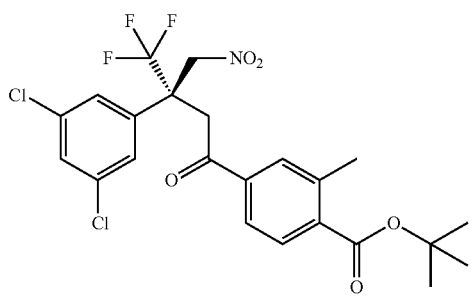 [SMILES: Cc1cc(C(=O)C[C@](C[N+](=O)[O-])(c2cc(Cl)cc(Cl)c2)C(F)(F)F)ccc1C(=O)OC(C)(C)C]

4-[(E)-3-(3,5-Dichloro-phenyl)-4,4,4-trifluoro-but-2-enoyl]-2-methyl-benzoic acid tert-butyl ester (0.0928 g, 0.198 mmol) and 1-[3,5-bis(trifluoromethyl)phenyl]-3-{(S)[(2S,4S,5R)-5-ethyl-1-aza-bicyclo[2.2.2]oct-2-yl]-(6-methoxy-4-quinolinyl)methyl}thiourea (0.0121 g, 0.020 mmol) were dissolved in nitromethane (0.6 ml) and the resulting solution was stirred at 50° C. for 2.5 days. The reaction mixture was cooled to room temperature and aqueous saturated ammonium chloride was added. The resulting mixture was extracted with dichloromethane (3×) and the combined organic fractions were dried over sodium sulfate. The crude product was purified by flash chromatography (0% to 5% ethyl acetate in cyclohexane) to afford 4-[(R)-3-(3,5-dichloro-phenyl)-4,4,4-trifluoro-3-nitromethyl-butyryl]-2-methyl-benzoic acid tert-butyl ester (0.080 g, 77%) as a beige solid. Chiral HPLC analysis (Chiralpack AS-RH, MeCN: MeOH:H₂O=75:5:20, 1 ml/min, retention time 3.26 minutes (major enantiomer), 2.86 minutes (minor enantiomer) indicated that the reaction proceeded with 97.4% enantioselectivity.

¹H NMR (400 MHz, CDCl₃) δ 7.91 (d, 1H), 7.82-7.78 (m, 2H), 7.42 (t, 1H), 7.20 (s, 2H), 5.61 (d, 1H), 5.47 (d, 1H), 4.16 (d, 1H), 3.99 (d, 1H), 2.64 (s, 3H), 1.63 (s, 9H)

The absolute configuration of the major enantiomer was unambiguously assigned as being (R) by X ray diffraction on crystals of the compound (recrystallization from EtOH).

Alternatively, to a solution of 3-[3,5-bis(trifluoromethyl)anilino]-4-[[(S)-(6-methoxy-4-quinolyl)-[(1S,2S,5S)-5-vinylquinuclidin-2-yl]methyl]amino]cyclobut-3-ene-1,2-dione (13 mg, prepared according to the literature: Org. Lett., 2010, 12 (23), 5450-5453) and nitromethane (0.6 ml) under argon, was added 4-[(E)-3-(3,5-Dichloro-phenyl)-4,4,4-trifluoro-but-2-enoyl]-2-methyl-benzoic acid tert-butyl ester (100 mg). The solution was heated for 5 days at 50° C. then more catalyst (15 mg) was added. The reaction was heated again for 3 days at 50° C. then allowed to stand at room temperature for 15 days. Water was then added and the resulting mixture was extracted with dichloromethane and the combined organic fractions were dried over sodium sulfate. The crude product was purified by flash chromatography (0% to 5% ethyl acetate in cyclohexane) to afford 4-[(R)-3-(3,5-Dichloro-phenyl)-4,4,4-trifluoro-3-nitromethyl-butyryl]-2-methyl-benzoic acid tert-butyl ester (26 mg). Chiral HPLC analysis (Chiralpack IA, Heptane:2-propanol=90:10, 1 ml/min, retention time 6.13 minutes (major enantiomer), 7.29 minutes (minor enantiomer) indicated that the reaction proceeded with 61% enantioselectivity in favor of the R enantiomer.

Alternatively, to a solution of 1-[3,5-bis(trifluoromethyl)phenyl]-3-[(S)-(6-methoxy-4-quinolyl)-[(2S)-quinuclidin-2-yl]methyl]urea; prop-1-ene (09 mg, prepared according to the literature: Organic Letters 2007, 9, (14), 2621-2624) and nitromethane (0.6 ml) under argon, was added 4-[(E)-3-(3,5-Dichloro-phenyl)-4,4,4-trifluoro-but-2-enoyl]-2-methyl-benzoic acid tert-butyl ester (100 mg). The solution was heated for 3 days at 50° C. then allowed to stand at room temperature for 2 days. Water was then added and the resulting mixture was extracted with diethyl ether and the combined organic fractions were dried over sodium sulfate. The crude product was purified by flash chromatography (0% to 5% ethyl acetate in cyclohexane) to afford 4-[(R)-3-(3,5-Dichloro-phenyl)-4,4,4-trifluoro-3-nitromethyl-butyryl]-2-methyl-benzoic acid tert-butyl ester (100 mg). Chiral HPLC analysis (Chiralpack IA, Heptane:2-propanol=90:10, 1 ml/min, retention time 6.43 minutes (major enantiomer), 7.78 minutes (minor enantiomer) indicated that the reaction proceeded with 95% enantioselectivity in favor of the R enantiomer.

Alternatively, to a solution of 1-cyclohexyl-3-[(S)-(6-methoxy-4-quinolyl)-[(1S,2S,5S)-5-vinylquinuclidin-2-yl]methyl]thiourea (10 mg, prepared according to the literature: Journal of Organic Chemistry 2008, 3475) and nitromethane (0.6 ml) under argon, was added 4-[(E)-3-(3,5-Dichloro-phenyl)-4,4,4-trifluoro-but-2-enoyl]-2-methyl-benzoic acid tert-butyl ester (100 mg). The solution was heated for 8 days at 50° C. then allowed to stand at room temperature for 14 days. Water was then added and the resulting mixture was extracted with diethyl ether and the combined organic fractions were dried over sodium sulfate. The crude product was purified by flash chromatography (0% to 5% ethyl acetate in cyclohexane) to afford 4-[(R)-3-(3,5-Dichloro-phenyl)-4,4,4-trifluoro-3-nitromethyl-butyryl]-2-methyl-benzoic acid tert-butyl ester (28 mg). Chiral HPLC analysis (Chiralpack IA, Heptane:2-propanol=90:10, 1 ml/min, retention time 6.06 minutes (major enantiomer), 7.19 minutes (minor enantiomer) indicated that the reaction proceeded with 89% enantioselectivity in favor of the R enantiomer.

Alternatively, 4-[(E)-3-(3,5-Dichloro-phenyl)-4,4,4-trifluoro-but-2-enoyl]-2-methyl-benzoic acid tert-butyl ester (0.075 g, 0.163 mmol) and antracen-9-yl-methyl quininium bromide (0.020 g, 0.034 mmol) were dissolved in toluene (2.0 ml). Nitromethane (10 molar equivalents) and potassium carbonate (0.025 g, 0.181 mmol) were added and the resulting suspension was stirred at 50° C. for 24 h. The reaction mixture was cooled to room temperature and water was added. The resulting mixture was extracted with dichloromethane (3×) and the combined organic fractions were dried over sodium sulfate. The crude product was purified by flash chromatography (0% to 5% ethyl acetate in cyclohexane) to afford 4-[(R)-3-(3,5-dichloro-phenyl)-4,4,4-trifluoro-3-nitromethyl-butyryl]-2-methyl-benzoic acid tert-butyl ester (0.051 g, 60%) as a white foam. Chiral HPLC analysis (Chiralpack AS-RH, Heptane/2-propanol=90:10, 1 ml/min, retention time 6.13 minutes (major enantiomer), 7.35 minutes (minor enantiomer)) indicated that the reaction proceeded with 62% enantioselectivity.

Alternatively the reaction could be conducted under otherwise identical conditions, but using nitromethane as a solvent instead of toluene. 4-[(R)-3-(3,5-Dichloro-phenyl)-4,4,4-trifluoro-3-nitromethyl-butyryl]-2-methyl-benzoic acid tert-butyl ester was obtained in 71% yield and chiral HPLC analysis (Method as described above) indicated that the reaction proceeded with 25% enantioselectivity.

Alternatively the reaction could be conducted under otherwise identical conditions, but using 2,3,4,5,6-pentafluorophenyl-methyl quininium bromide (0.2 molar equivalents) as a catalyst (toluene as a solvent). 4-[(R)-3-(3,5-Dichloro-phenyl)-4,4,4-trifluoro-3-nitromethyl-butyryl]-2-methyl-benzoic acid tert-butyl ester was obtained in 49% yield and chiral HPLC analysis (Chiralpak IA, Heptane/2-propanol=95:5, 1 ml/min, retention time 8.56 minutes (major enantiomer), 11.35 minutes (minor enantiomer)) indicated that the reaction proceeded with 54% enantioselectivity.

The following catalysts for the asymmetric addition of nitromethane to 4-[(E)-3-(3,5-dichloro-phenyl)-4,4,4-trifluoro-but-2-enoyl]-2-methyl-benzoic acid tert-butyl ester were tried but gave no appreciable reactivity:
1-((1S,2S)-2-Amino-cyclohexyl)-3-phenyl-thiourea and 1-((1S,2S)-2-amino-cyclohexyl)-3-(3,5-bis-trifluoromethyl-phenyl)-thiourea (as described in Mei, K.; Jin, M.; Zhang, S.; Li, P.;
Liu, W.; Chen, X.; Xue, F.; Duan, W.; Wang, W. Org. Lett. 2009, 11, 2864)

L-proline with 2,5-dimethylpiperazine as a base (as described in Hanessian, S.; Pham, V. Org. Lett. 2000, 2, 2975)
(S)-5-Pyrrolidin-2-yl-1H-tetrazole (as described in Mitchell, C. E. T.; Brenner, S. E.; Ley, S. V Chem. Commun. 2005, 5346
Jacobsen's (S,S)-(salen)Al catalyst (as described in Taylor, S. M; Zalatan, D. N.; Lercher, A. M.; Jacobsen, E. N. J. Am. Chem. Soc. 2005, 127, 1313)

Example P1A (Comparative Example)

Preparation of 4-[(S)-3-(3,5-Dichloro-phenyl)-4,4,4-trifluoro-3-nitromethyl-butyryl]-2-methyl-benzoic acid tert-butyl ester

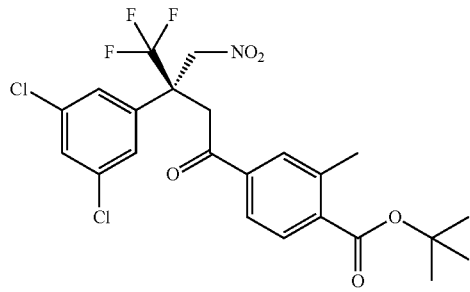 [SMILES: Cc1cc(C(=O)C[C@@](C[N+](=O)[O-])(c2cc(Cl)cc(Cl)c2)C(F)(F)F)ccc1C(=O)OC(C)(C)C]

To a solution of 3-(3,5-Bis-trifluoromethyl-phenylamino)-4-{[(S)-(6-methoxy-quinolin-4-yl)-((R)-5-vinyl-1-aza-bicyclo[2.2.2]oct-2-yl)-methyl]-amino}-cyclobut-3-ene-1,2-dione (20 mg, prepared according to the literature: Org. Lett., 2010, 12 (23), 5450-5453) in 1,2-dichloroethane (1.5 mL) under argon, was added 4-[(E)-3-(3,5-Dichloro-phenyl)-4,4,4-trifluoro-but-2-enoyl]-2-methyl-benzoic acid tert-butyl ester (300 mg) and nitromethane (0.35 ml). The solution was refluxed for 24 hours then more 3-(3,5-Bis-trifluoromethyl-phenylamino)-4-{[(S)-(6-methoxy-quinolin-4-yl)-((R)-5-vinyl-1-aza-bicyclo[2.2.2]oct-2-yl)-methyl]-amino}-cyclobut-3-ene-1,2-dione (20 mg) was added. The solution was refluxed for 48 hours then more nitromethane (0.35 mL) and 3-(3,5-Bis-trifluoromethyl-phenylamino)-4-{[(S)-(6-methoxy-quinolin-4-yl)-((R)-5-vinyl-1-aza-bicyclo[2.2.2]oct-2-yl)-methyl]-amino}-cyclobut-3-ene-1,2-dione (25 mg) were added. The solution was refluxed for another 16 hours and then the heating was stopped. The reaction mixture was cooled to room temperature and water was added. The resulting mixture was extracted with dichloromethane and the combined organic fractions were dried over sodium sulfate. The crude product was purified by flash chromatography (0% to 5% ethyl acetate in cyclohexane) to afford 4-[(S)-3-(3,5-Dichloro-phenyl)-4,4,4-trifluoro-3-nitromethyl-butyryl]-2-methyl-benzoic acid tert-butyl ester (127 mg). Chiral HPLC analysis (Chiralpack IA, Heptane:2-propanol:diethylamine=90:10:0.1, 1 ml/min, retention time 7.52 minutes (major enantiomer), 6.30 minutes (minor enantiomer) indicated that the reaction proceeded with 93% enantioselectivity in favor of the S enantiomer.

Example P2

Preparation of 4-[(R)-4-(3,5-Dichloro-phenyl)-4-trifluoromethyl-4,5-dihydro-3H-pyrrol-2-yl]-2-methyl-benzoic acid tert-butyl ester

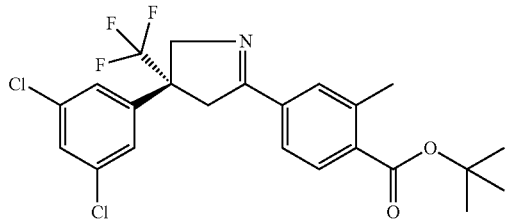 [SMILES: Cc1cc(C2=NC[C@@](c3cc(Cl)cc(Cl)c3)(C(F)(F)F)C2)ccc1C(=O)OC(C)(C)C]

To a vigorously stirred suspension of zinc (0.060 g, 0.913 mmol) in dimethylformamide (2.0 ml) was added a solution of 4-[(R)-3-(3,5-dichloro-phenyl)-4,4,4-trifluoro-3-nitromethyl-butyryl]-2-methyl-benzoic acid tert-butyl ester (0.190 g, 0.365 mmol) in dimethylformamide (2.0 ml). The resulting mixture was warmed to 80° C. and 37% aqueous hydrochloric acid (3.0 ml) was added very slowly to minimize the foaming. After stirring for 2 hours the reaction was cooled to room temperature and quenched by adding a pH 7 buffer solution. The mixture was extracted with dichloromethane; the organic layer was washed with water (3×) and brine. The crude product was purified by flash chromatography (6% ethyl acetate in cyclohexane) to afford 4-[(R)-4-(3,5-dichloro-phenyl)-4-trifluoromethyl-4,5-dihydro-3H-pyrrol-2-yl]-2-methyl-benzoic acid tert-butyl ester as a pale yellow oil (0.050 g, 29%).

$^1$H NMR (400 MHz, CDCl$_3$) δ 7.87 (d, 1H), 7.71 (s, 1H), 7.67 (d, 1H), 7.38 (t, 1H), 7.27 (s, 2H), 4.90 (dd, 1H), 4.45 (d, 1H), 3.81 (dd, 1H), 3.46 (d, 1H), 2.62 (s, 3H), 1.61 (s, 9H)

Alternatively, the title compound can be obtained by carrying out the following experiment: To a vigorously stirred solution of 4-[(R)-3-(3,5-dichloro-phenyl)-4,4,4-trifluoro-3-nitromethyl-butyryl]-2-methyl-benzoic acid tert-butyl ester (100 mg) in ethanol (6 mL) was added Raney Nickel (1.44 g, 50% suspension in water, previously washed with dry ethanol) and the reaction was stirred at room temperature under hydrogen (1 atm) for one hour. Then the solution was filtered over celite, and the resulting filtrate was concentrated in vacuo to give the title compound (78 mg) as a pale yellow solid. Chiral HPLC analysis (Chiralpack IA, Heptane:2-propanol:diethylamine=90:10:0.1, 1 ml/min, retention time 5.77 minutes (91.43%), 8.71 minutes (3.79%).

Alternatively, the title compound can be obtained by carrying out the following experiment: To a vigorously stirred solution of 4-[(R)-3-Cyano-3-(3,5-dichloro-phenyl)-4,4,4-trifluoro-butyryl]-2-methyl-benzoic acid tert-butyl ester (150 mg) in ethanol (9 mL) was added Raney Nickel (1.44 g, 50% suspension in water, previously washed with dry ethanol) and the reaction was stirred at room temperature under hydrogen (1 atm) for 2 hours then under arong overnight. Then the solution was filtered over celite, and the resulting filtrate was concentrated in vacuo to give the title compound (138 mg) as a pale yellow oil. The crude product was purified by flash chromatography (15% dichloromethane in ethyl acetate) to afford 4-[(R)-4-(3,5-dichloro-phenyl)-4-trifluoromethyl-4,5-dihydro-3H-pyrrol-2-yl]-2-methyl-benzoic acid tert-butyl ester as a pale yellow oil (0.070 g). Chiral HPLC analysis (Chiralpack IA, Heptane:2-propanol:diethylamine=90:10:0.1, 1 ml/min, retention time 5.93 minutes (major enantiomer), 8.57 minutes (minor enantiomer).

Example P3

Preparation of 4-[(R)-4-(3,5-Dichloro-phenyl)-1-oxy-4-trifluoromethyl-4,5-dihydro-3H-pyrrol-2-yl]-2-methyl-benzoic acid tert-butyl ester

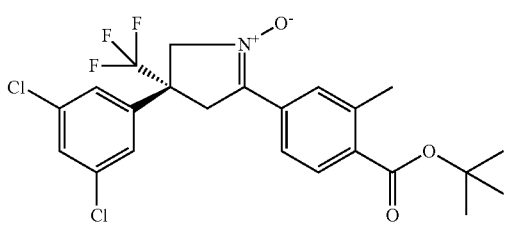 [SMILES: Cc1cc(C2=[N+]([O-])C[C@@](c3cc(Cl)cc(Cl)c3)(C(F)(F)F)C2)ccc1C(=O)OC(C)(C)C]

Sodium borohydride (0.023 g, 0.615 mmol) was added to a solution of 4-[(R)-3-(3,5-dichloro-phenyl)-4,4,4-trifluoro-3-nitromethyl-butyryl]-2-methyl-benzoic acid tert-butyl ester (0.040 g, 0.077 mmol) and nickel (II) chloride (0.010 g, 0.077 mmol) in a mixture of tetrahydrofuran (4 ml) and methanol (8 ml) at 0 C. After stirring at this temperature for 4 hours the reaction was quenched by adding a small amount of water. The solvents were evaporated under reduced pressure and the residue was taken up in ethyl acetate and water. The organic phase was washed with water and brine and evaporated under reduced pressure. The crude product was purified by flash chromatography (6% ethyl acetate in cyclohexane) to afford 4-[(R)-4-(3,5-Dichloro-phenyl)-1-oxy-4-trifluoromethyl-4,5-dihydro-3H-pyrrol-2-yl]-2-methyl-benzoic acid tert-butyl ester as a white solid (0.038 g, quant.).

1H NMR (400 MHz, CDCl$_3$) δ 8.71 (d, 1H), 8.16 (s, 1H), 7.90 (d, 1H), 7.45 (s, 1H), 7.26 (s, 2H), 4.78 (ap q, 2H), 3.93 (d, 2H), 3.68 (d, 2H), 2.63 (s, 3H), 1.61 (s, 9H)

Example P4

Preparation of 4-[(R)-4-(3,5-Dichloro-phenyl)-4-trifluoromethyl-4,5-dihydro-3H-pyrrol-2-yl]-2-methyl-benzoic acid tert-butyl ester

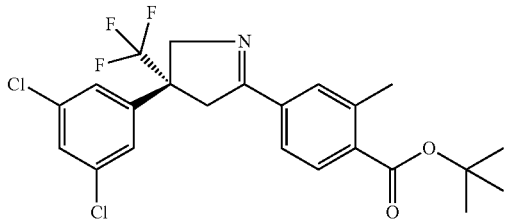 [SMILES: Cc1cc(C2=NC[C@@](c3cc(Cl)cc(Cl)c3)(C(F)(F)F)C2)ccc1C(=O)OC(C)(C)C]

Sodium acetate (0.058 g, 0.707 mmol) was added to a solution of 4-[(R)-4-(3,5-dichloro-phenyl)-1-oxy-4-trifluoromethyl-4,5-dihydro-3H-pyrrol-2-yl]-2-methyl-benzoic acid tert-butyl ester (0.036 g, 0.074 mmol) in a mixture of tetrahydrofuran (2 ml) and water (1 ml). To the resulting suspension was added titanium (III) chloride (15% in 10% HCl, 0.38 ml, 0.441 mmol). After vigorous stirring for 18 hours the bright violet reaction mixture was diluted with dichloromethane and filtered through celite. The filtrate was washed with aqueous sodium bicarbonate and the aqueous layer was extracted with dichloromethane. The crude residue was purified by flash chromatography (0% to 15% ethyl acetate in cyclohexane) to afford 4-[(R)-4-(3,5-dichloro-phenyl)-4-trifluoromethyl-4,5-dihydro-3H-pyrrol-2-yl]-2-methyl-benzoic acid tert-butyl ester (0.0056 g, 16%) as a colorless oil as well as the recovered 4-[(R)-4-(3,5-dichloro-phenyl)-1-oxy-4-trifluoromethyl-4,5-dihydro-3H-pyrrol-2-yl]-2-methyl-benzoic acid tert-butyl ester (0.0177 g).

Example P5

Preparation of 4-[(R)-4-(3,5-Dichloro-phenyl)-4-trifluoromethyl-4,5-dihydro-3H-pyrrol-2-yl]-2-methyl-benzoic acid-

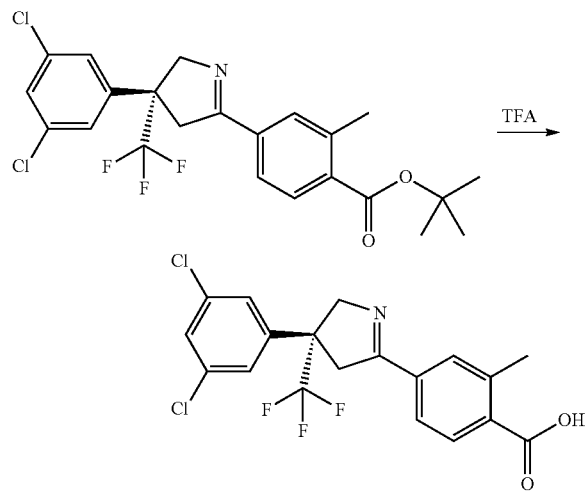

To a solution of 4-[(R)-4-(3,5-Dichloro-phenyl)-4-trifluoromethyl-4,5-dihydro-3H-pyrrol-2-yl]-2-methyl-benzoic acid tert-butyl ester (0.68 g) in dichloromethane (0.7 ml) was added trifluoromethyl acetic acid ("TFA") (0.07 ml). The reaction mixture was stirred at ambient temperature for 4.5 hours. The dichloromethane was evaporated under reduced pressure and the residue was taken up in ethyl acetate and water. The organic phase was washed with water and brine and evaporated under reduced pressure to afford 4-[(R)-4-(3,5-Dichloro-phenyl)-4-trifluoromethyl-4,5-dihydro-3H-pyrrol-2-yl]-2-methyl-benzoic acid which was used as such in the next reaction). LCMS (Method F) RT=2.07 min, [M−H]⁻=414/416.

Example P6

Preparation of 4-[(R)-3-Cyano-3-(3,5-dichloro-phenyl)-4,4,4-trifluoro-butyryl]-2-methyl-benzoic acid tert-butyl ester

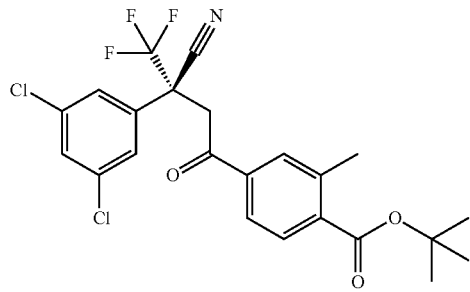 [SMILES: Cc1cc(C(=O)C[C@](C#N)(c2cc(Cl)cc(Cl)c2)C(F)(F)F)ccc1C(=O)OC(C)(C)C]

Potassium cyanide (0.0090 g, 0.138 mmol) and acetone cyanohydrin (0.040 ml, 0.435 mmol) were added to a solution of 4-[(E)-3-(3,5-Dichloro-phenyl)-4,4,4-trifluoro-but-2-enoyl]-2-methyl-benzoic acid tert-butyl ester (0.0645 g, 0.140 mmol) in toluene (1.0 ml). To this vigorously stirred suspension was added 2,3,4,5,6-pentafluorophenyl-methyl quininium chloride (0.015 g, 0.028 mmol). The reaction mixture was stirred at 45° C. for 18 hours. At this time water was added and the reaction mixture was extracted with dichloromethane (3×). The crude product was purified by flash chromatography (0% to 5% ethyl acetate in cyclohexane) to afford 4-[(R)-3-Cyano-3-(3,5-dichloro-phenyl)-4,4,4-trifluoro-butyryl]-2-methyl-benzoic acid tert-butyl ester (0.048 g, 66%) as a white foam. Chiral HPLC analysis (Chiralpack IA, Heptane:2-propanol:diethylamine=95:5:0.1, 1 ml/min, retention time 6.52 minutes (major enantiomer), 6.02 minutes (minor enantiomer) indicated that the reaction proceeded with 88% enantioselectivity. $^1$H NMR (400 MHz, CDCl$_3$) δ 7.89 (d, 1H), 7.78-7.72 (m, 2H), 7.48 (s, 2H), 7.46-7.42 (m, 1H), 4.17 (d, 1H), 4.02 (d, 2H), 2.62 (s, 3H), 1.62 (s, 9H)

Alternatively the reaction could be conducted under otherwise identical conditions, but using 2,3,4,5,6-pentafluorophenyl-methyl quininium bromide (0.2 molar equivalents) as a catalyst. 4-[(R)-3-Cyano-3-(3,5-dichloro-phenyl)-4,4,4-trifluoro-butyryl]-2-methyl-benzoic acid tert-butyl ester was obtained in 79% yield and chiral HPLC analysis (method as described above) indicated that the reaction proceeded with 95% enantioselectivity.

Alternatively the reaction could be conducted under otherwise identical conditions, but using 3,4,5-trimethoxyphenyl-methyl quininium chloride (0.2 molar equivalents) as a catalyst. 4-[(R)-3-Cyano-3-(3,5-dichloro-phenyl)-4,4,4-trifluoro-butyryl]-2-methyl-benzoic acid tert-butyl ester was obtained in 42% yield and chiral HPLC analysis (method as described above) indicated that the reaction proceeded with 91% enantioselectivity.

Conducting the reaction under otherwise identical conditions but increasing the temperature from 60° C. to 110° C. increased the yield of 4-[(R)-3-Cyano-3-(3,5-dichloro-phenyl)-4,4,4-trifluoro-butyryl]-2-methyl-benzoic acid tert-butyl ester to 70%. Chiral HPLC analysis (method as described above) indicated that the reaction proceeded with 75% enantioselectivity.

Alternatively the reaction could be conducted under otherwise identical conditions, but using only potassium cyanide as a cyanide source. 4-[(R)-3-Cyano-3-(3,5-dichloro-phenyl)-4,4,4-trifluoro-butyryl]-2-methyl-benzoic acid tert-butyl ester was obtained in 28% yield and chiral HPLC analysis (method as described above) indicated that the reaction proceeded with 96% enantioselectivity.

Potassium cyanide (0.0377 g, 0.578 mmol), cesium chloride (0.0086 g, 0.051 mmol) and acetone cyanohydrin (0.142 ml, 1.55 mmol) were added to a solution of 4-[(E)-3-(3,5-dichloro-phenyl)-4,4,4-trifluoro-but-2-enoyl]-2-methyl-benzoic acid tert-butyl ester (0.250 g, 0.512 mmol) in toluene (5.0 ml). To this vigorously stirred suspension was added antracen-9-yl-methyl quininium chloride (0.071 g, 0.129 mmol). The reaction mixture was stirred at 90° C. for 18 hours. At this time water was added and the reaction mixture was extracted with dichloromethane (3×). The crude product was purified by flash chromatography (0% to 5% ethyl acetate in cyclohexane) to afford 4-[(R)-3-Cyano-3-(3,5-dichloro-phenyl)-4,4,4-trifluoro-butyryl]-2-methyl-benzoic acid tert-butyl ester (0.197 g, 79%) as a white foam. Chiral HPLC analysis (Chiralpack IB, Heptane:2-propanol=90:10, 1 ml/min, retention time 8.18 minutes (major enantiomer, minor enantiomer not observed), indicated that the reaction proceeded with >99% enantioselectivity.

Alternatively the reaction could be conducted under otherwise identical conditions, but using potassium carbonate (1.1 molar equivalents) in place of potassium cyanide and cesium chloride. 4-[(R)-3-Cyano-3-(3,5-dichloro-phenyl)-4,4,4-trifluoro-butyryl]-2-methyl-benzoic acid tert-butyl ester was obtained in 68% yield and chiral HPLC analysis (method as described above) indicated that the reaction proceeded with 84% enantioselectivity.

Conducting the reaction in a biphasic system (water/1,2-dichloroethane 1:1) using 2,3,4,5,6-pentafluorophenyl-methyl quininium bromide (0.2 molar equivalents) as a catalyst and potassium cyanide (5 molar equivalents) as a source of cyano group lead only to the recovery of starting material as well as formation of a small amount of an unidentified byproduct.

Example P7

Preparation of 5-[(3R)-3-(3,5-dichlorophenyl)-4,4,4-trifluoro-3-(nitromethyl)butanoyl]-2-(1,2,4-triazol-1-yl)benzonitrile

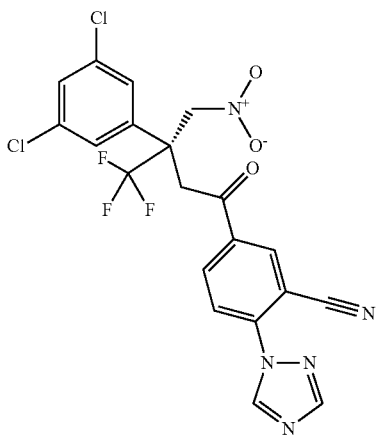 [SMILES: N#Cc1cc(C(=O)C[C@](C[NH+]([O-])O)(c2cc(Cl)cc(Cl)c2)C(F)(F)F)ccc1-n1cncn1]

A solution of anthracenylmethyl quininium chloride (19 mg), nitromethane (0.025 ml) and 5-[(E)-3-(3,5-dichlorophenyl)-4,4,4-trifluoro-but-2-enoyl]-2-(1,2,4-triazol-1-yl)benzonitrile (100 mg) in toluene (2 mL) under argon, was heated for 2 hours at 50° C. then potassium carbonate (64 mg) was added. The reaction was heated for 24 hours at 50° C. then more nitromethane (0.02 mL) was added. The reaction was heated again at 50° C. for 3 hours then was allowed to stand at room temperature for 18 hours. Water was then added and the resulting mixture was extracted with dichloromethane and the combined organic fractions were dried over sodium sulfate. The crude product was purified by flash chromatography (0% to 50% ethyl acetate in cyclohexane) to afford 5-[(3R)-3-(3,5-dichlorophenyl)-4,4,4-trifluoro-3-(nitromethyl)butanoyl]-2-(1,2,4-triazol-1-yl)benzonitrile (69 mg). Chiral HPLC analysis (CHIRALPAK AS-RH, acetonitrile:Methanol:water=40:5:55, 1 ml/min, retention time 11.88 minutes (minor enantiomer), 13.88 minutes (major enantiomer) indicated that the reaction proceeded with 50% enantioselectivity in favor of the R enantiomer.

Example P8

Preparation of 2-[[2-bromo-4-[(3R)-3-(3,5-dichlorophenyl)-4,4,4-trifluoro-3-(nitromethyl)butanoyl]phenyl]methyl]isoindoline-1,3-dione

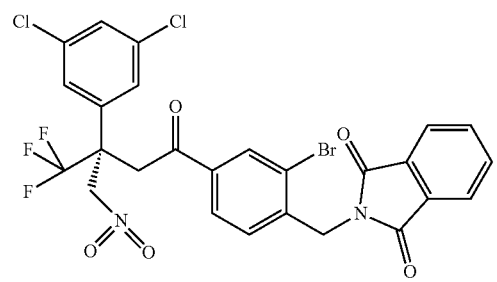 [SMILES: O=C(C[C@](C[N+](=O)[O-])(c1cc(Cl)cc(Cl)c1)C(F)(F)F)c1ccc(CN2C(=O)c3ccccc3C2=O)c(Br)c1]

A solution of anthracenylmethyl quininium bromide (200 mg), nitromethane (0.04 ml), potassium carbonate (94 mg) and 2-[[2-bromo-4-[(E)-3-(3,5-dichlorophenyl)-4,4,4-trifluoro-but-2-enoyl]phenyl]methyl]isoindoline-1,3-dione (200 mg) in toluene (2 mL) under argon, was heated for 2 hours at 50° C. then potassium carbonate (64 mg) was added. The reaction was heated for 24 hours at 50° C. then more nitromethane (0.02 mL) was added. The reaction was heated again at 50° C. for 1.5 hours then was allowed to stand at room temperature for 18 hours. Water was then added and the resulting mixture was extracted with dichloromethane and the combined organic fractions were dried over sodium sulfate. The crude product was purified by flash chromatography (0% to 25% ethyl acetate in cyclohexane) to afford 2-[[2-bromo-4-[(3R)-3-(3,5-dichlorophenyl)-4,4,4-trifluoro-3-nitromethyl)butanoyl]phenyl]methyl]isoindoline-1,3-dione (174 mg). Chiral HPLC analysis (Chiralpack IB, Heptane/isopropanol 70/30, flow: 1 mL, retention time 12.10 minutes (major enantiomer), 14.34 minutes (minor enantiomer) indicated that the reaction proceeded with 49% enantioselectivity in favor of the R enantiomer.

Example P9

Preparation of 4-[(R)-3-(3,5-Dichloro-phenyl)-4,4,4-trifluoro-3-nitromethyl-butyryl]-2-methyl-N-(3-methyl-thietan-3-yl)-benzamide

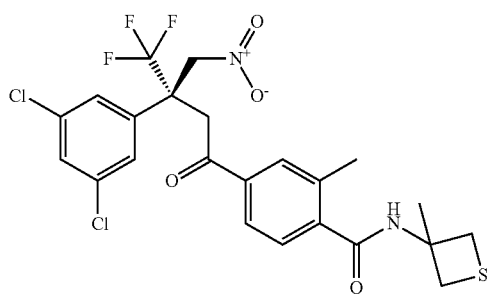 [SMILES: Cc1cc(C(=O)C[C@](C[N+](=O)[O-])(c2cc(Cl)cc(Cl)c2)C(F)(F)F)ccc1C(=O)NC1(C)CSC1]

4-[(E)-3-(3,5-Dichloro-phenyl)-4,4,4-trifluoro-but-2-enoyl]-2-methyl-N-(3-methyl-thietan-3-yl)-benzamide (0.100 g, 0.205 mmol) and 1-[3,5-bis(trifluoromethyl)phenyl]-3-{(S)[(2S,4S,5R)-5-ethyl-1-aza-bicyclo[2.2.2]oct-2-yl]-(6-methoxy-4-quinolinyl)methyl}thiourea (0.0305 g, 0.020 mmol) were dissolved in nitromethane (2.0 ml) and the resulting solution was stirred at 60° C. for 3 days. The reaction mixture was cooled to room temperature and aqueous saturated ammonium chloride was added. The resulting mixture was extracted with dichloromethane (3×) and the combined organic fractions were dried over sodium sulfate. The crude product was purified by flash chromatography (0% to 25% ethyl acetate in cyclohexane) to afford 4-[(R)-3-(3,5-Dichloro-phenyl)-4,4,4-trifluoro-3-nitromethyl-butyryl]-2-methyl-N-(3-methyl-thietan-3-yl)-benzamide (0.021 g, 19%) as a light yellow solid. Chiral HPLC analysis (Chiralpack IA, Heptane:2-propanol=70:30, 1 ml/min, retention time 5.71 minutes (major enantiomer), 8.13 minutes (minor enantiomer)) indicated that the reaction proceeded with 79% enantioselectivity. $^1$H NMR (400 MHz, CDCl$_3$) δ 7.82-7.78 (m, 2H), 7.47 (d, 1H), 7.43-7.41 (m, 1H), 7.19 (s, 2H), 5.90 (s, 1H), 5.60 (d, 1H), 5.45 (d, 1H), 4.13 (d, 1H), 3.97 (d, 1H), 3.88 (d, 2H), 3.09 (d, 2H), 2.53 (s, 3H), 1.87 (s, 3H).

Example P10

4-[(R)-3-Cyano-3-(3,5-dichloro-phenyl)-4,4,4-trifluoro-butyryl]-2-methyl-N-(3-methyl-thietan-3-yl)-benzamide

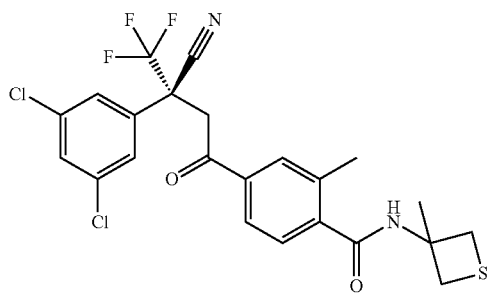 [SMILES: Cc1cc(C(=O)C[C@](C#N)(c2cc(Cl)cc(Cl)c2)C(F)(F)F)ccc1C(=O)NC1(C)CSC1]

Potassium cyanide (0.0090 g, 0.139 mmol) and acetone cyanohydrin (0.034 ml, 0.372 mmol) were added to a solution of 4-[(E)-3-(3,5-Dichloro-phenyl)-4,4,4-trifluoro-but-2-enoyl]-2-methyl-N-(3-methyl-thietan-3-yl)-benzamide (0.0600 g, 0.123 mmol) in toluene (3.0 ml). To this vigorously stirred suspension was added 2,3,4,5,6-pentafluorophenyl-methyl quininium chloride (0.0180 g, 0.031 mmol). The reaction mixture was stirred at 90° C. for 6 days. After this time water was added and the reaction mixture was extracted with dichloromethane (3×). The crude product was purified by flash chromatography (0% to 25% ethyl acetate in cyclohexane) to afford 4-[(R)-3-Cyano-3-(3,5-dichloro-phenyl)-4,4,4-trifluoro-butyryl]-2-methyl-N-(3-methyl-thietan-3-yl)-benzamide (0.015 g, 24%) as a light yellow solid. Chiral HPLC analysis (Chiralpack IB, Heptane:2-propanol=70:30, 1 ml/min, retention time 5.91 minutes (major enantiomer), 5.31 minutes (minor enantiomer) indicated that the reaction proceeded with 69% enantioselectivity.
$^1$H NMR (400 MHz, CDCl$_3$) δ 7.71-7.36 (m, 5H), 7.33 (d, 1H), 6.33 (s, 1H), 4.22 (d, 1H), 3.99 (d, 1H), 3.84 (dd, 2H), 3.06 (d, 2H), 2.40 (s, 3H), 1.85 (s, 3H)

Alternatively the reaction could be conducted under otherwise identical conditions, but using antracen-9-yl-methyl quininium chloride (0.25 molar equivalents) as a catalyst. 4-[(R)-3-Cyano-3-(3,5-dichloro-phenyl)-4,4,4-trifluoro-butyryl]-2-methyl-N-(3-methyl-thietan-3-yl)-benzamide was obtained in 38% yield and chiral HPLC analysis (method as described above) indicated that the reaction proceeded with 64% enantioselectivity.

Alternatively the reaction could be conducted under otherwise identical conditions, but using antracen-9-yl-methyl quininium chloride (0.25 molar equivalents) as a catalyst and potassium carbonate in place of potassium cyanide. 4-[(R)-3-Cyano-3-(3,5-dichloro-phenyl)-4,4,4-trifluoro-butyryl]-2-methyl-N-(3-methyl-thietan-3-yl)-benzamide was obtained in 62% yield and chiral HPLC analysis (method as described above) indicated that the reaction proceeded with 70% enantioselectivity.

Alternatively the reaction could be conducted under otherwise identical conditions, but using antracen-9-yl-methyl quininium chloride (0.25 molar equivalents) as a catalyst and adding cesium chloride (0.1 molar equivalents) as an additive. 4-[(R)-3-Cyano-3-(3,5-dichloro-phenyl)-4,4,4-trifluoro-butyryl]-2-methyl-N-(3-methyl-thietan-3-yl)-benzamide was obtained in 38% yield and chiral HPLC analysis (method as described above) indicated that the reaction proceeded with 77% enantioselectivity.

Example P11

4-[(R)-3-Cyano-3-(3,5-dichloro-phenyl)-4,4,4-trifluoro-butyryl]-2-methyl-N-[(2,2,2-trifluoro-ethylcarbamoyl)-methyl]-benzamide

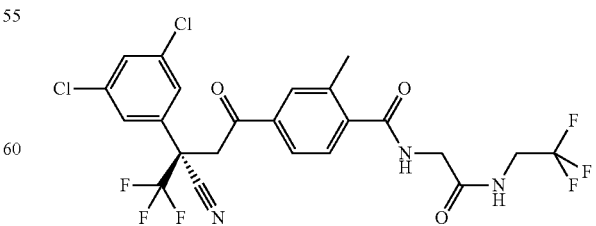

Potassium cyanide (0.0082 g, 0.125 mmol) and acetone cyanohydrin (0.031 ml, 0.336 mmol) were added to a solution of 4-[(E)-3-(3,5-Dichloro-phenyl)-4,4,4-trifluoro-but-2- enoyl]-2-methyl-N-[(2,2,2-trifluoro-ethylcarbamoyl)-methyl]-benzamide (0.0600 g, 0.111 mmol) in toluene (3.0 ml). To this vigorously stirred suspension was added antracen-9-yl-methyl quininium chloride (0.0153 g, 0.028 mmol). The reaction mixture was stirred at 90 C for 4 days. After this time water was added and the reaction mixture was extracted with dichloromethane (3×). The crude product was purified by flash chromatography (0% to 25% ethyl acetate in cyclohexane) to afford 4-[(R)-3-Cyano-3-(3,5-dichloro-phenyl)-4,4,4-trifluoro-butyryl]-2-methyl-N-[(2,2,2-trifluoro-ethylcarbamoyl)-methyl]-benzamide (0.020 g, 32%) as a light yellow solid. Chiral HPLC analysis (Chiralpack AS-RH, acetonitrile:water:methanol=45:5:50, 1 ml/min, retention time 8.70 minutes (major enantiomer), 11.30 minutes (minor enantiomer) indicated that the reaction proceeded with 94% enantioselectivity.

$^1$H NMR (400 MHz, CDCl$_3$) δ 7.68-7.64 (m, 2H), 7.49-7.45 (m, 1H), 7.37-7.36 (m, 1H), 7.35-7.33 (m, 1H), 7.17-7.09 (m, 3H), 6.85-6.80 (m, 1H), 4.25-4.20 (m, 2H), 3.99-3.90 (m, 2H), 2.46 (s, 3H)

Example P12

4-[3-[(Benzhydrylidene-amino)-tert-butoxycarbonyl-methyl]-3-(3,5-dichloro-phenyl)-4,4,4-trifluoro-butyryl]-2-methyl-benzoic acid tert-butyl ester

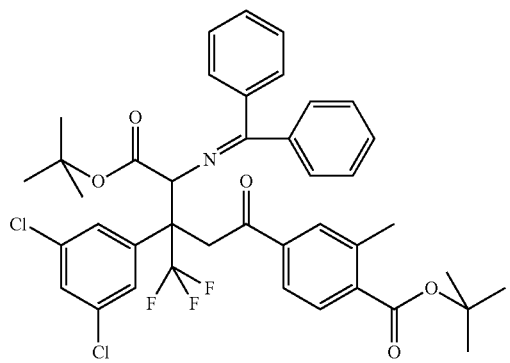 [SMILES: Cc1cc(C(=O)CC(c2cc(Cl)cc(Cl)c2)(C(N=C(c2ccccc2)c2ccccc2)C(=O)OC(C)(C)C)C(F)(F)F)ccc1C(=O)OC(C)(C)C]

4-[(E)-3-(3,5-dichloro-phenyl)-4,4,4-trifluoro-but-2-enoyl]-2-methyl-benzoic acid tert-butyl ester (0.100 g, 0.218 mmol) and (benzhydrylidene-amino)-acetic acid tert-butyl ester (0.079 g, 0.261 mmol) were dissolved in acetonitrile (5.0 ml). Potassium hydroxide (0.013 g, 0.239 mmol) and antracen-9-yl-methyl quininium chloride (0.030 g, 0.054 mmol) were added and the resulting mixture was heated at 90 C for 6 days. At this time water was added and the reaction mixture was extracted with dichloromethane (3×). The crude product was purified by flash chromatography (0% to 15% ethyl acetate in cyclohexane) to afford 4-[3-[(Benzhydrylidene-amino)-tert-butoxycarbonyl-methyl]-3-(3,5-dichloro-phenyl)-4,4,4-trifluoro-butyryl]-2-methyl-benzoic acid tert-butyl ester (0.035 g, 21%) as a white solid. Chiral HPLC analysis (Chiralpack IA, heptanes:t-buthanol=98:2, 1 ml/min, retention time 8.50 minutes and 9.23 minutes (enantiomers of the minor diasteromer); 13.37 minutes and 14.81 (enantiomers of the major diastereomer) indicated that the reaction products were formed in diastereomeric ratio 2:1.

Similarly, 4-[(E)-3-(3,5-dichloro-phenyl)-4,4,4-trifluoro-but-2-enoyl]-2-methyl-benzoic acid tert-butyl ester (1 gl) and (benzhydrylidene-amino)-acetic acid tert-butyl ester (322 mg) were dissolved in dichloromethane (13 ml). Cesium hydroxide hydrate (1.82 g) and O-Allyl-N-(9-anthracenylmethyl)cinchonidinium bromide (66 mg) were added and the resulting mixture was stirred at −75 C for 18 hours. At this time water was added and the reaction mixture was extracted with ethyl acetate. The organic layers were combined, dried over magnesium sulfate, filtered and evaporated in vacuo to give a crude residue which was purified by flash chromatography (0% to 05% dichloromethane in heptane) to afford 4-[3-[(Benzhydrylidene-amino)-tert-butoxycarbonyl-methyl]-3-(3,5-dichloro-phenyl)-4,4,4-trifluoro-butyryl]-2-methyl-benzoic acid tert-butyl ester (426 mg) as a yellow foam and a single diastereoisomer. $^{19}$F NMR (376 MHz, CDCl$_3$) δ −61 ppm (1 diastereoisomer).

The same reaction was also performed under non-chiral conditions:

To a solution of 4-[(E)-3-(3,5-dichloro-phenyl)-4,4,4-trifluoro-but-2-enoyl]-2-methyl-benzoic acid tert-butyl ester (1 g) and (benzhydrylidene-amino)-acetic acid tert-butyl ester (643 mg) in acetonitrile (5 mL) was added a solution of sodium hydroxide (0.6 mL, 32%) at room temperature. The reaction was stirred at ambient temperature for 18 hours, then water was added and the reaction mixture was extracted with dichloromethane and the combined organic fractions were dried over sodium sulfate. The crude product was purified by flash chromatography (0% to 05% ethyl acetate in cyclohexane) to afford 4-[3-[(Benzhydrylidene-amino)-tert-butoxycarbonyl-methyl]-3-(3,5-dichloro-phenyl)-4,4,4-trifluoro-butyryl]-2-methyl-benzoic acid tert-butyl ester (1.12 g) as a yellow foam. $^{19}$F NMR (376 MHz, CDCl$_3$) δ −60.99 and −61.88 ppm (mixture of 2 diastereoisomers).

Example P13 tert-butyl 5-(4-tert-butoxycarbonyl-3-methyl-phenyl)-3-(3,5-dichlorophenyl)-3-(trifluoromethyl)-2,4-dihydropyrrole-2-carboxylate

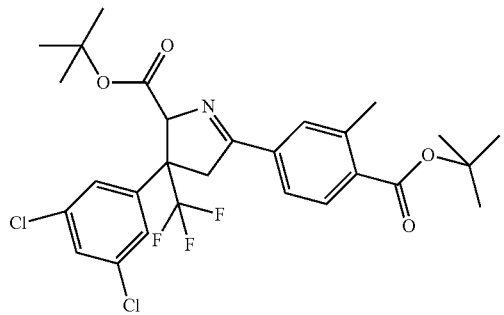 [SMILES: Cc1cc(C2=NC(C(=O)OC(C)(C)C)C(c3cc(Cl)cc(Cl)c3)(C(F)(F)F)C2)ccc1C(=O)OC(C)(C)C]

To a solution of 4-[3-[(Benzhydrylidene-amino)-tert-butoxycarbonyl-methyl]-3-(3,5-dichloro-phenyl)-4,4,4-trifluoro-butyryl]-2-methyl-benzoic acid tert-butyl ester (430 mg) in acetone (3 mL) was added hydrochloric acid (3 mL, 10%) and the solution was stirred at ambient temperature for 18 hours. Water was then added and the reaction mixture was extracted with ethylacetate and the combined organic fractions were dried over sodium sulfate. The crude product was used as such in the next step.

Similarly, the reaction was carried out under similar conditions: To a solution of 4-[3-[(Benzhydrylidene-amino)-tert-butoxycarbonyl-methyl]-3-(3,5-dichloro-phenyl)-4,4,4-trifluoro-butyryl]-2-methyl-benzoic acid tert-butyl ester (426 mg, one diastereoisomer, obtained in example P12) in acetone (12 mL) was added hydrochloric acid (6 mL, 10%)

and the solution was stirred at ambient temperature for 3 hours. Water was then added and the reaction mixture was extracted with ethylacetate and the combined organic fractions were dried over sodium sulfate. The crude product was purified by flash chromatography (0% to 05% dichloromethane in heptane) to afford tert-butyl 5-(4-tert-butoxycarbonyl-3-methyl-phenyl)-3-(3,5-dichlorophenyl)-3-(trifluoromethyl)-2,4-dihydropyrrole-2-carboxylate (248 mg) as a white solid. $^{19}$F NMR (376 MHz, CDCl$_3$) δ −75.20 ppm (1 diastereoisomers). Chiral HPLC analysis (Chiralpack AS-RH, acetonitrile:water:methanol=55:5:40, 1 ml/min, retention time 22.87 minutes (minor enantiomer) and 25.52 minutes (major isomer) indicated that the reaction proceeded with little enantioselectivity.

Example P14

4-[3-(3,5-dichlorophenyl)-3-(trifluoromethyl)-2,4-dihydropyrrol-5-yl]-2-methyl-benzoic acid

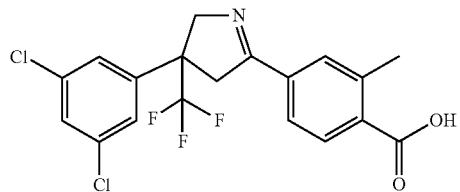 [SMILES: Cc1cc(C2=NCC(c3cc(Cl)cc(Cl)c3)(C(F)(F)F)C2)ccc1C(=O)O]

The crude product (100 mg) from the previous reaction (P13) was dissolved in dimethylsulfoxide (4 mL) and water (0.031 mL). The solution was heated under microwave conditions: two times at 160° C. for 15 minutes, then at 160° C. for 10 minutes. The reaction mixture was diluted with ethyl acetate and washed with saturated sodium hydrogenocarbonate. The combined organic fractions were washed again twice with a solution of hydrochloric acid (in order to reach pH=3), then dried over magnesium sulfate. The suspension was filtered and the solution was evaporated to give a crude residue. This residue was dissolved again in dimethylsulfoxide (4 mL) and water (0.031 mL). The solution was heated under microwave conditions: four times at 160° C. for 15 minutes. The reaction mixture was diluted with ethyl acetate and washed with saturated sodium hydrogenocarbonate. The combined organic fractions were washed again twice with a solution of hydrochloric acid (in order to reach pH=3), then dried over magnesium sulfate. The suspension was filtered and the solution was evaporated to give a crude residue. This residue was purified by flash chromatography (0% to 50% ethyl acetate in cyclohexane) to afford 4-[3-(3,5-dichlorophenyl)-3-(trifluoromethyl)-2,4-dihydropyrrol-5-yl]-2-methyl-benzoic acid (41 mg) as a yellow foam. $^{19}$F NMR (376 MHz, CDCl$_3$) δ=−75.93 ppm.

In another experiment, tert-butyl 5-(4-tert-butoxycarbonyl-3-methyl-phenyl)-3-(3,5-dichlorophenyl)-3-(trifluoromethyl)-2,4-dihydropyrrole-2-carboxylate (200 mg) was dissolved in dimethylsulfoxide (9 mL) and water (0.063 mL). The solution was heated under microwave conditions: 190° C. for 30 minutes. The reaction mixture was diluted with ethyl acetate and washed with saturated sodium hydrogenocarbonate. The combined organic fractions were washed again twice with a solution of hydrochloric acid (in order to reach pH=3), then dried over magnesium sulfate. The suspension was filtered and the solution was evaporated to give a crude residue. This residue was purified by trituration in pentane and filtration to afford 4-[3-(3,5-dichlorophenyl)-3-(trifluoromethyl)-2,4-dihydropyrrol-5-yl]-2-methyl-benzoic acid (107 mg) as a beige solid. $^{19}$F NMR (376 MHz, CDCl$_3$) δ=−75.93 ppm.

Example P15

Method for Preparing Compounds of the Invention from a Carboxylic Acid

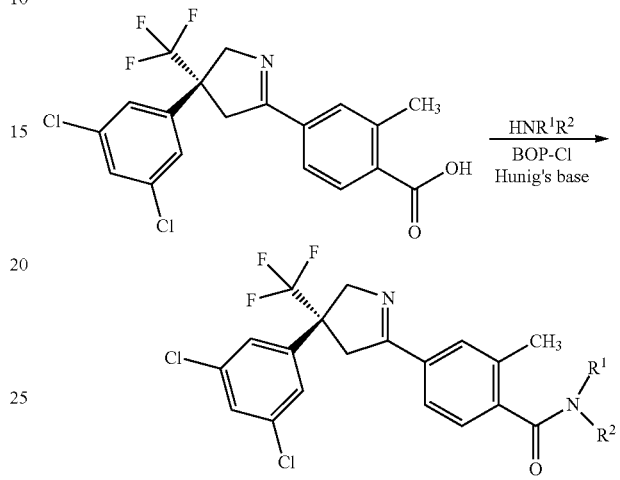

To a solution of the 4-[(3R)-3-(3,5-dichlorophenyl)-3-(trifluoromethyl)-2,4-dihydropyrrol-5-yl]-2-methyl-benzoic acid (22 mmol) in dimethylacetamide (0.4 ml) was added successively a solution of an amine of formula HNR$^6$R$^7$ (26 mmol), for example thietan-3-ylamine (preparation described in, for example, WO 2007/080131) in the case of Compound No. A1 of Table A, in dimethylacetamide (0.11 ml), diisopropylethylamine (Hunig's Base) (0.030 ml), and a solution of bis(2-oxo-3-oxazolidinyl)phosphonic chloride ("BOP—Cl") (11.2 mg) in dimethylacetamide (0.02 ml). The reaction mixture was stirred at 80° C. for 16 hours. Then the reaction mixture was diluted with acetonitrile (0.6 ml) and a sample was used for LC-MS analysis. The remaining mixture was further diluted with acetonitrile/dimethylformamide (4:1) (0.8 ml) and purified by HPLC. This method was used to prepare a number of compounds (Compound Nos. A1 to A22 of Table A) in parallel.

TABLE A

Table A provides compounds of formula (Ix) where R$^1$ is trifluoromethyl, R$^2$ is 3,5-dichloro-phenyl-, R$^{5b}$ is methyl, and R$^6$ and R$^7$ have the values listed in the table below.

(Ix)

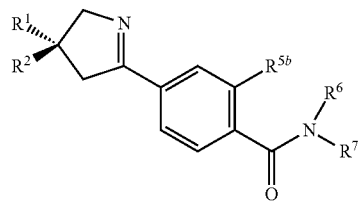

| Compound No. | R$^6$ | R$^7$ | RT (min) | [M + H]$^+$ |
|---|---|---|---|---|
| A1 | H | Thietan-3-yl | 1.88 | 487.28 |
| A2 | H | 1-Oxo-thietan-3-yl | 1.59 | 503.21 |
| A3 | H | 3-Methyl-thietan-3-yl | 1.97 | 501.25 |
| A4 | H | N-(2,2,2-trifluoro-ethyl)-acetamide | 1.76 | 554.26 |

TABLE A-continued

Table A provides compounds of formula (Ix) where $R^1$ is trifluoromethyl, $R^2$ is 3,5-dichloro-phenyl-, $R^{5b}$ is methyl, and $R^6$ and $R^7$ have the values listed in the table below.

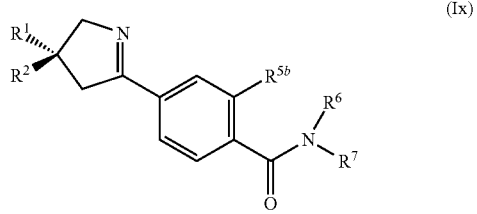

(Ix)

| Compound No. | $R^6$ | $R^7$ | RT (min) | $[M + H]^+$ |
|---|---|---|---|---|
| A5 | H | thietan-3-ylmethyl | 1.88 | 501.26 |
| A6 | H | oxetan-3-yl | 2.12 | 471.31 |
| A7 | H | 3-(2,2,2-trifluoroethoxyimino)cyclobutyl | 1.97 | 580.18 |
| A8 | H | thietan-2-ylmethyl | 1.9 | 501.25 |
| A9 | H | (1,1-dioxothietan-2-yl)methyl | 1.68 | 533.23 |
| A10 | H | 2-(thietan-3-yl)ethyl | 1.93 | 515.2 |
| A11 | H | 2-(1,1-dioxothietan-3-yl)ethyl | 1.68 | 547.2 |
| A12 | H | 2,2,2-Trifluoro-ethyl | 1.9 | 497.23 |
| A13 | H | butyl | 1.96 | 471.3 |
| A14 | H | 3,3,3-trifluoroprop-1-yl | 1.91 | 511.25 |
| A15 | H | benzyl | 1.97 | 505.24 |
| A16 | H | (2-fluorophenyl)-methyl | 1.98 | 523.27 |
| A17 | H | (4-methoxyphenyl)-methyl | 1.95 | 535.28 |
| A18 | H | 3-fluorophenyl | 2.07 | 509.24 |
| A19 | H | 2-pyridylmethyl | 1.64 | 506.27 |
| A20 | H | Cyclobutyl | 1.91 | 469.29 |
| A21 | H | 2-methylsulfanylethyl | 1.86 | 489.32 |
| A22 | H | tetrahydrothiophen-3-yl | 1.89 | 501.24 |

Corresponding LC/MS Method

| MS | ACQUITY SQD Mass Spectrometer from Waters (Single quadrupole mass spectrometer) Ionisation method: Electrospray Polarity: positive ions Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700 Mass range: 100 to 800 Da DAD Wavelength range (nm): 210 to 400 |
|---|---|
| LC | Method Waters ACQUITY UPLC with the following HPLC gradient conditions (Solvent A: Water/Methanol 9:1, 0.1% formic acid and Solvent B: Acetonitrile, 0.1% formic acid ) |

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Examples P14 (Compound A23)

4-[(3R)-3-(3,5-dichlorophenyl)-3-(trifluoromethyl)-2,4-dihydropyrrol-5-yl]-N-(1,1-dioxothietan-3-yl)-2-methyl-benzamide To a stirred solution of 4-[(3R)-3-(3,5-dichlorophenyl)-3-(trifluoromethyl)-2,4-dihydropyrrol-5-yl]-2-methyl-benzoic acid (68 mg) in dichloromethane (2.5 mL) was added triethylamine (0.05 mL) at ambient temperature. The solution was then stirred for 5 min under argon and trifluoroacetate salt of 1,1-Dioxo-llambda*6*-thietan-3-ylamine (46 mg) was added. To this solution, 1-hydroxyazabenzotriazole (25 mg) then 1-(3-Dimethylaminopropyl)-3-ethylcarbodiimide hydrochloride (35 mg) were added. The solution was stirred at ambient temperature for 3 days. The reaction mixture was diluted with ethyl acetate and washed with water. The combined organic phases were dried over anhydrous sodium sulfate, the suspension was filtered and the solution was evaporated to give a crude residue which was purified by chromatography on silica gel (eluent: heptane/ethyl acetate, from 1:0 to 6:4) to give 4-[(3R)-3-(3,5-dichlorophenyl)-3-(trifluoromethyl)-2,4-dihydropyrrol-5-yl]-N-(1,1-dioxothietan-3-yl)-2-methyl-benzamide (30 mg) as a white solid.

$^{19}F$ NMR (376 MHz, CDCl$_3$) δ=−76.00 ppm.

HPLC analysis (Chiralpack IB, Heptane:2-propanol=70:30+0.1 diethylamine, 1 ml/min, retention time 18.59 minutes (minor enantiomer), 22.85 minutes (major enantiomer) indicated that the compound is 97% enantioenriched.

Similarly, using 4-[(3S)-3-(3,5-dichlorophenyl)-3-(trifluoromethyl)-2,4-dihydropyrrol-5-yl]-2-methyl-benzoic acid, the preparation of 4-[(3S)-3-(3,5-dichlorophenyl)-3-(trifluoromethyl)-2,4-dihydropyrrol-5-yl]-N-(1,1-dioxothietan-3-yl)-2-methyl-benzamide (compound A24) could be achieved. HPLC analysis (Chiralpack IA, Heptane:2-propanol=70:30, 1 ml/min, retention time 9.86 minutes (minor enantiomer), 24.97 minutes (major enantiomer) indicated that the compound is 82% enantioenriched.

Biological Examples

These examples illustrate the comparative insecticidal and acaricidal properties of compounds A23 and A24. The tests were performed as follows:

*Heliothis virescens* (Tobacco Budworm):

Eggs (0-24 h old) were placed in 24-well microtiter plate on artificial diet and treated with test solutions at an application rate of 12.5 ppm (concentration in well 18 ppm) by pipetting. After an incubation period of 4 days, samples were checked for egg mortality, larval mortality, and growth regulation.

| Insects: *Heliothis virescens* | % Control at 200 ppm | % Control at 12.5 ppm |
|---|---|---|
| Compound A23 | 100 | 100 |
| Compound A24 | 100 | 50 |

*Diabrotica balteata* (Corn Root Worm):

A 24-well microtiter plate (MTP) with artificial diet was treated with test solutions at an application rate of 12.5 ppm (concentration in well 18 ppm) by pipetting. After drying, the MTP's were infested with L2 larvae (6-10 per well). After an incubation period of 5 days, samples were checked for larval mortality and growth regulation.

| Insects: *Diabrotica balteata* | % Control at 200 ppm | % Control at 12.5 ppm |
|---|---|---|
| Compound A23 | 100 | 100 |
| Compound A24 | 100 | 0 |

*Thrips tabaci* (Onion Thrips):

Sunflower leaf discs were placed on agar in a 24-well microtiter plate and sprayed with test solutions at an application rate of 50 ppm. After drying, the leaf discs were infested with an aphid population of mixed ages. After an incubation period of 7 days, samples were checked for mortality.

| Insects: Thrips tabaci | % Control at 200 ppm | % Control at 12.5 ppm |
|---|---|---|
| Compound A23 | 100 | 100 |
| Compound A24 | 100 | 40 |

What is claimed is:

1. A process for the preparation of the compound of formula I

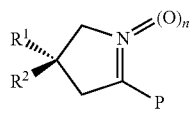
(I)

wherein
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
$R^1$ is chlorodifluoromethyl or trifluoromethyl;
$R^2$ is optionally substituted aryl or optionally substituted heteroaryl;
n is 0 or 1;
comprising
(a-i) reacting a compound of formula II

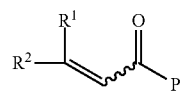
(II)

wherein P, $R^1$ and $R^2$ are as defined for the compound of formula I;
with nitromethane in the presence a chiral catalyst to give a compound of formula III

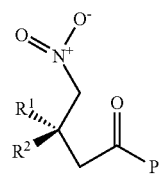
(III)

wherein P, $R^1$ and $R^2$ are as defined for the compound of formula I; and
(a-ii) reductively cyclising the compound of formula III to give the compound of formula I; or
(b-i) reacting a compound of formula II

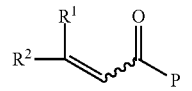
(II)

wherein P, $R^1$ and $R^2$ are as defined for the compound of formula I;

with a source of cyanide in the presence of a chiral catalyst to give a compound of formula IV

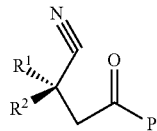
(IV)

wherein P, $R^1$ and $R^2$ are as defined for the compound of formula I; and
(b-ii) reductively cyclising the compound of formula IV to give the compound of formula I, wherein n is 0;
or
(c-i) reacting a compound of formula II

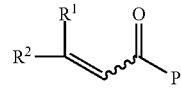
(II)

wherein P, $R^1$ and $R^2$ are as defined for the compound of formula I;
with a compound of formula XXII

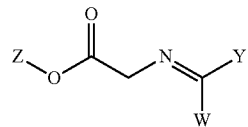
(XXII)

wherein wherein W is hydrogen or optionally substituted aryl, Y is optionally substituted aryl, and Z is optionally substituted alkyl or optionally substituted arylalkylene;
in the presence a chiral catalyst to give a compound of formula XXIII

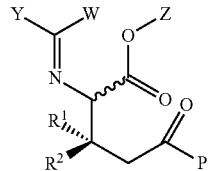
(XXIII)

wherein P, $R^1$ and $R^2$ are as defined for the compound of formula I, and Y, W and Z are as defined for the compound of formula XXII;
(c-ii) treating the compound of formula XXIII with a suitable acid or a suitable base to release Y—C(=O)—W and give the compound of formula XXIV

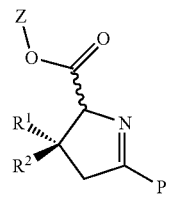
(XXIV)

wherein P, $R^1$ and $R^2$ are as defined for the compound of formula I and Z is as defined for the compound of formula XXII; and (c-iii) decarboxylating the compound XXIV to give the compound I, wherein n is 0;
or
(d-i) reacting a compound of formula XXV

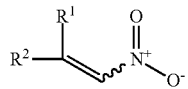

(XXV)

wherein $R^1$ and $R^2$ are as defined for the compound of formula I;
with a compound of formula XXVI

(XXVI)

wherein P is as defined for the compound of formula I;
in the presence a chiral catalyst to give a compound of formula III

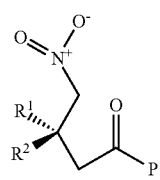

(III)

wherein P, $R^1$ and $R^2$ are as defined for the compound of formula I; and
(d-ii) reductively cyclising the compound of formula III to give the compound of formula I.

2. A process according to claim 1, wherein the compound of formula I is prepared according to process (a) or process (b).

3. A process according to claim 1, wherein the chiral catalyst is a chiral cinchona alkaloid derivative, a chiral thiourea derivative, a chiral urea derivative, a chiral aza-crown ether derivative, a chiral metal complex, a chiral amidine or guanidine derivative, a chiral pyrrolidine or imidazolidine derivative, a chiral scandium III complex, a chiral naphthyl phase transfer catalyst, a chiral galodinium or strontium catalysts, a chiral crown ether derivative, or a chiral ligand for an alkaline earth metal.

4. A process according to claim 1, wherein the chiral catalyst is a chiral cinchona alkaloid derivative.

5. A process according to claim 4, wherein the compound of formula I is prepared according to process (a) and the chiral cinchona alkaloid derivative is a compound of formula VII,

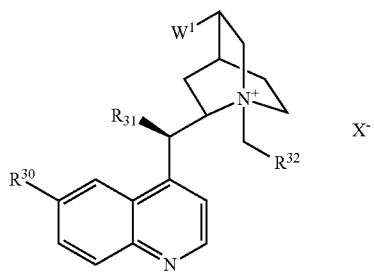

(VII)

wherein
$W^1$ is ethyl or vinyl; $R^{30}$ is hydrogen or $C_1$-$C_4$alkoxy; $R^{31}$ is hydroxyl, $C_1$-$C_4$alkoxy, $C_2$-$C_4$alkenyloxy or optionally substituted benzyloxy; $R^{32}$ is optionally substituted aryl or optionally substituted heteroaryl; X is an anion;
or
a compound of formula IX

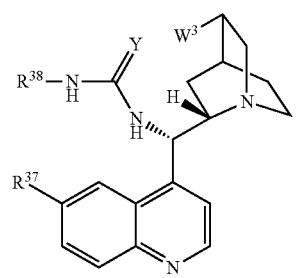

(IX)

wherein
Y is S or O, $W^3$ is ethyl or vinyl; $R^{37}$ is hydrogen or $C_1$-$C_4$alkoxy; $R^{38}$ is optionally substituted aryl or optionally substituted $C_3$-$C_{10}$cycloalkyl; or
a compound of formula X

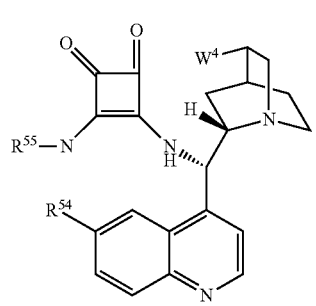

(X)

wherein $W^4$ is ethyl or vinyl; $R^{54}$ is hydrogen or $C_1$-$C_4$alkoxy; $R^{55}$ is optionally substituted aryl.

6. A process according to claim 5, wherein the chiral cinchona alkaloid derivative is a compound of formula IX.

7. A process according to claim 4, wherein the compound of formula I is prepared according to process (b) and the chiral cinchona alkaloid derivative is a compound of formula VII

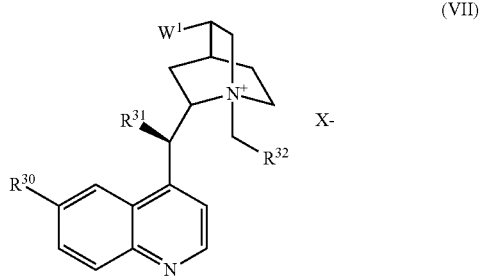

(VII)

wherein
$W^1$ is ethyl or vinyl; $R^{30}$ is hydrogen or $C_1$-$C_4$alkoxy; $R^{31}$ is hydroxyl, $C_1$-$C_4$alkoxy, $C_2$-$C_4$alkenyloxy or optionally substituted benzyloxy; $R^{32}$ is optionally substituted aryl or optionally substituted heteroaryl; X is an anion.

8. A process according to claim 4, wherein the compound of formula I is prepared according to process (c) and the chiral cinchona alkaloid derivative is a compound of formula VII

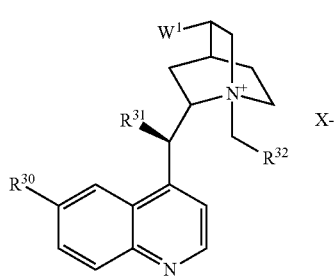

(VII)

wherein
$W^1$ is ethyl or vinyl; $R^{30}$ is hydrogen or $C_1$-$C_4$alkoxy; $R^{31}$ is $C_2$-$C_4$alkenyloxy or optionally substituted benzyloxy; $R^{32}$ is optionally substituted aryl or optionally substituted heteroaryl; X is an anion.

9. A process for the preparation of the compound of formula Ir

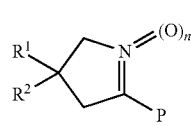

(Ir)

wherein
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
$R^1$ is chlorodifluoromethyl or trifluoromethyl;
$R^2$ is optionally substituted aryl or optionally substituted heteroaryl;
n is 0 or 1;
comprising
(cr-i) reacting a compound of formula II

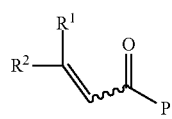

(II)

wherein P, $R^1$ and $R^2$ are as defined for the compound of formula I;
with a compound of formula XXII

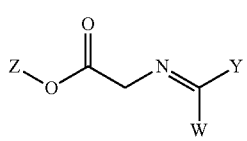

(XXII)

wherein wherein W is hydrogen or optionally substituted aryl, Y is optionally substituted aryl, and Z is optionally substituted alkyl or optionally substituted arylalkylene; to give a compound of formula XXIIIr

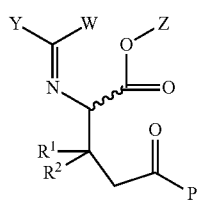

(XXIIIr)

wherein P, $R^1$ and $R^2$ are as defined for the compound of formula I, and Y, W and Z are as defined for the compound of formula XXII;
(cr-ii) treating the compound of formula XXIIIr with a suitable acid or a suitable base to release Y-C(=O)—W and give the compound of formula XXIVr

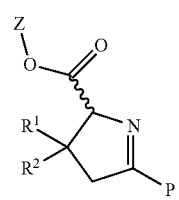

(XXIVr)

wherein P, $R^1$ and $R^2$ are as defined for the compound of formula I and Z is as defined for the compound of formula XXII; and
(cr-iii) decarboxylating the compound XXIVr to give the compound I, wherein n is 0.

10. A process for the preparation of the compound of formula Ir

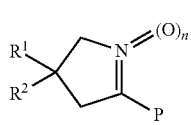

(Ir)

wherein
P is phenyl, naphthyl, a 6-membered heteroaryl group containing one or two nitrogen atoms as ring members, or a 10-membered bicyclic heteroaryl group containing one or two nitrogen atoms as ring members, and wherein the phenyl, naphthyl and heteroaryl groups are optionally substituted;
$R^1$ is chlorodifluoromethyl or trifluoromethyl;
$R^2$ is optionally substituted aryl or optionally substituted heteroaryl;
n is 0 or 1;
comprising
(dr-i) reacting a compound of formula XXV

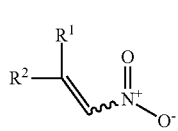

(XXV)

wherein $R^1$ and $R^2$ are as defined for the compound of formula I;

with a compound of formula XXVI

(XXVI)

wherein P is as defined for the compound of formula I; to give a compound of formula IIIr

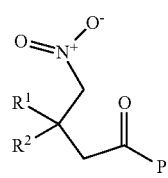

(IIIr)

wherein P, $R^1$ and $R^2$ are as defined for the compound of formula I; and (dr-ii) reductively cyclising the compound of formula IIIr to give the compound of formula I.

11. A process according to claim 1, wherein $R^2$ is aryl or aryl substituted by one to five $R^3$, or heteroaryl or heteroaryl substituted by one to five $R^3$;

each $R^3$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkylamino, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^4$, or heterocyclyl or heterocyclyl substituted by one to five $R^4$;

P is P1 or P2

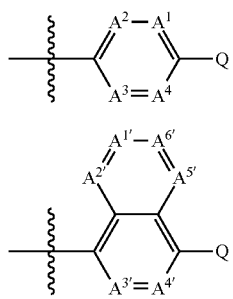

(P1)

(P2)

$A^1$, $A^2$, $A^3$, $A^4$ are independently of each other C—H, C—$R^5$ or nitrogen, provided that no more than two of $A^1$, $A^2$, $A^3$, $A^4$ are nitrogen;

$A^{1'}$, $A^{2'}$, $A^{3'}$, $A^{4'}$, $A^{5'}$ and $A^{6'}$ are independently of each other C—H, C—$R^5$ or nitrogen, provided that no more than two of $A^{1'}$, $A^{2'}$, $A^{3'}$, $A^{4'}$, $A^{5'}$ and $A^{6'}$ are nitrogen;

each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl or $C_1$-$C_8$haloalkylsulfonyl;

Q is hydrogen, halogen, nitro, $NH_2$, cyano, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_3$-$C_8$haloalkynyl, $C_3$-$C_{10}$cycloalkyl, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, arylsulfonyl or arylsulfonyl substituted by one to five groups independently selected from $C_1$-$C_4$ alkyl and nitro, —N($R^6$)$R^{7b}$, —C(=W)N($R^6$)$R^7$, —C($R^{15}$)($R^{16}$)N($R^{17}$)$R^{18}$, —C(=W)O$R^{7a}$, —C(=W)$R^{13}$, —O$R^{14}$, aryl or aryl substituted by one to five Z, heterocyclyl or heterocyclyl substituted by one to five Z;

$R^6$ is hydrogen, $C_1$-$C_8$alkyl, $C_1$-$C_8$alkoxy, $C_2$-$C_8$alkenyl, $C_2$-$C_8$alkynyl, $C_3$-$C_{10}$cycloalkyl, $C_3$-$C_{10}$cycloalkyl-$C_1$-$C_4$alkylene, $C_1$-$C_8$alkylcarbonyl or $C_1$-$C_8$alkoxycarbonyl;

$R^7$ is hydrogen, alkyl or alkyl substituted by one to five $R^8$, alkenyl or alkenyl substituted by one to five $R^8$, alkynyl or alkynyl substituted by one to five $R^8$, $C_3$-$C_{10}$cycloalkyl or $C_3$-$C_{10}$cycloalkyl substituted by one to five $R^9$, $C_3$-$C_{10}$cycloalkyl-$C_1$-$C_4$alkylene or $C_3$-$C_{10}$cycloalkyl-$C_1$-$C_4$ alkylene wherein the cycloalkyl moiety is substituted by one to five $R^9$, $C_1$-$C_8$alkyl-N($R^6$)—C(=O)—$C_1$-$C_4$alkylene, $C_1$-$C_8$haloalkyl-N($R^6$)—C(=O)—$C_1$-$C_4$alkylene, $C_3$-$C_8$cycloalkyl-aminocarbonyl-$C_1$-$C_4$alkylene, $C_1$-$C_6$alkyl-O—N=CH—, $C_1$-$C_6$haloalkyl-O—N=CH—, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein the heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$; aryl or aryl substituted by one to five $R^{10}$, heterocyclyl or heterocyclyl substituted by one to five $R^{10}$ and wherein the heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$;

$R^{7a}$ is hydrogen, alkyl or alkyl substituted by one to five $R^8$, alkenyl or alkenyl substituted by one to five $R^8$, alkynyl or alkynyl substituted by one to five $R^8$, cycloalkyl or cycloalkyl substituted by one to five $R^9$, aryl-alkylene or aryl-alkylene wherein the aryl moiety is is substituted by one to five $R^{10}$, heteroaryl-alkylene or heteroaryl-alkylene wherein the heteroaryl moiety is substituted by one to five $R^{10}$, aryl or aryl substituted by one to five $R^{10}$, or heteroaryl or heteroaryl substituted by one to five $R^{10}$;

$R^{7b}$ is hydrogen, alkyl, haloalkyl, alkenyl, haloalkenyl, alkynyl, haloalkynyl cycloalkyl, halocycloalkyl, alkylcarbonyl, haloalkylcarbonyl, alkoxycarbonyl, haloalkoxycarbonyl, or benzyl;

each $R^8$ is independently halogen, cyano, nitro, hydroxy, $NH_2$, mercapto, $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylamino, $C_2$-$C_8$dialkylamino, $C_3$-$C_8$cycloalkylamino, $C_1$-$C_8$alkylcarbonyl, $C_1$-$C_8$alkoxycarbonyl, $C_1$-$C_8$alkylaminocarbonyl, $C_1$-$C_8$dialkylaminocarbonyl, $C_1$-$C_8$haloalkylcarbonyl, $C_1$-$C_8$haloalkoxycarbonyl, $C_1$-

$C_8$haloalkylaminocarbonyl, $C_1$-$C_8$halodialkylaminocarbonyl;

each $R^9$ is independently halogen or $C_1$-$C_8$alkyl;

each $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{11}$, or heterocyclyl or heterocyclyl substituted by one to five $R^{11}$;

each $R^4$ and $R^{11}$ is independently halogen, cyano, nitro, $C_1$-$C_8$alkyl, $C_1$-$C_8$haloalkyl, $C_1$-$C_8$alkoxy, $C_r$-$C_8$haloalkoxy or $C_1$-$C_8$alkoxycarbonyl;

each $R^{12}$ is independently hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or SO$_2$, or $C_3$-$C_8$cycloalkyl-$C_1$-$C_8$alkylene, $C_3$-$C_8$cycloalkyl-$C_1$-$C_8$alkylene where one carbon atom in the cycloalkyl group is replaced by O, S, S(O) or SO$_2$, or $C_3$-$C_8$cycloalkyl-$C_1$-$C_8$haloalkylene, $C_1$-$C_8$hydroxyalkyl, $C_1$-$C_8$alkoxy$C_1$-$C_8$alkylene, $C_2$-$C_8$alkenyl, $C_2$-$C_8$haloalkenyl, $C_2$-$C_8$alkynyl, $C_2$-$C_8$haloalkynyl, aryl or aryl substituted by one to three $R^{11}$, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_8$alkylene or aryl-$C_1$-$C_8$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$, or $C_1$-$C_4$alkyl-($C_1$-$C_4$alkyl-O—N=)C—CH$_2$—;

$R^{13}$ is halogen or imidazole;

each $R^{14}$ is independently hydrogen, $C_1$-$C_8$alkyl, $C_2$-$C_8$alkenyl, $C_2$-$C_8$alkynyl, $C_3$-$C_{10}$cycloalkyl, $C_1$-$C_6$alkyl-$C_3$-$C_8$cycloalkyl, $C_3$-$C_8$cycloalkyl-$C_1$-$C_6$alkylene, $C_1$-$C_{10}$alkylcarbonyl, $C_1$-$C_8$alkoxycarbonyl, $C_1$-$C_8$alkylsulfonyl, $C_1$-$C_8$haloalkylsulfonyl, or arylsulfonyl or arylsulfonyl substituted by one to five groups independently independently selected from $C_1$-$C_4$alkyl and nitro;

each $R^{15}$ and $R^{16}$ is independently hydrogen, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, cyano, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, or $R^{15}$ and $R^{16}$ together with the carbon atom to which they are attached may form a 3 to 6-membered carbocyclic ring;

$R^{17}$ is hydrogen, NH$_2$, hydroxyl, $C_1$-$C_{12}$alkoxy or $C_1$-$C_{12}$alkoxy substituted by one to five $R^8$, $C_1$-$C_{12}$alkylcarbonylamino or $C_1$-$C_{12}$alkylcarbonylamino wherein the alkyl is substituted by one to five $R^8$, $C_1$-$C_{12}$alkylamino or $C_1$-$C_{12}$alkylamino wherein the alkyl is substituted by one to five $R^8$, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, cyano, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, $C_1$-$C_{12}$alkylcarbonyl or $C_1$-$C_{12}$alkylcarbonyl substituted by one to five $R^8$, $C_1$-$C_{12}$alkoxycarbonyl or $C_1$-$C_{12}$alkoxycarbonyl substituted by one to five $R^8$, or is selected from CH$_2$—$R^{19}$, C(=O)$R^{19}$ and C(=S)$R^{19}$;

$R^{18}$ is hydrogen, cyano, carbonyl, thiocarbonyl, $C_1$-$C_{12}$alkylcarbonyl or $C_1$-$C_{12}$alkylcarbonyl substituted by one to five $R^8$, $C_1$-$C_{12}$alkylthiocarbonyl or $C_1$-$C_{12}$alkylthiocarbonyl substituted by one to five $R^8$, $C_1$-$C_{12}$alkylaminocarbonyl or $C_1$-$C_{12}$alkylaminocarbonyl wherein the alkyl is substituted by one to five $R^8$, $C_1$-$C_{12}$alkylaminothiocarbonyl or $C_1$-$C_{12}$alkylaminothiocarbonyl wherein the alkyl is substituted by one to five $R^8$, $C_2$-$C_{14}$ (total carbon number) dialkylaminocarbonyl or $C_2$-$C_{24}$ (total carbon number) dialkylaminocarbonyl wherein one or both alkyl is substituted by one to five $R^8$, $C_2$-$C_{24}$ (total carbon number) dialkylaminothiocarbonyl or $C_2$-$C_{24}$ (total carbon number) dialkylaminothiocarbonyl wherein one or both alkyl is substituted by one to five $R^8$, $C_1$-$C_{12}$alkoxyaminocarbonyl or $C_1$-$C_{12}$alkoxyaminocarbonyl wherein the alkoxy is substituted by one to five $R^8$, $C_1$-$C_{12}$alkoxyaminothiocarbonyl or $C_1$-$C_{12}$alkoxyaminothiocarbonyl wherein the alkoxy is substituted by one to five $R^8$, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, $C_1$-$C_{12}$thioalkoxycarbonyl or $C_1$-$C_{12}$thioalkoxycarbonyl substituted by one to five $R^8$, $C_1$-$C_{12}$thioalkoxythiocarbonyl or $C_1$-$C_{12}$thioalkoxythiocarbonyl substituted by one to five $R^8$, $C_1$-$C_{12}$alkylsulfonyl or $C_1$-$C_{12}$alkylsulfonyl substituted by one to five $R^8$, $C_3$-$C_{12}$cycloalkylcarbonyl or $C_3$-$C_{12}$cycloalkylcarbonyl substituted by one to five $R^9$, $C_2$-$C_{12}$alkenylcarbonyl or $C_2$-$C_{12}$alkenylcarbonyl substituted by one to five $R^9$, $C_2$-$C_{12}$alkynylcarbonyl or $C_2$-$C_{12}$alkynylcarbonyl substituted by one to five $R^9$, $C_3$-$C_{12}$cycloalkyl-$C_1$-$C_{12}$alkylcarbonyl or $C_3$-$C_{12}$cycloalkyl-$C_1$-$C_{12}$alkylcarbonyl substituted by one to five $R^9$, $C_1$-$C_{12}$alkylsulfenyl-$C_1$-$C_{12}$alkylcarbonyl or $C_1$-$C_{12}$alkylsulfenyl-$C_1$-$C_{12}$alkylcarbonyl substituted by one to five $R^9$, $C_1$-$C_{12}$alkylsulfinyl-$C_1$-$C_{12}$alkylcarbonyl or $C_1$-$C_{12}$alkylsulfinyl-$C_1$-$C_{12}$alkylcarbonyl substituted by one to five $R^9$, $C_1$-$C_{12}$alkylsulfonyl-$C_1$-$C_{12}$alkylcarbonyl or $C_1$-$C_{12}$alkylsulfonyl-$C_1$-$C_{12}$alkylcarbonyl substituted by one to five $R^9$, $C_1$-$C_{12}$alkylcarbonyl-$C_1$-$C_{12}$alkylcarbonyl or $C_1$-$C_{12}$alkylcarbonyl-$C_1$-$C_{12}$alkylcarbonyl substituted by one to five $R^9$, $C_3$-$C_{12}$cycloalkylaminocarbonyl or $C_3$-$C_{12}$cycloalkylaminocarbonyl wherein the cycloalkyl is substituted by one to five $R^9$, $C_2$-$C_{12}$alkenylaminocarbonyl or $C_2$-$C_{12}$alkenylaminocarbonyl wherein the alkenyl is substituted by one to five $R^9$, $C_2$-$C_{12}$alkynylaminocarbonyl or $C_2$-$C_{12}$alkynylaminocarbonyl wherein the alkynyl is substituted by one to five $R^9$, or is selected from C(=O)$R^{19}$ and C(=S)$R^{19}$;

or $R^{17}$ and $R^{18}$ together with the nitrogen atom to which they are bound, form a 3- to 6-membered heterocyclic ring which may be substituted by one to five $R^{11}$, or may be substituted with a keto, thioketo or nitroimino group;

$R^{19}$ is aryl or aryl substituted by one to five $R^{11}$, heterocyclyl or heterocyclyl substituted by one to five $R^{11}$;

each Z is independently halogen, $C_1$-$C_{12}$alkyl or $C_1$-$C_{12}$alkyl substituted by one to five $R^8$ nitro, $C_1$-$C_{12}$alkoxy or $C_1$-$C_{12}$alkoxy substituted by one to five $R^8$, cyano, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, hydroxyl or thiol.

12. A process according to claim 11, wherein $R^2$ is phenyl or phenyl substituted by one to five $R^3$;

Q is cyano, halogen, nitro, $NH_2$, arylsulfonyl or arylsulfonyl substituted by one to five groups independently selected from $C_1$-$C_4$alkyl and nitro, heterocyclyl or heterocyclyl substituted by one to five Z, —$OR^{14}$, —C(=O)N($R^6$)$R^7$, —C(=O)$OR^{7a}$, —C(=O)$R^{13}$, or —C($R^{15}$)($R^{16}$)N($R^{17}$)$R^{18}$.

13. A process according to claim 11, wherein P is P3

(P3)

$A^3$ and $A^4$ are C—H, or one of $A^3$ and $A^4$ is C—H and the other is nitrogen;

$R^{5a}$ is hydrogen;

$R^{5b}$ is methyl;

or $R^{5a}$ and $R^{5b}$ together form a —CH=CH—CH=CH— bridge;

Q is cyano, halogen, nitro, $NH_2$, phenylsulfonyl or phenylsulfonyl substituted by one to five groups independently selected from $C_1$-$C_4$ alkyl and nitro, —$OR^{14}$, —C(=O)N($R^6$)$R^7$, —C(=O)$OR^{7a}$, —C(=O)$R^{13}$, —C($R^{15}$)($R^{16}$)N($R^{17}$)$R^{18}$ or a heterocycle selected from H1 to H9

H1

H2

H3

H4

H5

H6

H7

H8

H9 k is 0, 1 or 2;

$R^6$ is hydrogen, $C_1$-$C_8$alkyl, $C_1$-$C_8$alkoxy, $C_1$-$C_8$alkylcarbonyl, or $C_1$-$C_8$alkoxycarbonyl;

$R^7$ is hydrogen, $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, aryl or aryl substituted by one to five $R^{10}$, heterocyclyl or heterocyclyl substituted by one to five $R^{10}$, wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, $C_1$-$C_8$alkyl-N($R^6$)—C(=O)—$C_1$-$C_4$alkylene, $C_1$-$C_8$haloalkyl-N($R^6$)—C(=O)—$C_1$-$C_4$alkylene, $C_3$-$C_8$cycloalkyl-aminocarbonyl-$C_1$-$C_4$alkylene, $C_1$-$C_6$alkyl-O—N=CH—, $C_1$-$C_6$haloalkyl-O—N=CH—; $R^{7a}$ is $C_1$-$C_{15}$alkyl, $C_1$-$C_{15}$haloalkyl, $C_2$-$C_{15}$ alkenyl, $C_2$-$C_{15}$ haloalkenyl, pyridyl or benzyl.

14. A process according to claim 11, wherein Q is cyano, halogen, nitro, $NH_2$, $C_1$-$C_8$alkoxy, phenylsulfonyl or phenylsulfonyl substituted by one to five groups independently selected from $C_1$-$C_4$ alkyl and nitro, —C(=O)N($R^6$)$R^7$, —C(=O)$OR^{7a}$, —C(=O)$R^{13}$, —C($R^{15}$)($R^{16}$)N($R^{17}$)$R^{18}$, or a heterocycle selected from H1 to H9;

$R^6$ is hydrogen, $C_1$-$C_8$alkyl, $C_1$-$C_8$alkoxy, $C_1$-$C_8$alkylcarbonyl, or $C_1$-$C_8$alkoxycarbonyl;

$R^7$ is hydrogen, $C_1$-$C_8$alkyl, $C_1$-$C_8$haloalkyl, phenyl-$C_1$-$C_6$alkylene or phenyl-$C_1$-$C_6$alkylene wherein the phenyl moiety is substituted by one to five $R^{10}$, pyridyl-$C_1$-$C_6$alkylene or pyridyl-$C_1$-$C_6$alkylene wherein the pyridyl moiety is substituted by one to four $R^{10}$, thiazolyl-$C_1$-$C_6$alkylene or thiazolyl-$C_1$-$C_6$alkylene wherein the thiazolyl moiety substituted by one or two $R^{10}$, phenyl or phenyl substituted by one to five $R^{10}$, pyridyl or pyridyl substituted by one to four $R^{10}$, thiazolyl or thiazolyl substituted by one or two $R^{10}$, $C_3$-$C_6$cycloalkyl or $C_3$-$C_6$cycloalkyl wherein one ring atom is replaced by O or S, $C_1$-$C_4$alkyl-O—N=CH—, $C_1$-$C_4$haloalkyl-O—N=CH—, $C_1$-$C_4$alkyl-N($R^6$)—C(=O)—CH$_2$—, $C_1$-$C_4$haloalkyl-N($R^6$)—C(=O)—CH$_2$—, or a group of formula (A)

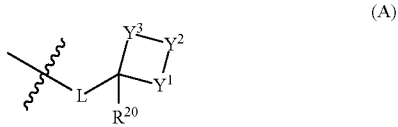

(A)

L is a single bond or $C_1$-$C_6$alkylene;
$Y^1$, $Y^2$ and $Y^3$ are independently of another $CR^{21}R^{22}$, C=O, C=N—$OR^{12}$, N—$R^{12}$, S, SO, $SO_2$, S=N—$R^{12}$ or SO=N—$R^{12}$, provided that at least one of $Y^1$, $Y^2$ or $Y^3$ is not $CR^{21}R^{22}$, C=O or C=N—$OR^{12}$;
each $R^8$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfony-;
each $R^{12}$ is independently hydrogen, cyano, $C_1$-$C_8$alkyl, $C_1$-$C_8$haloalkyl, $C_1$-$C_8$alkylcarbonyl, $C_r$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$;
$R^{15}$ and $R^{16}$ are independently selected from hydrogen, halogen, cyano, $C_1$-$C_4$alkyl, $C_1$-$C_4$haloalkyl;
$R^{17}$ is hydrogen, $C_1$-$C_8$alkyl, $C_1$-$C_8$alkoxy, $C_1$-$C_8$alkylcarbonyl, or $C_1$-$C_8$alkoxycarbonyl;
$R^{18}$ is $C_1$-$C_4$alkylcarbonyl or $C_1$-$C_4$alkylcarbonyl substituted by one to five $R^8$, $C_3$-$C_6$ cycloalkylcarbonyl or $C_3$-$C_6$cycloalkylcarbonyl wherein the cycloalkyl is substituted by one to five $R^9$;
$R^{20}$ is hydrogen or $C_1$-$C_8$alkyl;
each $R^{21}$ and $R^{22}$ is independently hydrogen, halogen, $C_1$-$C_8$alkyl or $C_1$-$C_8$haloalkyl;
each Z is independently halogen, cyano, $C_1$-$C_4$alkyl, $C_1$-$C_4$haloalkyl, $C_1$-$C_4$alkoxy, $C_1$-$C_4$haloalkoxy.

15. A process according to claim 14, wherein Q is —C(=O)N($R^6$)$R^7$, —C($R^{15}$)($R^{16}$)N($R^{17}$)$R^{18}$, or a heterocycle selected from H1 to H9.

16. A process according to claim 14, wherein Q is —C(=O)N($R^6$)$R^7$ and $R^7$ is a group of formula (A).

* * * * *